(12) United States Patent
Lee et al.

(10) Patent No.: US 11,950,922 B2
(45) Date of Patent: Apr. 9, 2024

(54) WEARABLE DEVICE FOR MEDICATION ADHERENCE MONITORING

(71) Applicant: INHANDPLUS INC., Pohang-si (KR)

(72) Inventors: Hwiwon Lee, Seoul (KR); Nam Eok Kim, Yongin-si (KR)

(73) Assignee: INHANDPLUS INC., Pohang-si (KR)

( * ) Notice: Subject to any disclaimer, the term of this patent is extended or adjusted under 35 U.S.C. 154(b) by 0 days.

(21) Appl. No.: 18/137,447

(22) Filed: Apr. 21, 2023

(65) Prior Publication Data

US 2023/0248305 A1   Aug. 10, 2023

Related U.S. Application Data

(63) Continuation of application No. 17/692,244, filed on Mar. 11, 2022, now Pat. No. 11,660,048, which is a
(Continued)

(30) Foreign Application Priority Data

Aug. 19, 2020  (KR) .................. 10-2020-0103633
Nov. 4, 2020   (KR) .................. 10-2020-0146394
(Continued)

(51) Int. Cl.
*A61B 5/00*       (2006.01)
*G06F 18/214*    (2023.01)
(Continued)

(52) U.S. Cl.
CPC ........ *A61B 5/4833* (2013.01); *G06F 18/2148* (2023.01); *G06N 20/00* (2019.01);
(Continued)

(58) Field of Classification Search
CPC .......... A61B 5/4833; A61B 2560/0242; A61B 2562/0219; A61B 5/002; A61B 5/7285;
(Continued)

(56) References Cited

U.S. PATENT DOCUMENTS 10,025,908 B1 *  7/2018  Orellano ................ G16H 40/67
2015/0215443 A1   7/2015  Heo et al.
(Continued)

FOREIGN PATENT DOCUMENTS

JP   2004-280376 A   10/2004
JP   2015-126451 A    7/2015
(Continued)

OTHER PUBLICATIONS

International Search Report of PCT/KR2019/001118 dated May 8, 2019 from Korean Intellectual Property Office.
(Continued)

*Primary Examiner* — Dhaval V Patel
(74) *Attorney, Agent, or Firm* — Revolution IP, PLLC

(57) ABSTRACT

A monitoring system for obtaining a video related to medication adherence of a user, includes: a wireless communication device comprising a motion sensor, an ambient light sensor, a first transceiver transmitting data to an external device, and a first controller configured to control the motion sensor, the ambient light sensor, and the first transceiver, the wireless communication device having an attaching portion for being attached to an object containing a medication; and a wearable device including a camera, a second transceiver receiving a signal from the first transceiver, and a second controller configured to obtain video data through the camera based on the signal received through the second transceiver.

14 Claims, 45 Drawing Sheets

Related U.S. Application Data continuation of application No. 17/358,116, filed on Jun. 25, 2021, now Pat. No. 11,304,656.

(30) Foreign Application Priority Data

| Jan. 4, 2021 | (KR) | .................. 10-2021-0000496 |
| Mar. 26, 2021 | (KR) | .................. 10-2021-0039621 |

(51) Int. Cl.

| G06N 20/00 | (2019.01) |
| G06T 7/20 | (2017.01) |
| G06T 7/246 | (2017.01) |
| G06V 10/94 | (2022.01) |
| G06V 20/40 | (2022.01) |
| G06V 40/20 | (2022.01) |
| G08C 17/02 | (2006.01) |
| G16H 20/10 | (2018.01) |
| G16H 40/63 | (2018.01) |
| G16H 50/20 | (2018.01) |
| H04N 5/765 | (2006.01) |
| H04W 76/10 | (2018.01) |

(52) U.S. Cl.
CPC ............... *G06T 7/20* (2013.01); *G06T 7/251* (2017.01); *G06V 10/95* (2022.01); *G06V 20/41* (2022.01); *G06V 40/20* (2022.01); *G08C 17/02* (2013.01); *G16H 20/10* (2018.01); *G16H 40/63* (2018.01); *G16H 50/20* (2018.01); *H04N 5/765* (2013.01); *H04W 76/10* (2018.02); *G06T 2207/10016* (2013.01); *G06T 2207/20081* (2013.01); *G06T 2207/30196* (2013.01); *G06V 2201/03* (2022.01)

(58) Field of Classification Search
CPC ..... A61B 5/0077; A61B 5/681; A61B 5/6824; G06F 18/2148; G06F 1/163; G06N 20/00; G06N 3/08; G06N 3/045; G06N 3/044; G06N 3/047; G06T 7/20; G06T 7/251; G06T 2207/10016; G06T 2207/20081; G06T 2207/30196; G06V 10/95; G06V 20/41; G06V 40/20; G06V 2201/03; G06V 10/17; G06V 10/82; G06V 20/66; G08C 17/02; G16H 20/10; G16H 40/63; G16H 50/20; G16H 70/40; G16H 20/13; G16H 40/67; G16H 50/30; H04N 5/765; H04N 23/661; H04N 5/77; H04N 23/65; H04N 7/18; H04N 23/57; H04W 76/10; H04W 64/006

See application file for complete search history.

(56) References Cited

U.S. PATENT DOCUMENTS

| 2015/0216413 | A1 | 8/2015 | Soyao |
| 2015/0363570 | A1 | 12/2015 | Hanina et al. |
| 2016/0027284 | A1 | 1/2016 | Kamp et al. |
| 2016/0287166 | A1 | 10/2016 | Tran |
| 2016/0306932 | A1 | 10/2016 | Fateh et al. |
| 2016/0354283 | A1* | 12/2016 | Cho .......... A61J 7/049 |
| 2017/0004283 | A1* | 1/2017 | Lewis .......... G16H 10/60 |
| 2017/0111565 | A1 | 4/2017 | Shibahara et al. |
| 2018/0132783 | A1* | 5/2018 | Wang .......... A61B 5/6803 |
| 2019/0065970 | A1 | 2/2019 | Bonutti et al. |
| 2019/0385717 | A1 | 12/2019 | Guan et al. |
| 2021/0058590 | A1 | 2/2021 | Lee |

FOREIGN PATENT DOCUMENTS

| JP | 2016-091567 A | 5/2016 |
| JP | 2019-213886 A | 12/2019 |
| KR | 10-2011-0070824 A | 6/2011 |
| KR | 10-2015-0088599 A | 8/2015 |
| KR | 10-2016-0008448 A | 1/2016 |
| KR | 10-2016-0099435 A | 8/2016 |
| KR | 10-2016-0104288 A | 9/2016 |
| KR | 10-2016-0108051 A | 9/2016 |
| KR | 10-2016-0120131 A | 10/2016 |
| KR | 10-2017-0054861 A | 5/2017 |
| KR | 10-2017-0084657 A | 7/2017 |
| KR | 10-2017-0112704 A | 10/2017 |
| KR | 10-1798890 B1 | 11/2017 |
| KR | 10-2018-0028701 A | 3/2018 |
| KR | 10-2018-0054453 A | 5/2018 |
| KR | 10-2018-0084576 A | 7/2018 |
| KR | 10-1949102 B1 | 2/2019 |
| KR | 10-2019-0067686 A | 6/2019 |
| KR | 10-2019-0125143 A | 11/2019 |
| KR | 10-2019-0126773 A | 11/2019 |
| KR | 10-2020-0080047 A | 7/2020 |

OTHER PUBLICATIONS

Written opinion of PCT/KR2019/001118 dated May 8, 2019 from Korean Intellectual Property Office.
International Search Report of PCT/KR2020/006008 dated Aug. 24, 2020 from Korean Intellectual Property Office.
Written opinion of PCT/KR2020/006008 dated Aug. 24, 2020 from Korean Intellectual Property Office.
Office Action of KR Application No. 10-2019-7023063 dated Feb. 6, 2020 from Korean Intellectual Property Office.
Office Action of KR Application No. 10-2019-7023063 dated Apr. 17, 2020 from Korean Intellectual Property Office.
Office Action of KR Application No. 10-2019-7023063 dated Sep. 1, 2020 from Korean Intellectual Property Office.
Notice of Allowance of KR Application No. 10-2019-7023063 dated Sep. 28, 2020 from Korean Intellectual Property Office.
Office Action of KR Application No. 10-2020-7029786 dated Feb. 5, 2021 from Korean Intellectual Property Office.
Office Action of KR Application No. 10-2021-0040855 dated Jun. 14, 2021 from Korean Intellectual Property Office.
Office Action of KR Application No. 10-2021-0039622 dated Jun. 17, 2021 from Korean Intellectual Property Office.
Office Action of KR Application No. 10-2021-0040853 dated Jun. 23, 2021 from Korean Intellectual Property Office.
Office Action of KR Application No. 10-2021-0040854 dated Jun. 23, 2021 from Korean Intellectual Property Office.
Office Action of Korean Patent Application No. 10-2020-7013576 dated Jun. 30, 2021.
Non-Final Office Action of U.S. Appl. No. 17/356,528 dated Oct. 13, 2021.
Non-Final Office Action of U.S. Appl. No. 17/051,436 dated Dec. 17, 2021.
Written Opinion of PCT/KR2021/011033 dated Dec. 7, 2021.
International Search Report of PCT/KR2021/011057 dated Dec. 7, 2021.
Written Opinion of PCT/KR2021/011057 dated Dec. 7, 2021.
Non-Final Office Action of U.S. Appl. No. 17/518,615 dated Jan. 13, 2022.
Office Action of KR Application No. 10-2021-0186342 dated Jan. 19, 2022.
Non-Final Office Action of U.S. Appl. No. 17/356,528 dated Jan. 26, 2022.
A wearable sensor system for medication adherence prediction by Haik Kalantariana (Year: 2016).
Non-Final Office Action of U.S. Appl. No. 17/051,436 dated Dec. 7, 2021.
International Search Report of PCT/KR2021/011033 dated Dec. 7, 2021.

(56) References Cited

OTHER PUBLICATIONS

Office Action of KR Patent Application No. 10-2022-0169561 dated Jan. 17, 2023.

* cited by examiner

FIG. 21

| PLACE | RSSI MAXIMUM VALUE (dBm) | RSSI MINIMUM VALUE (dBm) |
|---|---|---|
| IN ELEVATOR | -58 | -72 |
| ON SUBWAY ESCALATOR | -62 | -80 |
| IN SUBWAY OR BUS | -58 | -66 |
| IN TV DRAWER | -58 | -66 |
| IN BED CABINET | -54 | -66 |
| IN OFFICE | -56 | -72 |

※ DISTANCE BETWEEN WIRELESS COMMUNICATION DEVICE AND WEARABLE DEVICE: 10~70cm

FIG. 35
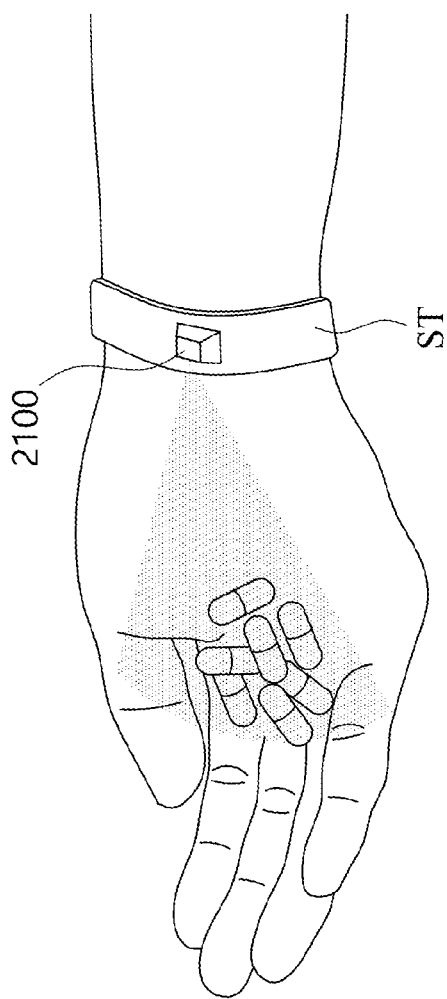
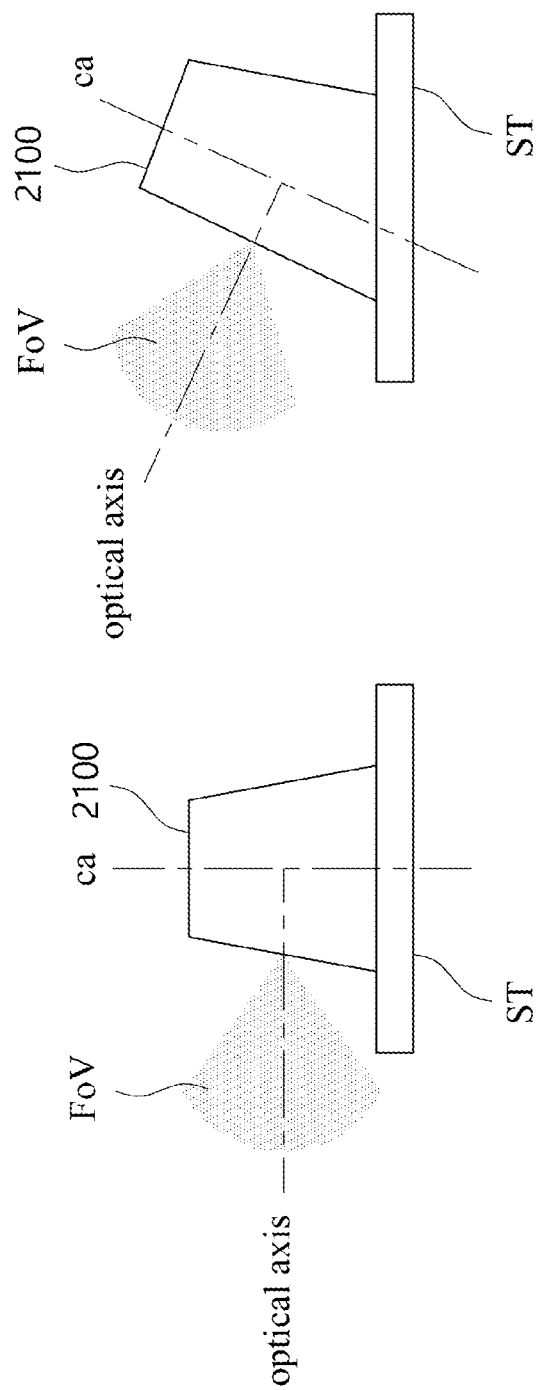

FIG. 41

| LOGO < | PARTICIPANT | | |
|---|---|---|---|
| DASHBOARD | PROJECT NAME | | |
| PROJECT | START PERIOD | END PERIOD | Code |
| PARTICIPANT | PURPOSE | | |
| | DESCRIPTIONS | | |
| | TARGET DISEASE | | |
| | DISEASE DESCRIPTIONS | | |
| | NAME OF MEDICATION | ⊕ B1 | NUMBER OF PARTICIPANTS |
| | QUALIFICATION | | DISQUALIFICATION |
| | CAUTIONS | | |

| PARTICIPANT | | | | | | | | | |
|---|---|---|---|---|---|---|---|---|---|
| RANDOM NUMBER | GENDER | AGE | TAKING MEDICINE | EMOTION | SIDE EFFECTS | PAIN | PARTICIPATING DATE | STATUS | VIEW |
| RN000061 | Female | 56 | 0% | 0% | 0 | 0 | 2020-09-23 | ☐ | ≡ |
| RANDOM NUMBER | GENDER | AGE | TAKING MEDICINE | EMOTION | SIDE EFFECTS | PAIN | PARTICIPATING DATE | STATUS | VIEW |
| RN000062 | Female | 54 | 0% | 0% | 0 | 0 | 2020-09-22 | ☐ | ≡ |
| RANDOM NUMBER | GENDER | AGE | TAKING MEDICINE | EMOTION | SIDE EFFECTS | PAIN | PARTICIPATING DATE | STATUS | VIEW |
| RN000045 | Male | 38 | 4% | 0% | 0 | 0 | 2020-09-13 | ■ | ≡ |
| RANDOM NUMBER | GENDER | AGE | TAKING MEDICINE | EMOTION | SIDE EFFECTS | PAIN | PARTICIPATING DATE | STATUS | VIEW |

FIG. 45

WEARABLE DEVICE FOR MEDICATION ADHERENCE MONITORING

CROSS-REFERENCE TO RELATED APPLICATION

This application is a Continuation Application of U.S. patent application Ser. No. 17/692,244 filed on Mar. 11, 2022 under 35 U.S.C. § 120, which is a Continuation Application of U.S. patent application Ser. No. 17/358,116 filed on Jun. 25, 2021 under 35 U.S.C. § 120, which claims priority to and the benefit of Korean Patent Application No. 10-2020-0103633, filed on Aug. 19, 2020, Korean Patent Application No. 10-2020-0146394, filed on Nov. 4, 2020, and Korean Patent Application No. 10-2021-0039621, filed on Mar. 26, 2021, the disclosure of which are incorporated herein by reference in their entirety.

BACKGROUND

Field of the Invention

The present invention relates to a medication adherence monitoring system and a device using the same, and more particularly, to a system for confirming whether a user performs medication adherence or uses a device related to the medication adherence.

Discussion of Related Art

Healthcare based on medical treatment and medical science has been receiving constant attention from the past, and as the life expectancy has increased with the recent development of medical technology, interest in healthcare has been further increased. Such healthcare should be performed regularly by the user himself or herself in daily life, such as taking prescribed medications in daily life, periodically injecting medications into his or her body, or measuring health indicators using medical devices.

In order to improve effects of the above-described healthcare, it is necessary to induce the user's actions related to the healthcare or impart coercion. To this end, there is a need for a monitoring system that detects a user's motion related to healthcare in daily life and determines whether the healthcare is sufficiently performed.

Meanwhile, in the past, in monitoring user's actions related to the healthcare, the user's actions are required, such as an action of driving a monitoring device before medication adherence or an action of recording his or her own actions. Accordingly, when the user forgets his or her own actions, there is a problem in that information about the healthcare is not collected.

Therefore, in consideration of the user's convenience and the accuracy of healthcare, it is necessary to develop a system that automatically monitors actions related to healthcare in daily life without user's actions.

SUMMARY OF THE INVENTION

The present invention is directed to providing a monitoring system that automatically monitors a user's motion related to healthcare in daily lives.

The present invention is also directed to providing a monitoring system that, when a user performs medication adherence, detects the user' motion, captures an image or video related to the medication adherence of the user, analyzes the captured image or captured video, and determines whether the user performs the medication adherence.

The present invention is also directed to providing a wireless communication device that detects a user's action and generates a signal for the initiation of shooting a video related to medication adherence of the user.

The present invention is also directed to providing a wearable device that may be worn on at least a portion of a user's body and captures an image related to medication adherence of the user when receiving a signal for the start of image capturing.

The present invention is also directed to providing a wearable device that is properly designed to have a field of view which can include interesting objects, such as a palm, a mouth, or a medicine etc., when being worn by the user while the user takes medication.

Objects to be solved by the present invention are not limited to the above-described objects and other unmentioned objects may be clearly understood by those skilled in the art from this specification and the accompanying drawings.

According to one embodiment of the present disclosure, there can be provided a monitoring system for obtaining a video related to medication adherence of a user, the monitoring system comprising: a wireless communication device comprising a motion sensor, an ambient light sensor, a first transceiver transmitting data to an external device, and a first controller configured to control the motion sensor, the ambient light sensor, and the first transceiver, the wireless communication device having an attaching portion for being attached to an object containing a medication; a wearable device comprising a camera, a second transceiver receiving a signal from the first transceiver, and a second controller configured to obtain video data through the camera based on the signal received through the second transceiver; wherein the first controller of the wireless communication device is configured to: obtain, by using the motion sensor, a motion value corresponding to a movement of the object, obtain, by using the ambient light sensor, an ambient light value corresponding to ambient light of the object, generate activation data for inducing activation of the camera of the wearable device, based on the motion value and the ambient light value, and provide, by using the first transceiver, the activation data to the wearable device, and wherein the second controller of the wearable device obtains the video data by activating the camera based on the received activation data generated from the wireless communication device based on the movement and the ambient light of the object.

According to another embodiment of the present disclosure, there can be provided the wireless communication device configured to transmit data to an external device for inducing the external device including a camera to initiate taking a video, the wireless communication device comprising: a transceiver; a motion sensor; an ambient light sensor; a controller; a housing having an inner space where the transceiver, the motion sensor, the ambient light sensor, and the controller are placed; and an attachment region implemented outside of the housing, the wireless communication device configured to attach to an object containing medication through the attachment region; wherein a controller is configured to: transmit the data to the external device through the transceiver; obtain a motion value reflecting a movement of the object by using the motion sensor, obtain an ambient light value reflecting an ambient environment of the object by using the ambient light sensor, and provide activation data based on the motion value and the ambient light value, the activation data indicating the camera of the external device to be activated, wherein the controller is further configured to: determine whether the ambient light value is equal to or greater than an ambient light threshold value when the motion value is equal to or greater than a motion threshold value, and generate the activation data and provide the activation data to the external device when the ambient light value is equal to or greater than the ambient light threshold value, and wherein the controller does not generate the activation data when the ambient light value is less than the ambient light threshold value even though the motion value is equal to or greater than the motion threshold value.

According to the embodiments of the present invention, the user's healthcare is automatically monitored to minimize user intervention, and thus user convenience can be improved.

According to the embodiments of the present invention, by providing a wearable device, which is worn on a user's body and captures an image related to medication adherence of the user, the user's healthcare can be easily monitored in daily life, and thus usability of the wearable device can be increased.

According to the embodiments of the present invention, by providing a wireless communication device that detects a user' motion to generate a signal for capturing an image related to medication adherence of the user, the medication adherence of the user can be monitored more accurately and regularly.

According to an embodiment of the present invention, by analyzing a video related to medication adherence using an artificial neural network, the accuracy of determining whether the medication adherence is performed can be improved.

Effects of the present invention are not limited to the above-described effects and other unmentioned effects may be clearly understood by those skilled in the art from this specification and the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 21 is a diagram illustrating the strength of a signal received by a wearable device according to a place where a wireless communication device according to an embodiment of the present invention is located.

FIG. 35 is a diagram illustrating a field of view of a camera module according to a slope of the camera module according to an embodiment of the present invention.

Figure 42:
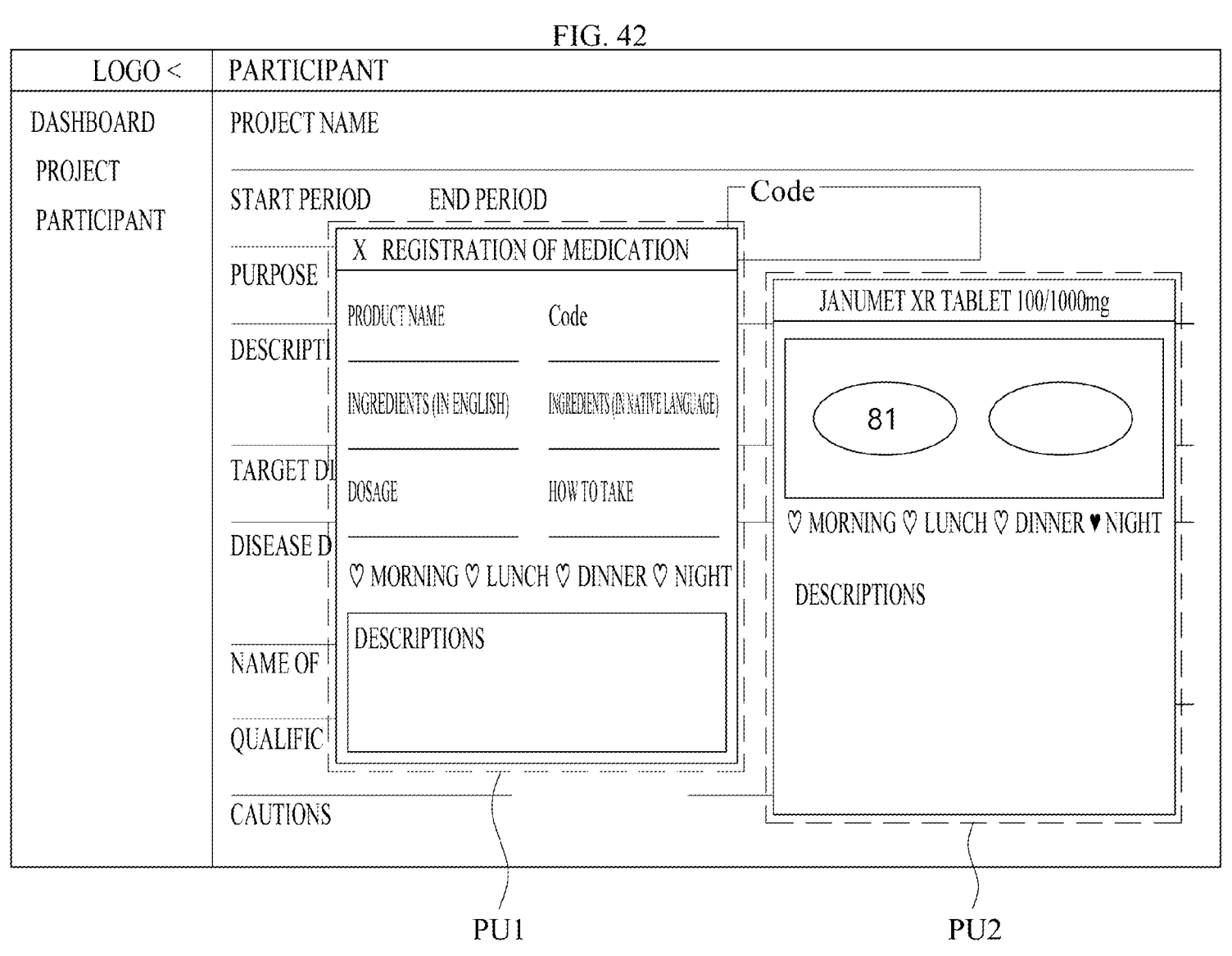

FIGS. 40 to 44 are diagrams illustrating a management service provided to medical personnel, a guardian, or a manager according to an embodiment of the present invention.

FIG. 45 is a diagram illustrating a management service provided to a user according to an embodiment of the present invention.

DETAILED DESCRIPTION OF EXEMPLARY EMBODIMENTS

Figure 1:
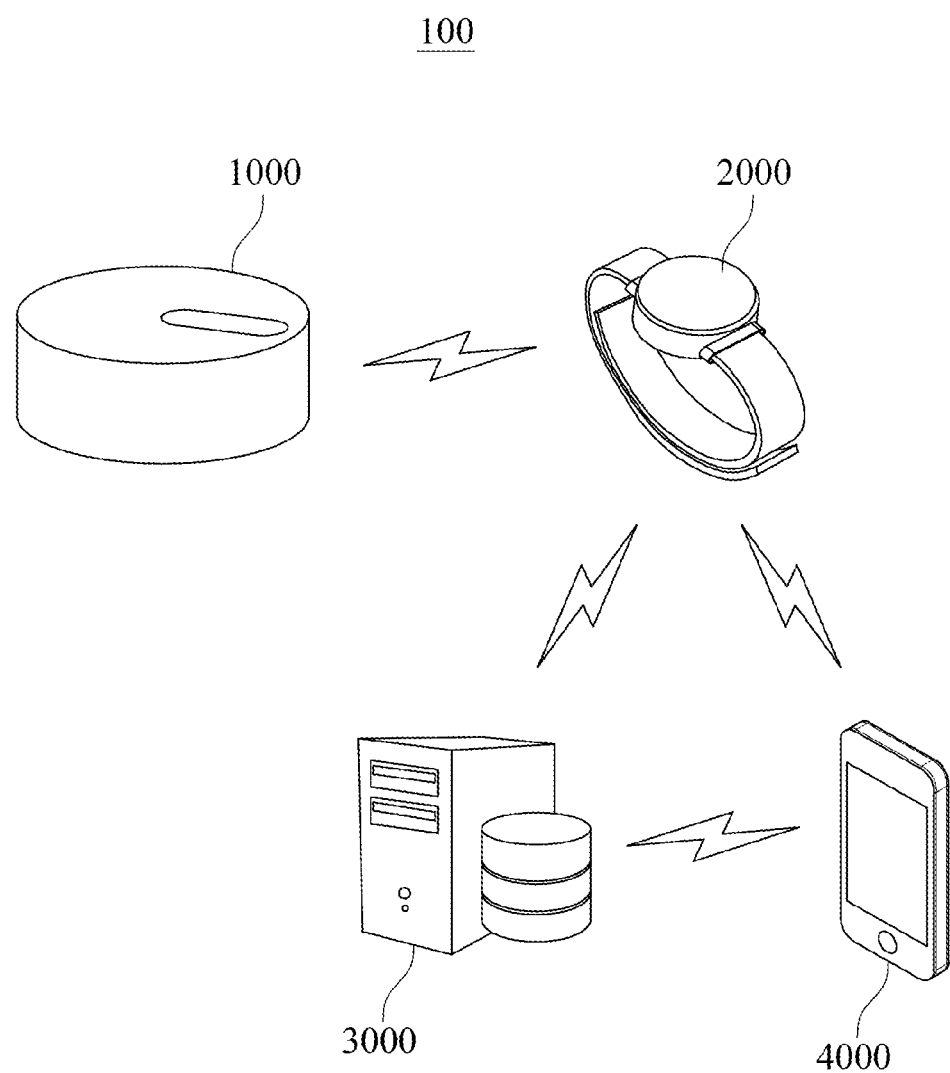
FIG. 1 is a diagram illustrating a medication adherence monitoring system according to an embodiment of the present invention.

Objects, features, and advantages of the present invention will become more apparent from the following detailed description related to the accompanying drawings. However, while the present invention may have various modifications and alternative forms, specific embodiments thereof are shown by way of example in the drawings and will be described herein in detail.

In the drawings, the thicknesses of layers or regions are exaggerated for clarity of description. Further, when an element or layer is referred to as being disposed "on" another element or layer, it includes a case in which the element or layer is formed directly on another element or layer and a case in which still another element or layer is interposed between the element or layer and another element. Like reference numerals principally refer to like elements throughout the specification. Further, elements having the same function within the scope of the same concept shown in the drawings of each embodiment will be described using the same reference numerals, and redundant descriptions thereof will be omitted.

When it is determined that detailed descriptions of well-known functions or configurations related to the present invention may unnecessarily obscure the gist of the present invention, detailed descriptions thereof will be omitted. Further, the numbers (for example, first, and second) used in description of the specification are used only to distinguish one element from another element.

Further, a suffix "module," "unit," or "portion" of an element used in the following embodiments is assigned or incorporated for convenience of specification description, and the suffix itself does not have a distinguished meaning or function.

In the following embodiments, the singular forms "a," "an," and "the" are intended to include the plural forms as well, unless the context clearly indicates otherwise.

In the following embodiments, it will be further understood that the terms "comprise" and/or "comprising" used herein specify the presence of stated features or elements but do not preclude the presence or addition of one or more other features or elements.

In the following embodiments, the terms "at least one of A and B" or "at least one of A or B" could be understood as "A, B or a combination of A and B". In other words, the terms might indicate "one selected among A, B and A&B".

Sizes of elements in the drawings may be exaggerated for convenience of description. In other words, since sizes and thicknesses of elements in the drawings are arbitrarily illustrated for convenience of description, the present invention is not limited thereto.

When a certain embodiment may be implemented differently, a specific process order may be performed differently from the described order. For example, two consecutively described processes may be performed substantially at the same time or performed in an order opposite to the described order.

In the following embodiments, when a film, region, or element is referred to as being "connected to" another film, region, or element, the film, region, or element may be directly connected to another film, region, or component or may be indirectly connected to another film, region, or component with still another film, region, or element interposed therebetween.

For example, in this specification, when a film, region, or element is referred to as being "electrically connected to" another film, region, or component, the film, region, or element may be directly electrically connected to another film, region, or component or may be indirectly electrically connected to another film, region, or component with still another film, region, or element interposed therebetween.

According to one embodiment of the present disclosure, there can be provided a monitoring system for obtaining a video related to medication adherence of a user, the monitoring system comprising: a wireless communication device comprising a motion sensor, an ambient light sensor, a first transceiver transmitting data to an external device, and a first controller configured to control the motion sensor, the ambient light sensor, and the first transceiver, the wireless communication device having an attaching portion for being attached to an object containing a medication; a wearable device comprising a camera, a second transceiver receiving a signal from the first transceiver, and a second controller configured to obtain video data through the camera based on the signal received through the second transceiver; wherein the first controller of the wireless communication device is configured to: obtain, by using the motion sensor, a motion value corresponding to a movement of the object, obtain, by using the ambient light sensor, an ambient light value corresponding to ambient light of the object, generate activation data for inducing activation of the camera of the wearable device, based on the motion value and the ambient light value, and provide, by using the first transceiver, the activation data to the wearable device, and wherein the second controller of the wearable device obtains the video data by activating the camera based on the received activation data generated from the wireless communication device based on the movement and the ambient light of the object.

In some embodiments, the wearable device initiates a pairing process when receiving an advertising signal from the wireless communication device, In some embodiments, the wearable device and the wireless communication device are paired as they share link data; and the first controller provides the activation data to the second controller after the wearable device and the wireless communication device are paired.

In some embodiments, the wireless communication device is configured to operate in a sleep state or a standby state, the first controller does not obtain a sensor value from the motion sensor and the ambient sensor in the sleep state and the first controller obtains the sensor value from at least one of the motion sensor or the ambient light sensor in the standby state, and the wireless communication device operates from the sleep state to the standby state when being paired with the wearable device.

In some embodiments, the first controller obtains the motion value by using the motion sensor in the standby state.

In some embodiments, the wireless communication device operates in the sleep state, the standby state, or the awake state, the first controller, in the awake state, generates the activation data and provides the activation data to the second controller when the ambient light value obtained by the ambient light sensor is equal to or greater than an ambient light threshold value, and the first controller controls the wireless communication device to operate in the awake state when the first controller determines that the motion value obtained in the standby state is equal to or greater than a motion threshold value.

In some embodiments, the wireless communication device is configured to operate in a sleep state or a standby state, wherein the motion sensor obtains the motion value per a first time gap in the sleep state, and wherein the motion sensor obtains the motion value per a second time gap, which is shorter than the first time gap, in the standby state.

In some embodiments, the wireless communication device is configured to operate in a sleep state or a standby state, wherein the ambient light sensor obtains the ambient light value per a first time gap in the sleep state, and wherein the ambient light sensor obtains the ambient light value per a second time gap, which is shorter than the first time gap, in the standby state.

In some embodiments, the first controller generates the activation data when the motion value obtained by using the motion sensor is equal to or greater than a predetermined motion threshold value and the ambient light value obtained by using the ambient light sensor is equal to or greater than a predetermined ambient light threshold value.

In some embodiments, the activation data is included in an advertising signal that the wireless communication device transmits to the wearable device.

In some embodiments, the first controller provides unique identification data of the wireless communication device to the second controller, wherein an imaging time is set based on the unique identification data of the wireless communication device, and wherein the second controller activates the camera based on the activation data to take a video for an imaging time.

In some embodiments, a signal that the second controller receives from the first transceiver includes a first signal received before a first time point when the wireless communication device and the wearable device are paired and a second signal received after the first time point, and the second controller obtains the activation data from the second signal.

In some embodiments, the second controller obtains the unique identification data from the second signal.

In some embodiments, the monitoring system further comprises a server obtaining the video data from the wearable device and determining whether the user has taken medication by using the video data.

In some embodiments, the wearable device activates the camera for an imaging time and transmits the video data to the server after a predetermined waiting time from when the camera is deactivated.

In some embodiments, the wearable device takes a video for a predetermined imaging time when obtaining a first activation data from the wireless communication device, wherein the wearable device further takes a video for an extra time when obtaining a second activation data from the wireless communication device during the imaging time, and wherein the extra time is shorter than the imaging time.

In some embodiments, the wearable device includes an output module and provides an alarm to the user through the output module while the video data is obtained as the camera being activated.

In some embodiments, the server determines whether the user has taken medication by using a medication monitoring model trained as outputting data related to whether the user has taken medication when the video data is inputted.

In some embodiments, the medication monitoring model includes: a detection model receiving image frames of the video data as input and outputting a probability value indicating whether the object related to the medication adherence is included in the video data, and a confirmation model receiving input data reflecting the probability value and outputting a class value indicating whether the user has taken the medication.

According to another embodiment of the present disclosure, there can be provided the wireless communication device configured to transmit data to an external device for inducing the external device including a camera to initiate taking a video, the wireless communication device comprising: a transceiver; a motion sensor; an ambient light sensor; a controller; a housing having an inner space where the transceiver, the motion sensor, the ambient light sensor, and the controller are placed; and an attachment region implemented outside of the housing, the wireless communication device configured to attach to an object containing medication through the attachment region; wherein a controller is configured to: transmit the data to the external device through the transceiver; obtain a motion value reflecting a movement of the object by using the motion sensor, obtain an ambient light value reflecting an ambient environment of the object by using the ambient light sensor, and provide activation data based on the motion value and the ambient light value, the activation data indicating the camera of the external device to be activated, wherein the controller is further configured to: determine whether the ambient light value is equal to or greater than an ambient light threshold value when the motion value is equal to or greater than a motion threshold value, and generate the activation data and provide the activation data to the external device when the ambient light value is equal to or greater than the ambient light threshold value, and wherein the controller does not generate the activation data when the ambient light value is less than the ambient light threshold value even though the motion value is equal to or greater than the motion threshold value.

In some embodiments, the controller and the motion sensor communicate in a full duplex manner, and the controller and the ambient light sensor communicate in a half duplex manner.

In some embodiments, the wireless communication device further comprises: a light sensing region for the ambient light sensor receiving light, the light sensing region not being overlapped with the attachment region.

In some embodiments, the housing has a shape of cylinder, wherein the attachment region is located on a lower surface of the housing while the light sensing region is located on an upper surface of the housing.

According to still another embodiment of the present disclosure, there can be provided, a wearable device for obtaining a video related to medication adherence of a user, the wearable device comprising: a camera; a transceiver; and a controller configured to control the camera and the transceiver; wherein the controller is configured to: receive activation data for inducing activation of the camera from an external device, obtain a RSSI (Received Signal Strength Indication) value of a signal received from the external device, the RSSI value reflecting at least surrounding environment of the wearable device and a distance between the wearable device and the external device, obtain video data related to the medication adherence of the user by activating the camera based on the activation data and the RSSI value, wherein the controller does not activate the camera when the RSSI value is out of a predetermined range of signal strength, even though the activation data is received.

In some embodiments, the controller is further configured to obtain a data packet including the activation data through the signal received from the external device.

In some embodiments, the signal includes a data packet signal corresponding to the data packet including the activation data, and the RSSI value corresponds to signal strength of the data packet signal.

In some embodiments, the controller is further configured to obtain a first RSSI value of a first signal received from the external device at a first time point and a second RSSI value of a second signal received from the external device at a second time point, and the controller does not activate the camera if the first RSSI value or the second RSSI value is out of the predetermined range of signal strength.

In some embodiments, a time point at which the data packet signal is received is between the first time point and the second time point.

In some embodiments, the predetermined range of signal strength is above −100 dBm.

In some embodiments, the predetermined range of signal strength is above −80 dBm.

In some embodiments, the predetermined range of signal strength is above a standard value, and the standard value is set between −120 dBm and −60 dBm.

In some embodiments, the standard value is set between −100 dBm and −80 dBm.

In some embodiments, the predetermined range of signal strength is above a standard value, and the standard value is set based on signal strength of a signal that the controller received from the external device when a distance between the wearable device and the external device is within a predetermined range of distance.

In some embodiments, the predetermined range of distance is within 100 cm.

In some embodiments, the predetermined range of distance is within 70 cm.

In some embodiments, the predetermined range of distance is within 20 cm.

According to still another embodiment of the present disclosure, there can be provided, a monitoring system for obtaining a video related to medication adherence of a user, the monitoring system comprising:

a wireless communication device including a motion sensor, a first transceiver, and a first controller transmitting data to external device through the first transceiver; and a wearable device including a camera, a second transceiver receiving a signal including data from the wireless communication device, and a second controller configured to control the camera and the second transceiver;

wherein the first controller is configured to:

obtain activation data for instructing activation of the camera of the wearable device by using at least a motion value obtained through the motion sensor, the motion value reflecting a movement of the wireless communication device, and transmit the activation data to the wearable device through the second transceiver, wherein the second controller is configured to:

activate the camera based on the activation data received from the wireless communication device, determine whether signal strength of the signal received from the wireless communication device is within a predetermined range of signal strength, and activate the camera when the signal strength of the signal is within the predetermined range of signal strength and not activate the camera when the signal strength of the signal is out of the predetermined range of signal strength.

According to still another embodiment of the present disclosure, there can be provided a wearable device worn on a wrist of a user, the wearable device comprising: a main body having an inner space surrounded by at least a top side, a bottom side, a first side, a second side, a third side and a fourth side, the first side and the second side facing each other, the third side and the fourth side facing each other, wherein the main body has a length defined by the first side and the second side, and a width defined by the third side and the fourth side; a first strap having a first end coupled to the first side of the main body and a second end including a first connection portion; a second strap having a third end coupled to the second side of the main body and a second connection portion for interacting with the first connection portion of the first strap, wherein a length of the second strap is shorter than a length of the first strap; a camera module disposed on the first strap; wherein the second strap further includes a fixing portion where at least part of the second connection portion is attachable such that the second strap does not cover the camera module, wherein a field of view of the camera module heading toward a direction along the width of the main body and wherein a length between the camera module and the first end is longer than a length between the camera module and the first connection portion such that the field of view includes at least part of a palm of a user.

In some embodiments, the wearable device of further comprises a display unit exposed through the top side, a controller disposed in the inner space and configured to control the display unit output the information, and an electric connection line electrically connecting the controller and the camera module.

In some embodiments, the electric connection line arranged between the camera module and the first end of the first strap, the electric connection line disposed inside the first strap such that the electric connection line is hidden by the first strap.

In some embodiments, the wearable device further comprises a battery disposed under the display unit, and a power supply line electrically connecting the camera module and the battery.

In some embodiments, the strap is composed of a top surface and a bottom surface, and the camera module is installed inside the strap while a lens of the camera module is positioned between the top surface and the bottom surface.

In some embodiments, the camera module further including a lens, wherein an optical axis of the lens has an acute angle respect to a surface of the first strap where the camera module is disposed.

In some embodiments, the angle between the optical axis and the surface of first strap is between 15 to 75 degrees.

In some embodiments, the angle between the optical axis and the surface of first strap is between 30 to 60 degrees.

In some embodiments, the present disclosure provides a wearable device worn on a wrist of a user, the wearable device comprising: a main body having an inner space surrounded by at least a top side, a bottom side, a first side, a second side, a third side and a fourth side, the first side and the second side facing each other, the third side and the fourth side facing each other; a first strap having a first end coupled to the first side of the main body, and a second end including a first connection portion; a second strap having a third end coupled to the second side of the main body, and a second connection portion for coupling to the first connection portion of the first strap; a camera module disposed on a top surface of the first strap having a longer length than the second strap; wherein the first strap further includes a fixing portion where at least part of the second connection portion is coupled, wherein the fixing portion is disposed on a bottom surface of the first strap such that the second strap does not overlay the camera module, wherein a field of view of the camera module heading toward a width direction of the main body when the main body has a length defined by the first side and the second side, and a width defined by the third side and the fourth side, and wherein a length between the camera module and the first end is longer than a length between the camera module and the first connection portion such that the field of view includes at least part of a palm of a user.

This specification relates to a medication adherence monitoring system, and more specifically, to a system and method, in which, when a user performs medication adherence for the purpose of diagnosis, treatment, or prevention of disease, or health promotion, whether the user performs the medication adherence is monitored, and a device used in the system and method.

In this specification the term "medication" may refer to a substance used for diagnosis, alleviation, treatment, action, or prevention of disease, or health promotion. The term "medication" may refer to a chemical composition itself corresponding to a specific disease or may refer to a substance obtained by processing such a chemical composition. For example, the medication may be present in various formulations such as a tablet form, a capsule form, a syrup form, or an applicable form.

The medication may be stored in a medication container. For example, the medication container may include a medication case, a medication bottle, a blister pack, an eyedropper, a portable medication case, a medication box, a medication bag, a medication calendar, a dispenser, or the like. Meanwhile, the medication may be stored in a medication delivery device according to usage thereof. For example, the medication delivery device may include an inhaler, a spray, a syringe, a patch, or the like. As described above, the medication container may refer to not only an object having a predetermined volume to accommodate a medication, but also an object including at least a portion capable of accommodating the medication.

In this specification, the term "adherence" may refer to a process in which a medication is introduced into the user's body. The medication adherence may be performed by various delivery systems such as an oral delivery system, a transdermal delivery system, an injectable delivery system, a closed-up delivery system, a mucosal administration type delivery system, and the like.

In this specification, the term "medication adherence" may refer to an action performed by the user who is intended to be monitored using a medication adherence monitoring system, or an action performed on the user.

For example, the medication adherence may include an action of taking a medication using the user's hand, an action of inhaling a medication through a device such as an inhaler, an action of injecting a medication into the body through a device such as a syringe, an action of applying a medication onto a portion of the body, an action of administering a medication to the user, an action of inhaling a medication by the user using an inhaler or the like, an action of injecting a medication into a portion of the user's body using a device such as a syringe, an action of applying a medication (ex. ointment, application, or cream etc.) onto a portion of the user's body, or the like. The medication adherence may be performed by the user serving as a subject or may be performed on the user by another person serving as a subject.

Hereinafter, the medication adherence is mainly described as being performed by the user, but the technological concept of the present invention is not limited thereto, and the medication adherence may also be performed on the user by medical personnel, a guardian, or a manager.

In this specification, the term "monitoring" may refer to a process of detecting actions related to medication adherence of the user and confirming whether the user performs the medication adherence. For example, the monitoring may include a process of collecting information about the medication adherence of the user and determining whether the user actually performs the medication adherence or whether the user performs the medication adherence according to the usage. Furthermore, the monitoring may include a process of managing or assisting the medication adherence of the user, such as inducing the medication adherence of the user on the basis of data on whether the user performs the medication adherence, or providing data for the medication adherence of the user to a manager who manages the user's condition. Here, the monitoring includes not only monitoring for a single user but also monitoring for multiple users.

Hereinafter, a medication adherence monitoring system and components thereof will be described with reference to FIG. 1.

FIG. 1 is a diagram illustrating a medication adherence monitoring system 100 according to an embodiment of the present invention.

Referring to FIG. 1, the medication adherence monitoring system 100 may include a wireless communication device 1000, a wearable device 2000, a server 3000, and a terminal device 4000.

The wireless communication device 1000 may serve to trigger image capturing of the wearable device 2000 in the medication adherence monitoring system 100. For example, the wireless communication device 1000 may provide specific data to the wearable device 2000, and the wearable device 2000 may obtain image data related to medication adherence of a user on the basis of the specific data received from the wireless communication device 1000. The triggering of the wireless communication device 1000 will be described in detail below.

The wireless communication device 1000 may obtain information about a medication container or a medication delivery device. For example, the wireless communication device 1000 may be attached to the medication container or the medication delivery device and may obtain a sensed value reflecting the movement of the medication container or medication delivery device or obtain a sensed value reflecting ambient light or illuminance using an embedded sensor therein. Here, the wireless communication device 1000 may determine whether the user starts the medication adherence on the basis of the sensed values obtained using the sensor.

The wireless communication device 1000 may transmit or receive signals or data to or from the wearable device 2000 through wireless communication. For example, the wearable device 2000 may receive data indicating the start of image capturing from the wireless communication device 1000.

The wearable device 2000 may collect data related to the medication adherence of the user. For example, the wearable device 2000 may capture an image using an embedded camera therein. Here, the wearable device 2000 may capture an image in response to the signal received from the wireless communication device 1000. In this case, when the wireless communication device 1000 detects the process of the medication adherence of the user and transmits the signal to the wearable device 2000, the wearable device 2000 may photograph the process of the medication adherence of the user so that image data related to the medication adherence of the user may be obtained.

The wearable device 2000 may be worn on at least a portion of a body of the user. For example, the wearable device 2000 may include a wrist band, a watch, a smart watch, or smart glasses. As another example, the wearable device 2000 may be implemented in the form of an accessory such as glasses, a ring, a necklace, or the like.

The wearable device 2000 may communicate with the wireless communication device 1000, the server 3000, or the terminal device 4000 to transmit or receive signals or data to or from the wireless communication device 1000, the server 3000, or the terminal device 4000. For example, the wearable device 2000 may transmit image data obtained by capturing an image to the server 3000 or the terminal device 4000.

The server 3000 may determine whether the user performs medication adherence. For example, the server 3000 may determine whether the user performs the medication adherence or may determine whether the user performs the medication adherence in an appropriate manner using the image data related to the medication adherence of the user.

The server 3000 may be composed of a plurality of servers classified according to functions thereof.

As an example, the server 3000 may include an analysis server for data analysis. The analysis server may analyze the data obtained from the wireless communication device 1000 or the wearable device 2000 to determine whether the user performs the medication adherence, as described above. The analysis server may provide a result of determining whether the user performs the medication adherence to the wireless communication device 1000 or the wearable device 2000.

As another example, the server 3000 may include a management server for data management. The management server may provide a platform, which is for collecting and sorting the data related to the medication adherence of the user to manage the medication adherence of the user, to a guardian, medical personnel, and/or a manager. Specifically, the management server may provide basic information, medical information, medication adherence information, etc. about the user, and the medical personnel, the manager, or the guardian who uses the management server may provide information or gives instructions to the user on the basis of the above-described information.

The server 3000 may communicate with the wearable device 2000 or the terminal device 4000 to transmit or receive data to or from the wearable device 2000 or the terminal device 4000. For example, the wearable device 2000 may receive data on whether the user performs the medication adherence from the server 3000.

The terminal device 4000 may provide information related to the medication adherence to the user or may induce the medication adherence of the user. For example, the terminal device 4000 may collect the data on whether the user performs the medication adherence to provide the data to the user or provide a notification to induce the medication adherence of the user.

The terminal device 4000 may refer to an electronic device that provides information to a user, a guardian, a manager, or medical personnel (hereinafter, referred to as a "user") related to medication adherence. For example, the terminal device 4000 may include mobile computing devices such as mobile phones and smart phones, laptop computers, desktop computers, tablet personal computers (PCs), notebook computers, wearable computers such as smart watches or head-mounted computers, and the like.

The terminal device 4000 may communicate with the wearable device 2000 or the server 3000 to transmit or receive signals or data to or from the wearable device 2000 or the server 3000.

Meanwhile, in the medication adherence monitoring system 100, any one of the wireless communication device 1000, the wearable device 2000, the server 3000, and the terminal device 4000 may be omitted. For example, in the medication adherence monitoring system 100, the terminal device 4000 may be omitted.

The components of the medication adherence monitoring system 100 may operate as follows.

For example, the wireless communication device 1000 may provide the data for the start of image capturing to the wearable device 2000, the wearable device 2000 may provide the image data to the server 3000, and the server 3000 may provide image analysis data or monitoring result data to the wearable device 2000 or the terminal device 4000.

As another example, the wireless communication device 1000 may provide the data for the start of image capturing to the wearable device 2000, the wearable device 2000 may provide the image data to the terminal device 4000, the terminal device 4000 may provide the image data obtained from the wearable device 2000 to the server 3000, and the server 3000 may provide the image analysis data or the monitoring result data to the wearable device 2000 or the terminal device 4000.

Meanwhile, the server 3000 may receive the data for the start of image capturing from the wireless communication device 1000 or receive data on whether the image is captured from the wearable device 2000 before obtaining the image data from the wearable device 2000. The server 3000 may receive the data for the start of image capturing or the data on whether the image is captured and determine in real time about duplicate medications or untaken medication, which will be described below.

Hereinafter, the image data obtained by the wearable device 2000 is described as being transmitted to the server 3000, but the technological concept of the present invention is not limited thereto.

Further, the function of any one component of the medication adherence monitoring system 100 may be performed by the function of another component. For example, the wearable device 2000 may analyze the image data to determine whether the user performs the medication adherence. In this case, the server 3000 may be omitted.

Hereinafter, each component of the medication adherence monitoring system 100 will be described more specifically.

Figure 2:
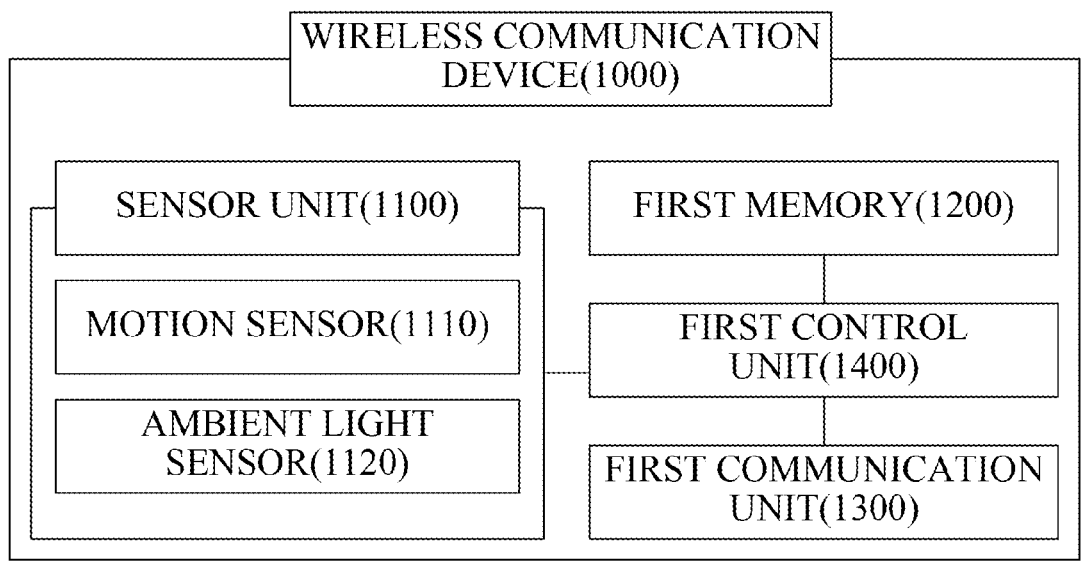
FIG. 2 is a diagram illustrating a wireless communication device according to an embodiment of the present invention.

FIG. 2 is a diagram illustrating a wireless communication device 1000 according to an embodiment of the present invention.

Referring to FIG. 2, the wireless communication device 1000 may include a sensor unit 1100, a first memory 1200, a first communication unit 1300, and a first control unit 1400.

The sensor unit 1100 may detect or recognize movement of the wireless communication device 1000 or an environment around the wireless communication device 1000.

The sensor unit 1100 may include a motion sensor 1110. The motion sensor 1110 may detect the movement of the wireless communication device 1000. For example, the motion sensor 1110 may detect a change in position, a change in acceleration, a change in inclination, or rotation of the wireless communication device 1000 to provide an electrical signal corresponding thereto to the first control unit 1400, and the first control unit 1400 may obtain an acceleration value, an angular velocity value, a geomagnetic value, or the like from the electrical signal.

Here, the motion sensor 1110 may be composed of an acceleration sensor, a gyro sensor, a geomagnetic sensor, an inertia measurement unit (IMU), or a combination thereof. As an example, the motion sensor 1110 may be composed of an acceleration sensor and a gyro sensor that are integrated on different circuit boards and individually controlled. As another example, the motion sensor 1110 may be configured as a six-axis sensor or a nine-axis sensor in which an acceleration sensor, a gyro sensor, a geomagnetic sensor, etc. are integrated on one circuit board and controlled together. As still another example, the motion sensor 1110 may be configured as a single sensor, such as a three-axis acceleration sensor, a three-axis gyro sensor, a three-axis geomagnetic sensor, or the like.

The sensor unit 1100 may include an ambient light sensor 1120. The ambient light sensor 1120 may detect ambient light of the wireless communication device 1000. For example, the ambient light sensor 1120 may provide an electrical signal corresponding to the ambient light of the wireless communication device 1000 to the first control unit 1400, and the first control unit 1400 may obtain an ambient light value from the electrical signal.

The sensor unit 1100 may be electrically connected to the first control unit 1400 to transmit or receive data to or from the first control unit 1400. When the sensor unit 1100 includes a plurality of sensors, the sensors may transmit or receive data to or from the first control unit 1400 in different ways. For example, the sensor unit 1100 and the first control unit 1400 may use a serial communication method, any one sensor of the sensor unit 1100 may transmit or receive the data to or from the first control unit 1400 in a half-duplex method in which one data line is used, and another sensor may transmit or receive the data to or from the first control unit 1400 in a full-duplex method in which two data lines are used. Specifically, when the sensor unit 1100 includes the motion sensor 1110 and the ambient light sensor 1120, the motion sensor 1110 may transmit or receive the data to or from the first control unit 1400 through Serial Peripheral Interface (SPI) communication, and the ambient light sensor 1120 may transmit or receive the data to or from the first control unit 1400 through Inter-Integrated Circuit (I²C) communication. In other words, the first control unit 1400 may transmit or receive the data in a manner that consumes relatively higher power but has a higher velocity than the motion sensor 1110 having a relatively high importance and may transmit or receive the data in a manner that has a relatively slower velocity but consumes less power than the ambient light sensor 1120 having a relatively low importance. As a result, performance of the wireless communication device 1000 and efficiency of a battery can be improved.

Meanwhile, when the sensor unit 1100 includes a plurality of sensors, the sensors may transmit or receive the data to or from the first control unit 1400 in the same manner. For example, the plurality of sensors included in the sensor unit 1100 may transmit or receive the data to or from the first control unit 1400 in a half-duplex method or a full-duplex method.

Meanwhile, the sensor unit 1100 may include another sensor, for example, an infrared sensor, a proximity sensor, or the like for detecting an approach of a user or another object, in addition to the motion sensor 1110 or the ambient light sensor 1120.

On the other hand, the sensor unit 1100 may further include at least one sensor control module that controls an operation of the sensor unit 1100. The sensor control module may be disposed to be in close contact with the sensors of the sensor unit 1100 to control the sensors by receiving electrical signals from the sensors or providing electrical signals to the sensors. For example, the sensor control module may allow the sensors of the sensor unit 1100 to operate in a low power mode or a normal mode which will be described below. In addition, for example, the sensor control module may obtain sensed values using the electrical signals obtained from the sensors of the sensor unit 1100 and provide the sensed values to the first control unit 1400. Here, the sensor control module may be implemented on the same board as the sensors of the sensor unit 1100 to control to the sensors or on a separate board from the sensors to transmit or receive the electrical signals to or from the sensors.

Meanwhile, in order to manage power consumption of the wireless communication device 1000, the sensor unit 1100 may be operated in the low power mode or the normal mode. As will be described below, the sensor unit 1100 may be operated in the low power mode, thereby reducing power consumed by the sensor unit 1100 and consequently improving the efficiency of the battery of the wireless communication device 1000.

The low power mode may refer to a mode having relatively low power consumption compared to the normal mode. The sensor unit 1100 may be operated in different ways in the normal mode and the low power mode, and power consumed for operation may be different in the normal mode and the low power mode. For example, the sensor unit 1100 may have a lower sensing frequency in the low power mode than in the normal mode. Specifically, the motion sensor 1110 may detect the movement of the wireless communication device 1000 at an interval of a longer period in the low power mode than in the normal mode, and the first control unit 1400 may obtain a motion value at an interval of a longer period in the low power mode than in the normal mode. The motion sensor 1110 may detect the movement of the wireless communication device 1000 at an interval of a shorter period in the normal mode than in the low power mode, and the first control unit 1400 may obtain a motion value at an interval of a shorter period in the normal mode than in the low power mode.

Similarly, the ambient light sensor 1120 may detect the ambient light of the wireless communication device 1000 at an interval of a longer period in the low power mode than in the normal mode, and the first control unit 1400 may obtain the ambient light value at an interval of a longer period in the low power mode than in the normal mode. The ambient light sensor 1120 may detect the ambient light of the wireless communication device 1000 at an interval of a shorter period in the normal mode than in the low power mode, and the first control unit 1400 may obtain an ambient light value at an interval of a shorter period in the normal mode than in the low power mode.

As another example, in the sensor unit 1100, all the sensors may be operated in the normal mode but some of the sensors that are operated in the normal mode may not be operated in the low power mode. Specifically, when the motion sensor 1110 includes at least two of an acceleration sensor, a gyro sensor, and a geomagnetic sensor, the first control unit 1400 may obtain only a corresponding sensed value (e.g., an acceleration value) using any one sensor (e.g., the acceleration sensor) in the low power mode and obtain other corresponding sensed values (e.g., a gyro value and/or a geomagnetic value) using the other sensors (e.g., the gyro sensor and/or the geomagnetic sensor) in the normal mode.

As described above, the sensor unit 1100 may be operated in the low power mode in a specific situation and operated in a normal mode in another specific situation, thereby preventing unnecessary power consumption and improving the efficiency of the battery. The specific situation in which the sensor unit 1100 is operated in the low power mode or the normal mode will be described in detail below.

The first memory 1200 may be configured to store various types of information. Various types of data may be temporarily or semi-permanently stored in the first memory 1200. Examples of the first memory 1200 may include a hard disk drive (HDD), a solid-state drive (SSD), a flash memory, a read-only memory (ROM), a random access memory (RAM), etc.

The first memory 1200 may be provided in a form of being embedded in the wireless communication device 1000 and used by the first control unit 1400 to store, load, and delete the data.

In the first memory 1200, an operating program (OS) for driving the wireless communication device 1000, commands or programs for operating each component of the wireless communication device 1000, and various types of data required for the operation of the wireless communication device 1000 may be stored. For example, in the first memory 1200, the sensed values obtained by the first control unit 1400 using the sensor unit 1100 or data for triggering a wearable device 2000 to be described below may be stored. Specifically, in the first memory 1200, sensed values such as identification information, manufacturer information, product information, the motion value, and the ambient light value of the wireless communication device 1000, activation data, a program related to an algorithm for controlling the sensor unit 1100 and calculating the activation data, etc. may be stored.

The first communication unit 1300 may communicate with a device located outside the wireless communication device 1000. The first communication unit 1300 may use a wireless personal area network (WPAN) communication method, such as Bluetooth or Zigbee. However, since a wireless communication protocol is not limited thereto, the first communication unit 1300 may use a wireless local area network (WLAN) communication method, such as Wi-Fi, or use another known communication method, such as radio-frequency identification (RFID), Near-Field Communication (NFC), magnetic secure transmission (MST), Near-Field Magnetic Induction (NFMI), or the like. The first communication unit 1300 may use a plurality of communication methods. In this case, the first communication unit 1300 may include a plurality of communication modules corresponding to the respective communication methods. The first communication unit 1300 may also be expressed as a transceiver, a transmitter, a receiver, or a transmitter-receiver.

The wireless communication device 1000 may exchange signals or data with the wearable device 2000 through the first communication unit 1300.

The first control unit 1400 may control overall operations of the wireless communication device 1000. As an example, the first control unit 1400 may load and execute programs for the operations of the wireless communication device 1000. As another example, the first control unit 1400 may generate a data packet including specific data using signals or data obtained from the sensor unit 1100.

Here, the first control unit 1400 may be implemented with a device such as a central processing unit (CPU), a microprocessor, a processor core, a multiprocessor, an application-specific integrated circuit (ASIC), or a field programmable gate array (FPGA) according to hardware, software, or a combination thereof. The first control unit 1400 may be provided in the form of an electronic circuit that performs a function of control such as processing electrical signals in hardware, or may be provided in the form of a program or code for driving a hardware circuit in a view of software.

Meanwhile, although not illustrated in FIG. 2, the wireless communication device 1000 may include a power supply unit implemented as a disposable battery or rechargeable battery that supplies power. In this case, when the power supply unit is implemented as a rechargeable battery, the wireless communication device 1000 may further include a charging terminal for charging power.

Figure 3:
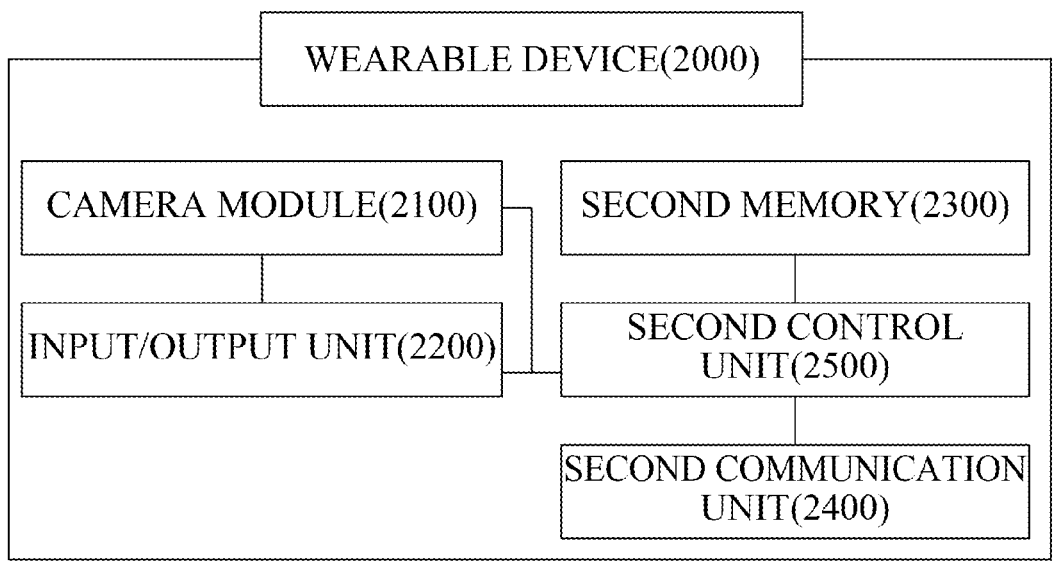
FIG. 3 is a diagram illustrating a wearable device according to an embodiment of the present invention.

FIG. 3 is a diagram illustrating a wearable device 2000 according to an embodiment of the present invention.

Referring to FIG. 3, the wearable device 2000 may include a camera module 2100, an input/output unit 2200, a second memory 2300, a second communication unit 2400, and a second control unit 2500.

The camera module 2100 may shoot a video in a preset area set based on the camera 2100. For example, the camera module 2100 may have a preset field of view (FoV), and the second control unit 2500 may use the camera module 2100 to obtain video data related to medication adherence of the user. More specifically, when the wearable device 2000 is worn on the user's wrist, at least a portion of the user's palm may be included in the FoV of the camera module 2100, and as the user performs medication adherence using his or her hand, the camera module 2100 may shoot a video related to a medication and a medication adherence action of the user.

The camera module 2100 may shoot the video using a red, green, and blue (RGB) camera, infrared camera, stereo camera, or depth camera method. Meanwhile, the wearable device 2000 may include a plurality of camera modules that use different photographing methods.

The input/output unit 2200 may include an input module that receives a user input from the user and an output module that outputs and provides various types of information to the user.

Here, the user input may be made in various forms including a key input, a touch input, and a voice input. The input module is a comprehensive concept that includes not only a traditional type of keypad, keyboard, and mouse, but also a touch sensor that detects the user's touch, and various types of input devices that detect or receive various types of user inputs. Further, the input module may be implemented in the form of an input interface (e.g., a Universal Serial Bus (USB) port, a Personal System/2 (PS/2) port, etc.) for connecting an external input device that receives the user input to an electronic device, instead of being implemented with a device that detects the user input by itself.

The output module is a comprehensive concept that includes a display that outputs a video, a speaker that outputs sound, a haptic device that generates vibration, and other various types of output devices. In addition, the output module may be implemented in the form of a port-type output interface for connecting an individual output device to an electronic device.

The second memory 2300 may be configured to store various types of information. Various types of data may be temporarily or semi-permanently stored in the second memory 2300. Since a configuration or implementation form of the second memory 2300 is the same as that of the first memory 1200 described above, duplicate content will be omitted.

In the second memory 2300, an OS for driving the wearable device 2000, commands or programs for operating each component of the wearable device 2000, and various types of data required for the operation of the wearable device 2000 may be stored. As an example, in the second memory 2300, video data obtained by the second control unit 2500 using the camera module 2100 or data obtained from the wireless communication device 1000 may be stored. As another example, in the second memory 2300, identification information, manufacturer information, and/or product information of the wireless communication device 1000 may be stored.

The second communication unit 2400 may communicate with a device located outside the wearable device 2000. Since a configuration or implementation form of the second communication unit 2400 is the same as that of the first communication unit 1300 described above, duplicate content will be omitted.

The wearable device 2000 may exchange signals or data with the wireless communication device 1000, a server 3000, or a terminal device 4000 through the second communication unit 2400.

The second control unit 2500 may control overall operations of the wearable device 2000. As an example, the second control unit 2500 may load and execute programs for the operations of the wearable device 2000. As another example, the second control unit 2500 may process the video data obtained from the camera module 2100. As still another example, the second control unit 2500 may transmit a data packet including specific data to the wireless communication device 1000 through the second communication unit 2400 or transmit the video data to the server 3000.

Since a configuration or implementation form of the second control unit 2500 is the same as that of the second control unit 1400 described above, duplicate content will be omitted.

Meanwhile, although not illustrated in FIG. 3, the wearable device 2000 may further include various types of sensor modules. As an example, the wearable device 2000 may include a heart rate sensor, a temperature sensor, a blood pressure sensor, a proximity sensor, an electroencephalogram (EEG) sensor, or the like for obtaining the user's biometric information. As another example, the wearable device 2000 may include an acceleration sensor, a gyro sensor, a geomagnetic sensor, or the like for detecting movement (e.g., a medication adherence action, a walking or running action, a falling action, etc.) of the user who wears the wearable device 2000.

Further, the wearable device 2000 may include a power supply unit implemented as a disposable battery or rechargeable battery that supplies power. In this case, when the power supply unit is implemented as a rechargeable battery, the wearable device 2000 may further include a charging terminal for charging power.

Figure 4:
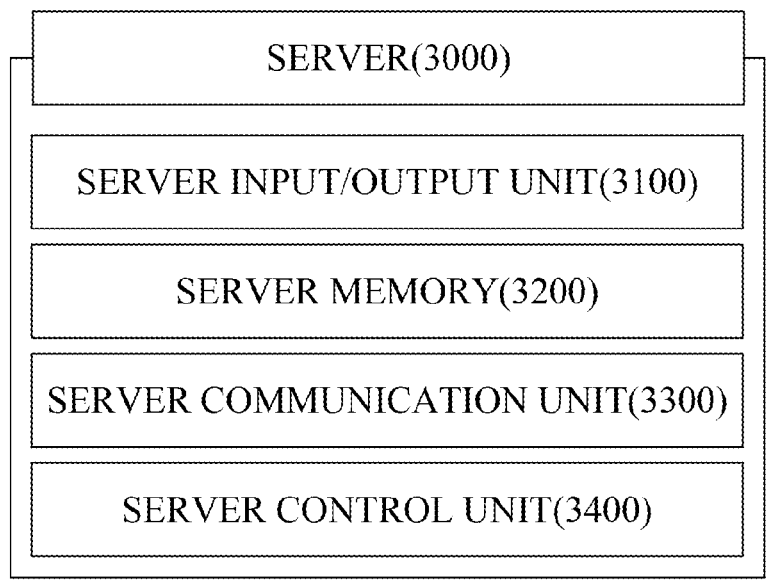
FIG. 4 is a diagram illustrating a server according to an embodiment of the present invention.

FIG. 4 is a diagram illustrating a server 3000 according to an embodiment of the present invention.

The server 3000 may include components for processing, analysis, and management of data. For example, referring to FIG. 4, the server 3000 may include a server input/output unit 3100, a server memory 3200, a server communication unit 3300, and a server control unit 3400. Since a form or implementation method of each component of the server 3000 is the same as that of the wireless communication device 1000 or the wearable device 2000 described above, duplicate content will be omitted.

The server 3000 may exchange data with the wearable device 2000 and the terminal device 4000 through the server communication unit 3300. As an example, the server communication unit 3300 may receive video data related to medication adherence from the wearable device 2000 and provide, to the wearable device 2000 and/or the terminal device 4000, a result of determining whether the user performs the medication adherence, which is derived from the video data by the server control unit 3400. As another example, the server communication unit 3300 may obtain information such as medication information, prescription information, a medication adherence schedule, or the user's status from the terminal device 4000.

The server 3000 may store an OS for driving the server 3000, commands or programs for operating each component of the server 3000, and various types of data required for the operation of the server 3000 in the server memory 3200. Further, the server 3000 may store a program used to determine whether the medication adherence is performed in the server memory 3200.

The server control unit 3400 may control overall operations of the server 3000. As an example, the server control unit 3400 may load and execute programs for the operations of the server 3000. As another example, the server control unit 3400 may apply the video data obtained from the wearable device 2000 to an analysis program to calculate a result of determining whether the user performs the medication adherence.

The terminal device 4000 may provide information on whether the user performs the medication adherence to the user, a guardian, or medical personnel or provide an application or a user interface/user experience (UI/UX) for managing the medication adherence of the user to the user, the guardian, or the medical personnel. To this end, the terminal device 4000 may include an input unit, an output unit, a memory, a communication unit, a control unit, and a power supply unit. Since a form or implementation method of each component of the terminal device 4000 is the same as that of the wireless communication device 1000 or the wearable device 2000 described above, duplicate content will be omitted.

An application executed in the terminal device 4000 may provide a scheduling service or a notification service for inducing the medication adherence of the user. In this case, the terminal device 4000 may reflect the data obtained from the wearable device 2000 or the server 3000 when executing the application.

Meanwhile, the terminal device 4000 may be omitted from a medication adherence monitoring system 100, and the function of the terminal device 4000 described above may be implemented or performed in the wearable device 2000 or the server 3000.

Hereinafter, the operation of the medication adherence monitoring system 100 will be described with reference to FIGS. 5 to 17.

Figure 5:
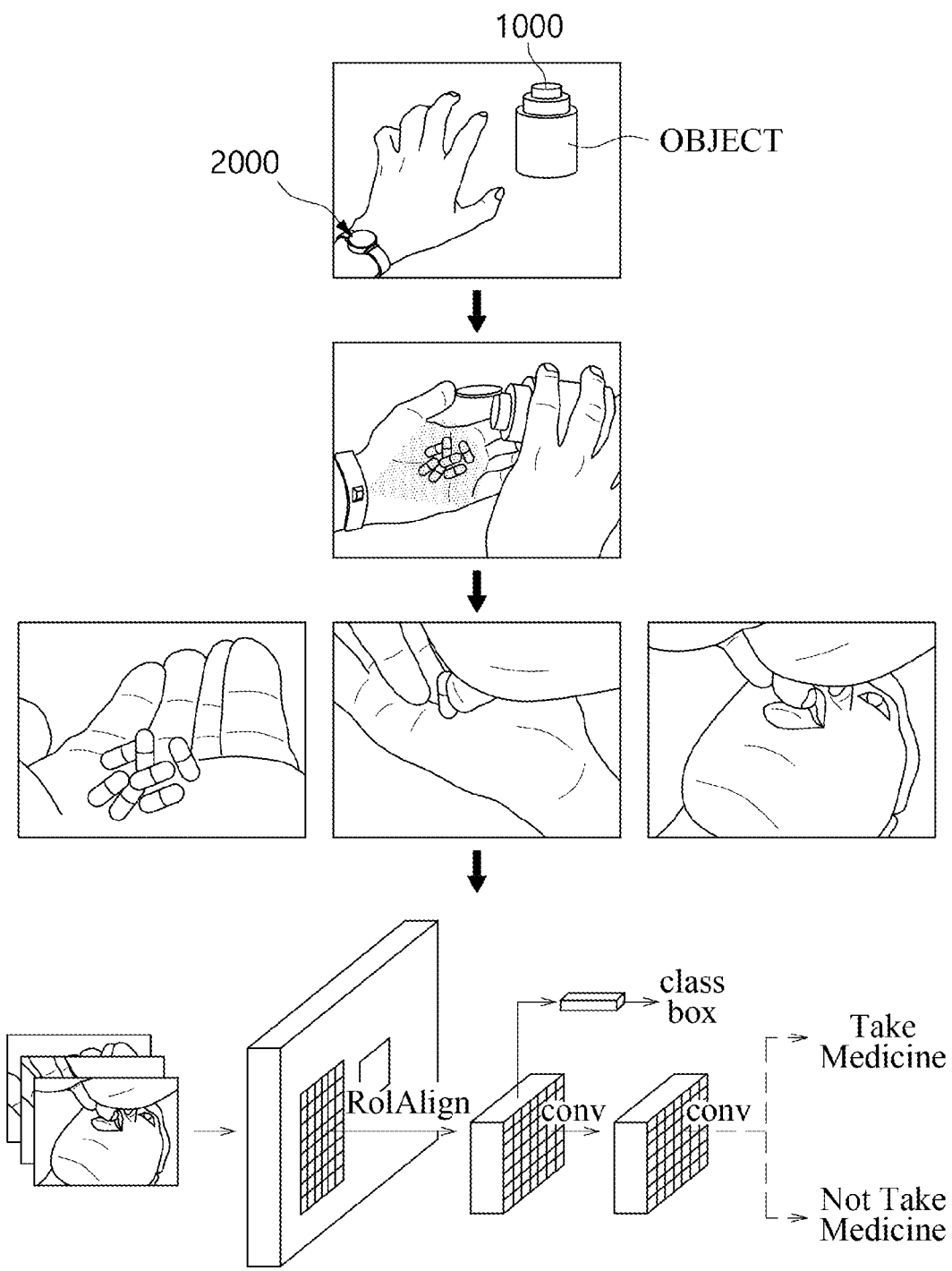
FIG. 5 is a diagram illustrating an operation process of a medication adherence monitoring system according to an embodiment of the present invention.

FIG. 5 is a diagram illustrating an operation process of a medication adherence monitoring system 100 according to an embodiment of the present invention.

Referring to FIG. 5, the medication adherence monitoring system may be used as follows in an environment in which a user performs medication adherence.

A wireless communication device 1000 may be physically connected to an object. As an example, the wireless communication device 1000 may be attached to or detached from the object. As another example, the wireless communication device 1000 may be connected to the object through a connecting member such as a clip, a string, or the like.

Here, the object may refer to an object that the user has to approach for the medication adherence. For example, the object may include a medication container or a medication delivery device in which a medication is contained.

The wireless communication device 1000 may be connected to the object in various ways. As an example, the wireless communication device 1000 may include an adhesive member and may be attached to at least an area of the object through the adhesive member. Specifically, the wireless communication device 1000 may be attached to the object using double-sided tape, Velcro tape, an adhesive pad, a gel pad, an epoxy adhesive, a silicone adhesive, or the like. As another example, the wireless communication device 1000 may be forcibly coupled to at least an area of the object. The wireless communication device 1000 may be located on the object and may serve to detect movement of the object in the process in which the user performs the medication adherence, as will be described below.

The wireless communication device 1000 may have various shapes. As an example, the wireless communication device 1000 may have a shape of a figure including a curved surface, such as a cylindrical shape, a polygonal column shape, a hemispherical shape, or a pyramidical shape, or a shape of a figure including a flat surface. As another example, the wireless communication device 1000 may have a shape corresponding to a shape of the object. Specifically, when the object is a medication container having a cylindrical shape, the wireless communication device 1000 may also have a cylindrical shape or a hemispherical shape.

The wearable device 2000 may access the wireless communication device 1000 in the process in which the user performs the medication adherence. For example, when the wearable device 2000 is worn on the user's wrist and the user approaches the object in order to take the medication out of the object, the wearable device 2000 may be located close to the wireless communication device 1000.

The wireless communication device 1000 may be moved or rotated in the process in which the user performs the medication adherence. For example, when the user moves or rotates the object to which the wireless communication device 1000 is attached in order to take the medication out of the object, the wireless communication device 1000 may be moved or rotated according to the movement of the object. In this case, the wireless communication device 1000 may generate activation data in consideration of a degree of movement of the wireless communication device 1000 and an environment around the wireless communication device 1000 and provide the generated activation data to the wearable device 2000.

Here, the activation data may refer to data instructing activation of a specific function of a device located outside the wireless communication device 1000. For example, the activation data may refer to data instructing activation of the camera module 2100 of the wearable device 2000. The activation data will be described in detail below.

The wearable device 2000 may activate the camera module 2100 to shoot a video related to the medication adherence of the user. For example, when the wearable device 2000 receives the activation data from the wireless communication device 1000, the wearable device 2000 may activate the camera module 2100 to shoot the video. In this case, since time consumed for generating the activation data in the wireless communication device 1000 and providing the activation data to the wearable device 2000 is relatively shorter than time consumed for the user to take the medication out of the object or time required for the user to perform the medication adherence, the wearable device 2000 may obtain video data related to the medication adherence of the user, specifically, video data including a process of taking the medication or a process of injecting the medication to the body.

The server 3000 may analyze the video data received from the wearable device 2000 to determine whether the user performs the medication adherence. Further, the server 3000 may transmit a result of determining whether the user performs the medication adherence to the wearable device 2000 or the terminal device 4000 to provide the result to the user, a guardian, or medical personnel.

Hereinafter, the operation of each component of the medication adherence monitoring system 100 will be described in more detail.

Hereinafter, a method of transmitting or receiving data in the wireless communication device 1000 and the wearable device 2000 will be described with reference to FIGS. 6 to 8.

Figure 6:
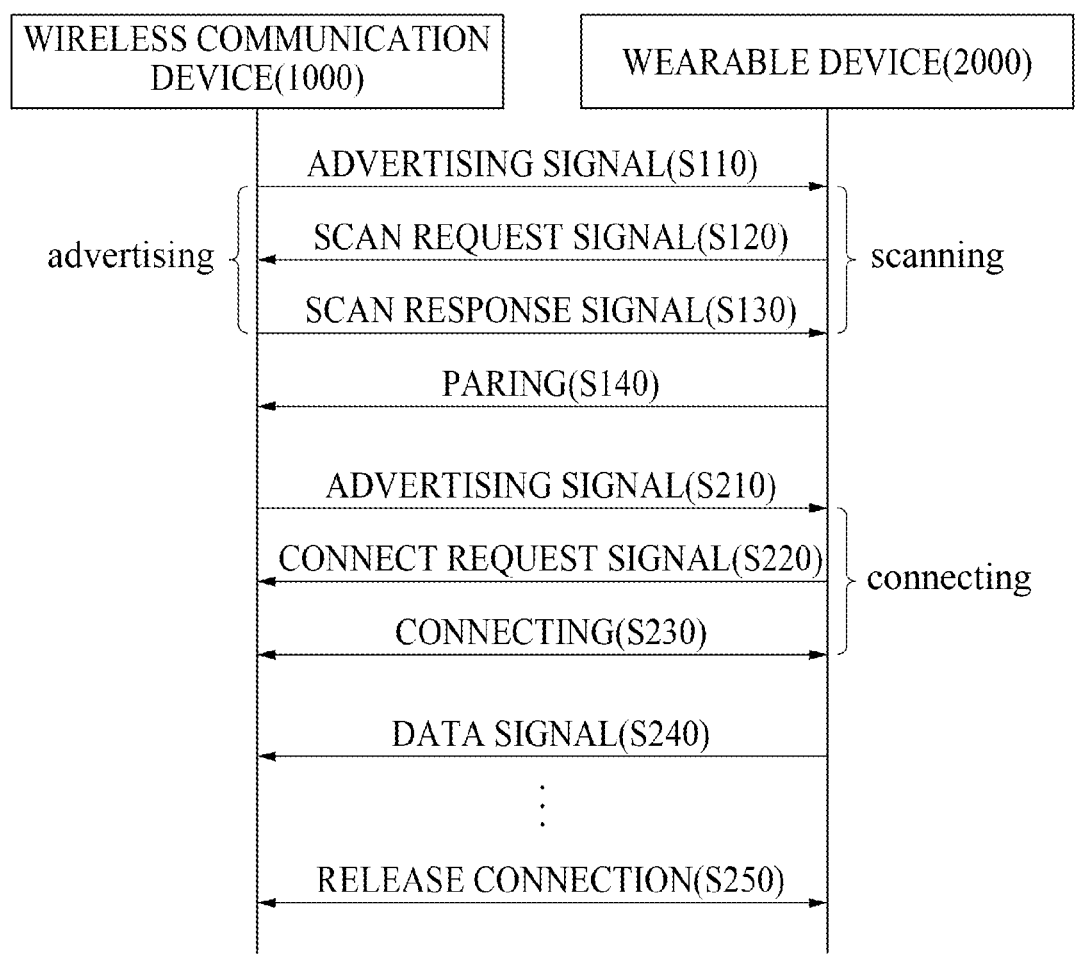
FIG. 6 is a diagram illustrating a communication process between a wireless communication device and a wearable device according to an embodiment of the present invention.

FIG. 6 is a diagram illustrating a communication process between the wireless communication device 1000 and the wearable device 2000 according to the embodiment of the present invention.

Figure 7:
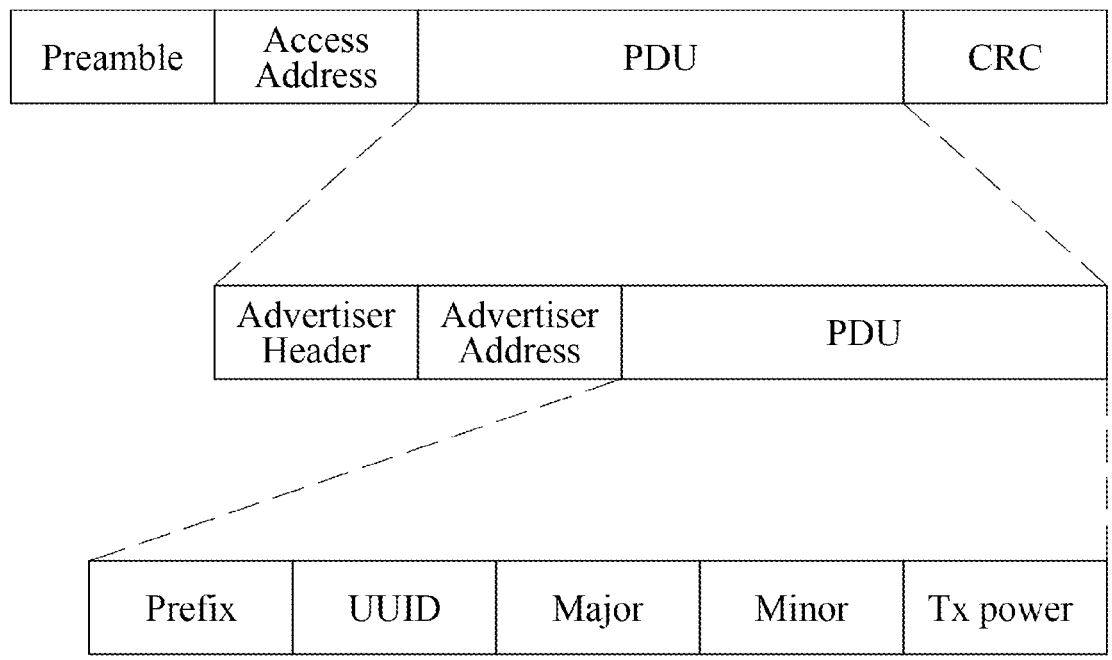
FIGS. 7 and 8 are diagrams illustrating data packets transmitted by a wireless communication device according to an embodiment of the present invention.
Figure 8:
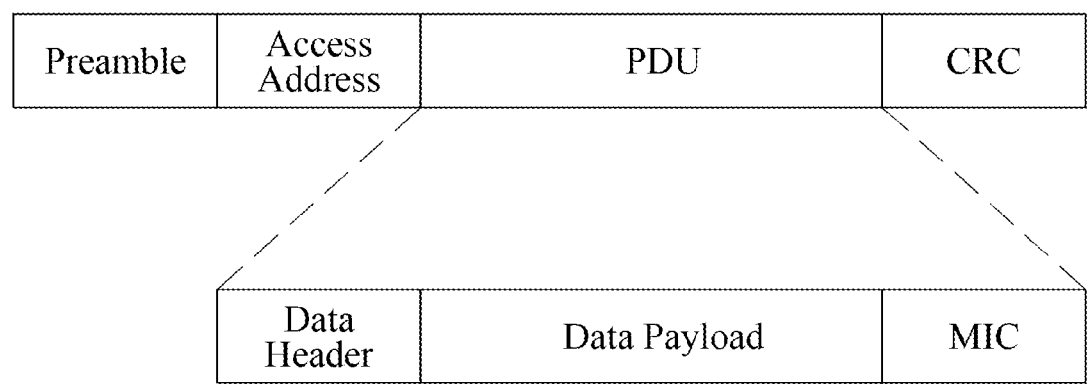

FIGS. 7 and 8 are diagrams illustrating data packets transmitted by the wireless communication device 1000 according to the embodiment of the present invention.

Referring to FIG. 6, the wireless communication device 1000 and the wearable device 2000 may be subjected to a pairing process and a connecting process in order to transmit and receive data.

The pairing process may refer to a process in which different devices recognize each other before transmitting or receiving data through wireless communication. Specifically, the wireless communication device 1000 and the wearable device 2000 may share a link-key and establish an encrypted connection during the pairing process.

Hereinafter, the pairing process will be described in detail.

The wireless communication device 1000 may transmit an advertising signal to the outside (S110). For example, the first control unit 1400 may transmit the advertising signal to the outside using the first communication unit 1300.

The advertising signal may refer to a data packet including specific data. For example, referring to FIG. 7, the advertising signal may be expressed as an advertising channel packet composed of a preamble, an access address, a protocol data unit (PDU), and a cyclic redundancy check (CRC). Here, the preamble may have a data size of 1 octet, the access address may have a data size of 4 octets, the PDU may have a data size of 2 to 39 octets, and the CRC may have a data size of 3 octets.

Meanwhile, according to an embodiment of the present invention, the advertising signal is a signal for a pairing process and may include identification data, manufacturer data, and/or transmission strength data of the wireless communication device 1000 but may not include the sensed value and activation data obtained from the wireless communication device 1000.

According to another embodiment of the present invention, the advertising signal may include not only identification data, manufacturer data, and transmission strength data of the wireless communication device 1000 to be described below, but also a sensed value such as a motion value or an ambient light value and/or activation data to be described below.

The advertising signal may be expressed as an advertising PDU, an advertising packet, an advertising frame, advertising, or the like.

The advertising signal may be transmitted in a broadcast method in which a signal is transmitted to unspecified targets or in a unicast method in which a signal is transmitted to a specific target.

The wireless communication device 1000 may transmit the advertising signal in a specific period. For example, the wireless communication device 1000 may transmit the advertising signal in a period which is set within a range of 20 ms to 10.24 s. In this case, the wireless communication device 1000 may set a period of transmitting the advertising signal in consideration of the efficiency of the battery and of a time point at which the user performs the medication adherence.

When the wearable device 2000 receives the advertising signal, the wearable device 2000 may transmit a scan request signal (S120). For example, when the second control unit 2500 receives the advertising signal from the first communication unit 1300, the second control unit 2500 may transmit the scan request signal to the outside through the second communication unit 2400. In this case, when the advertising signal does not include information about the wireless communication device 1000, the wearable device 2000 may not transmit the scan request signal.

The wireless communication device 1000 may transmit a scan response signal (S130). For example, when the first control unit 1400 receives the scan request signal from the second communication unit 2400, the first control unit 1400 may transmit the scan response signal to the outside using the first communication unit 1300.

Each of the scan request signal and the scan response signal may be composed of a data packet including specific data. For example, the scan request signal may include data for requesting a device name, unique identification information, or the like of a target to communicate with, and the scan response signal may include data indicating a device name, unique identification information, or the like corresponding to information requested in the scan request signal.

Each of the scan request signal and the scan response signal may be composed of a data packet having the same configuration as the data packet of the advertising signal.

The scan request signal may be expressed as a scan request PDU, a scanning PDU, a scan request packet, a scan request frame, a scan request, or the like.

The above-described advertising signal, scan request signal, and scan response signal may be transmitted or received at a specific time point in a specific frequency band. For example, when the wireless communication device 1000 and the wearable device 2000 use Bluetooth Low Energy (BLE) communication, the advertising signal, the scan request signal, and the scan response signal may be transmitted or received through three channels of a BLE communication band of 2.400 GHz to 2.480 GHz.

The wireless communication device 1000 and the wearable device 2000 may be paired (S140). For example, the wireless communication device 1000 and the wearable device 2000 may share a preset link-key or encryption key through the scan request signal and/or the scan response signal to maintain an encrypted connection state.

When the wireless communication device 1000 and the wearable device 2000 are paired, the pairing process may not be performed until the pairing is released.

The pairing between the wireless communication device 1000 and the wearable device 2000 may be released when a preset condition is satisfied. For example, the wearable device 2000 may receive an input from the user or the like through the input/output unit 2200 to release the pairing by deleting the link-key or encryption key shared with the wireless communication device 1000.

Meanwhile, when the wireless communication device 1000 and the wearable device 2000 have been paired in the past, the step S140 in which the wireless communication device 1000 and the wearable device 2000 are paired may be omitted. For example, when the wireless communication device 1000 and the wearable device 2000 have already shared the link-key or the encryption key, the wireless communication device 1000 may transmit the advertising signal (S110) and the wearable device 2000 may transmit the scan request signal (S120). When the wireless communication device 1000 transmits the scan response signal (S130), the wireless communication device 1000 and the wearable device 2000 may be automatically paired to transmit or receive the data.

The connection process may refer to a process in which different devices share information required for transmitting or receiving the data after pairing. Specifically, the wireless communication device 1000 and the wearable device 2000 may set a frequency band in which data is to be transmitted or received to or from each other or set a data transmission or reception time point during the connection process. In this case, the data transmission or reception time point may be set in consideration of the efficiency of the battery and of the time at which the user performs the medication adherence.

Hereinafter, the connection process will be described in detail.

The wireless communication device 1000 may transmit an advertising signal to the wearable device 2000 (S210). For example, the first control unit 1400 may transmit the advertising signal to the second communication unit 2400 using the first communication unit 1300. Here, the advertising signal in step S210 may have the same data packet structure as the advertising signal in step S110. Meanwhile, the advertising signal may be transmitted through the specific frequency band set between the wireless communication device 1000 and the wearable device 2000 during the pairing process.

The wearable device 2000 may transmit a connect request signal to the wireless communication device 1000 (S220). For example, when the second control unit 2500 receives the advertising signal from the first communication unit 1300, the second control unit 2500 may transmit the connect request signal to the first communication unit 1300 through the second communication unit 2400.

The connect request signal may be expressed as a connect request PDU, an initiation PDU, a connect request packet, a connect request frame, a connect request, or the like.

The wireless communication device 1000 and the wearable device 2000 may be connected to each other (S230). For example, when the first control unit 1400 receives the connect request signal from the second communication unit 2400, the first control unit 1400 may change an operation mode from an advertising mode to a connecting mode. Here, the advertising mode may refer to a mode in which the advertising signal is periodically transmitted to the outside before the wireless communication device 1000 is connected to the wearable device 2000. In addition, here, the connecting mode may refer to a mode in which the data is transmitted through a data channel to be described below formed between the wireless communication device 1000 and the wearable device 2000 after the wireless communication device 1000 is connected to the wearable device 2000.

In the connection step S230, a data transmitting/receiving channel may be formed between the wireless communication device 1000 and the wearable device 2000. When the data transmitting/receiving channel is formed, the data transmission or reception frequency band and time point of the wireless communication device 1000 may correspond to the data transmission or reception frequency band and time point of the wearable device 2000.

When the wireless communication device 1000 and the wearable device 2000 are connected to each other, the wireless communication device 1000 and the wearable device 2000 may transmit or receive a signal for periodically confirming the connection through the data transmitting/receiving channel while the connection is maintained. For example, when the wireless communication device 1000 or the wearable device 2000 transmits a connection acknowledge request signal while the connection is maintained, the wearable device 2000 or the wireless communication device 1000 may transmit a connection acknowledge signal. Meanwhile, according to an embodiment of the present invention, the wearable device 2000 may activate the camera module 2100 on the basis of an activation signal received from the wireless communication device 1000, and the wireless communication device 1000 may transmit the activation signal together with the connection acknowledge request signal or the connection acknowledge signal to the wearable device 2000 after being connected to the wearable device 2000. The connection acknowledge signal might be also interpreted as a connection confirm signal which indicates confirmation of the connection. The connection acknowledge request signal might be also interpreted as a connection confirm request signal which requests the confirmation of the connection.

In the connection process, the wireless communication device 1000 may generate activation data. For example, in at least one operation of step S210 in which the wireless communication device 1000 transmits the advertising signal to the wearable device 2000, step S220 in which the wearable device 2000 transmits the connect request signal to the wireless communication device 1000, and step S230 in which the wireless communication device 1000 and the wearable device 2000 are connected to each other, the wireless communication device 1000 may operate the sensor unit 1100 and generate the activation data on the basis of the sensed value obtained by using the sensor unit 1100. Meanwhile, the wireless communication device 1000 may generate the activation data during the pairing process, similar to the connection process.

The above-described connection process may or may not be performed according to a positional relationship between the wireless communication device 1000 and the wearable device 2000. For example, when the wireless communication device 1000 and the wearable device 2000 are located within a preset distance, the connection process may be performed between the wireless communication device 1000 and the wearable device 2000.

Meanwhile, the pairing process and the connection process may be performed automatically or may be performed manually by a user or the like. As an example, when the wearable device 2000 receives the advertising signal from the wireless communication device 1000, the wearable device 2000 may output the information about the wireless communication device 1000 to the user or the like through the input/output unit 2200 and receive an input from the user to transmit the scan request signal or the connect request signal to the wireless communication device 1000. As another example, when the advertising signal received from the wireless communication device 1000 includes preset data such as a product number or manufacturing number, the wearable device 2000 may automatically transmit the scan request signal or the connect request signal to the wireless communication device 1000.

After the connection step S230, the wireless communication device 1000 may transmit a data signal to the wearable device 2000 (S240). For example, the wireless communication device 1000 may transmit a data signal including specific data to the wearable device 2000 through the data transmitting/receiving channel formed in the connection step S230.

The data signal may refer to a data packet including specific data. For example, referring to FIG. 8, the data signal may be expressed as a data channel packet composed of a preamble, an access address, a PDU, and a CRC. Here, the preamble may have a data size of 1 octet, the access address may have a data size of 4 octets, the PDU may have a data size of 2 to 257 octets, and the CRC may have a data size of 3 octets. In addition, here, the data signal may include identification data, manufacturer data, transmission strength data, motion data, ambient light data, and/or activation data of the wireless communication device 1000 to be described below.

Meanwhile, referring to FIGS. 7 and 8 again, the advertising channel packet and the data channel packet may have different structures.

For example, the PDU of the advertising channel packet may include an advertiser header, an advertiser address, and an advertising payload. Here, the advertiser address may refer to a media access control (MAC) address for indicating product-specific identification information. In addition, here, the advertising payload may include a universally unique identifier (UUID) for indicating that the product is a product of a specific manufacturer, and transmission strength (Tx power) indicating the strength or intensity of a transmitted signal.

In addition, for example, the PDU of the data channel packet may include a data header, a data payload, and a message integrity check (MIC). Here, the MIC may be omitted.

As described above, the PDU of the advertising channel packet and the PDU of the data channel packet may have different lengths. Specifically a maximum length of the PDU of the data channel packet may be longer than a maximum length of the PDU of the advertising channel packet so that the PDU of the data channel packet may include more data. Therefore, when the wireless communication device 1000 transmits the identification data or the advertiser address of the wireless communication device 1000 having a relatively small size to the wearable device 2000, the wireless communication device 1000 may transmit the advertising signal in the form of the advertising channel packet, and when the wireless communication device 1000 transmits the sensed values to be described below, the activation data, etc. having a relatively large size, the wireless communication device 1000 may transmit the data signal in the form of the data channel packet.

In the data signal transmission step S240, the wireless communication device 1000 may include data to be transmitted in the data payload of the data channel packet to transmit the data to the wearable device 2000.

Meanwhile, as will be described below, the wireless communication device 1000 may transmit the data to the wearable device 2000 without the pairing process or the connection process. In this case, the wireless communication device 1000 may include the data to be transmitted in the advertising payload of the advertising channel packet to transmit the data to the wearable device 2000.

The connection between the wireless communication device 1000 and the wearable device 2000 may be released (S250). When the preset condition is satisfied, the wireless communication device 1000 and the wearable device 2000 may stop the data transmission or reception or may transmit or receive a connection release signal and/or a connection release acknowledge signal to release the connection formed in the connection step S230. The connection release acknowledge signal might be also interpreted as a connection release confirm signal which indicates confirmation that the connection is released.

For example, when strength of a signal received by the wireless communication device 1000 or the wearable device 2000 is less than or equal to a preset value, the connection between the wireless communication device 1000 and the wearable device 2000 may be released. Specifically, when strength of a signal obtained from the wireless communication device 1000 is less than or equal to strength corresponding to the preset distance, the second control unit 2500 may transmit the connection release signal to the wireless communication device 1000 or may stop the data signal transmission to release the connection with the wireless communication device 1000.

As another example, when the wireless communication device 1000 transmits the activation data to the wearable device 2000, the connection between the wireless communication device 1000 and the wearable device 2000 may be released. For example, the first control unit 1400 may transmit a data signal including the activation data to the wearable device 2000 and then transmit the connection release signal or stop the data signal transmission to release the connection with the wearable device 2000.

As still another example, when the wireless communication device 1000 and the wearable device 2000 are connected to each other and a predetermined time has elapsed, the connection between the wireless communication device 1000 and the wearable device 2000 may be released. Alternatively, when the data signal is transmitted from the wireless communication device 1000 to the wearable device 2000 or the connection acknowledge request signal or the acknowledge signal is transmitted from the wearable device 2000 to the wireless communication device 1000 and then a predetermined time has elapsed, the connection between the wireless communication device 1000 and the wearable device 2000 may be released.

As yet another example, when the sensed value obtained by the wireless communication device 1000 using the sensor unit 1100 is less than or equal to a preset value, the connection between the wireless communication device 1000 and the wearable device 2000 may be released. More specifically, when the motion value obtained from the motion sensor by the first control unit 1400 is less than or equal to a preset value or when an amount of change in the motion value is less than or equal to a preset amount of change, the data signal transmission may stop. Alternatively, when the ambient light value obtained from the ambient light sensor by the first control unit 1400 is less than or equal to a preset value, the connection release signal may be transmitted or the data signal transmission may stop.

Meanwhile, an operating state of the wireless communication device 1000 may be changed during the pairing process or the connection process. As an example, the wireless communication device 1000 may be operated in a sleep state to be described below before being paired with the wearable device 2000 and then the sleep state may be changed to a standby state to be described below during pairing with the wearable device 2000 or after being paired with the wearable device 2000 so that the wireless communication device 1000 may be operated in the standby state. As another example, the wireless communication device 1000 may be operated in the sleep state before being connected to the wearable device 2000 and then the sleep state may be changed to a standby state to be described below during connection to the wearable device 2000 or after being connected to the wearable device 2000 so that the wireless communication device 1000 may be operated in the standby state. In the above, a case in which the wireless communication device 1000 and the wearable device 2000 perform data communication using BLE technology has been mainly described, but the technological concept of the present invention is not limited thereto. For example, when the wireless communication device 1000 and the wearable device 2000 use beacon communication, the above-described the pairing process and/or connection process may be omitted. As still another example, the wireless communication device 1000 and the wearable device 2000 may transmit or receive the data using Wi-Fi communication.

Hereinafter, a method of generating activation data in the wireless communication device 1000 will be described with reference to FIGS. 9 to 11.

The medication adherence monitoring system 100 may collect data related to the medication adherence of the user in order to monitor the medication adherence of the user. Here, the data related to the medication adherence may refer to various pieces of data. For example, the data related to the medication adherence may include images, videos, sounds, motions, etc. that reflect the process in which the user performs the medication adherence. Hereinafter, a case in which the data related to the medication adherence is video data that reflects the process in which the user performs the medication adherence is mainly described, but the technological concept of the present invention is not limited thereto, and image data, sound data, motion data, or other data related to the medication adherence may also be applied.

In order for the above-described video data to sufficiently reflect the process in which the user performs the medication adherence, a time point at which video shooting starts and a position where the video is shot should be considered important. For example, the time point at which the video shooting starts may be set based on a time point at which the user approaches the object containing the medication at a certain velocity or higher in order to perform the medication adherence, a time point at which the object containing the medication is moved, a time point at which a cap of the object containing the medication is separated or moved, or a time point at which the medication is taken out of the object. In addition, for example, the position where the video is shot may be the wearable device 2000 worn on the user's body, and the position where the video is shot may be around the user's wrist, eye, or finger according to the position where the wearable device 2000 is worn. For example, a time point at which the video is shot may be set based on a time point at which the user moves the object containing the medication in order to perform the medication adherence, and the position where the video is shot may be the wearable device 2000 worn on the user's body.

Meanwhile, the wireless communication device 1000 and the wearable device 2000 may interact with each other in order to improve a degree to which the video data reflects the process of the medication adherence of the user. For example, the wireless communication device 1000 may detect the movement of the object to determine whether the video shooting starts, and may transmit the activation data to the wearable device 2000 according to a result of the determination to activate the camera module 2100 of the wearable device 2000.

Here, the activation data may refer to data indicating that the medication adherence of the user starts. For example, when the wireless communication device 1000 detects the movement of the object and/or the environment around the object to determine that the medication adherence of the user starts, the wireless communication device 1000 may generate the activation data to provide the activation data to the wearable device 2000. Furthermore, when the wearable device 2000 receives the activation data, the wearable device 2000 may activate the camera module 2100 to shoot a video. Meanwhile, the activation data may be interpreted as data indicating whether it is necessary to initiate shooting a video or as data instructing the activation of the camera module 2100 of the wearable device 2000.

Figure 9:
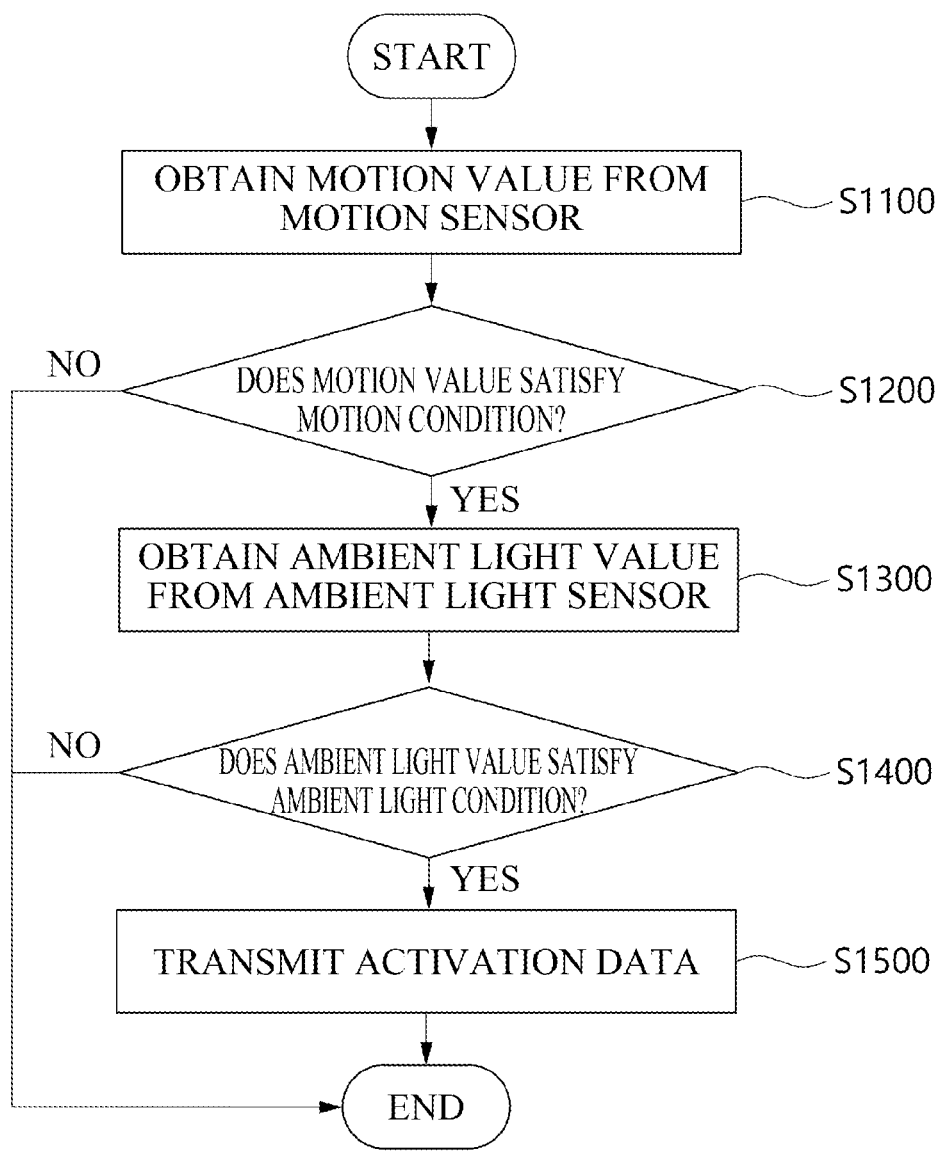
FIG. 9 is a diagram illustrating a method of generating activation data in a wireless communication device according to an embodiment of the present invention.

FIG. 9 is a diagram illustrating a method of generating activation data in the wireless communication device 1000 according to the embodiment of the present invention.

Figure 10:
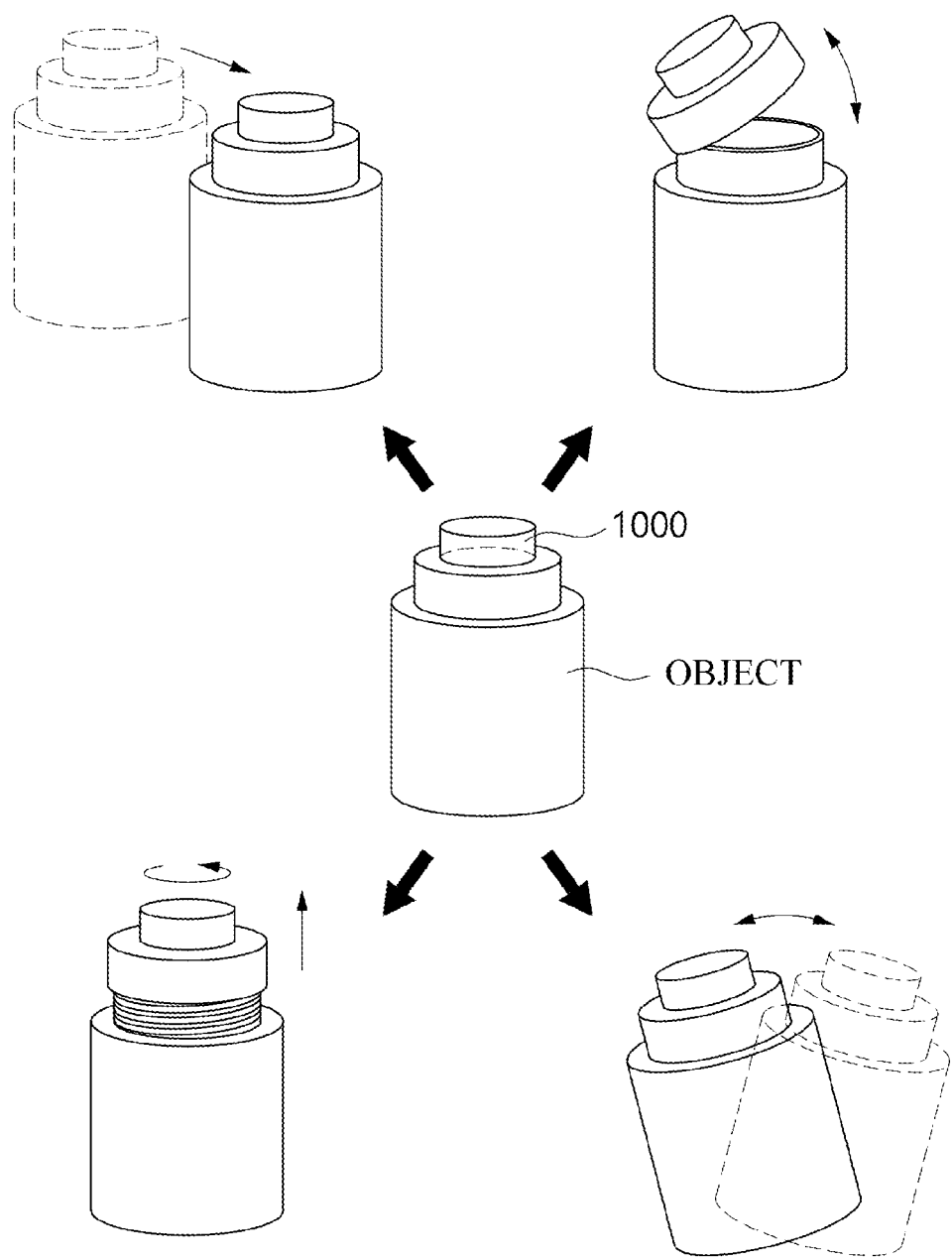
FIGS. 10 and 11 are diagrams illustrating states of a wireless communication device and environments around the wireless communication device, which are detected by a sensor unit of a wireless communication device.
Figure 11:
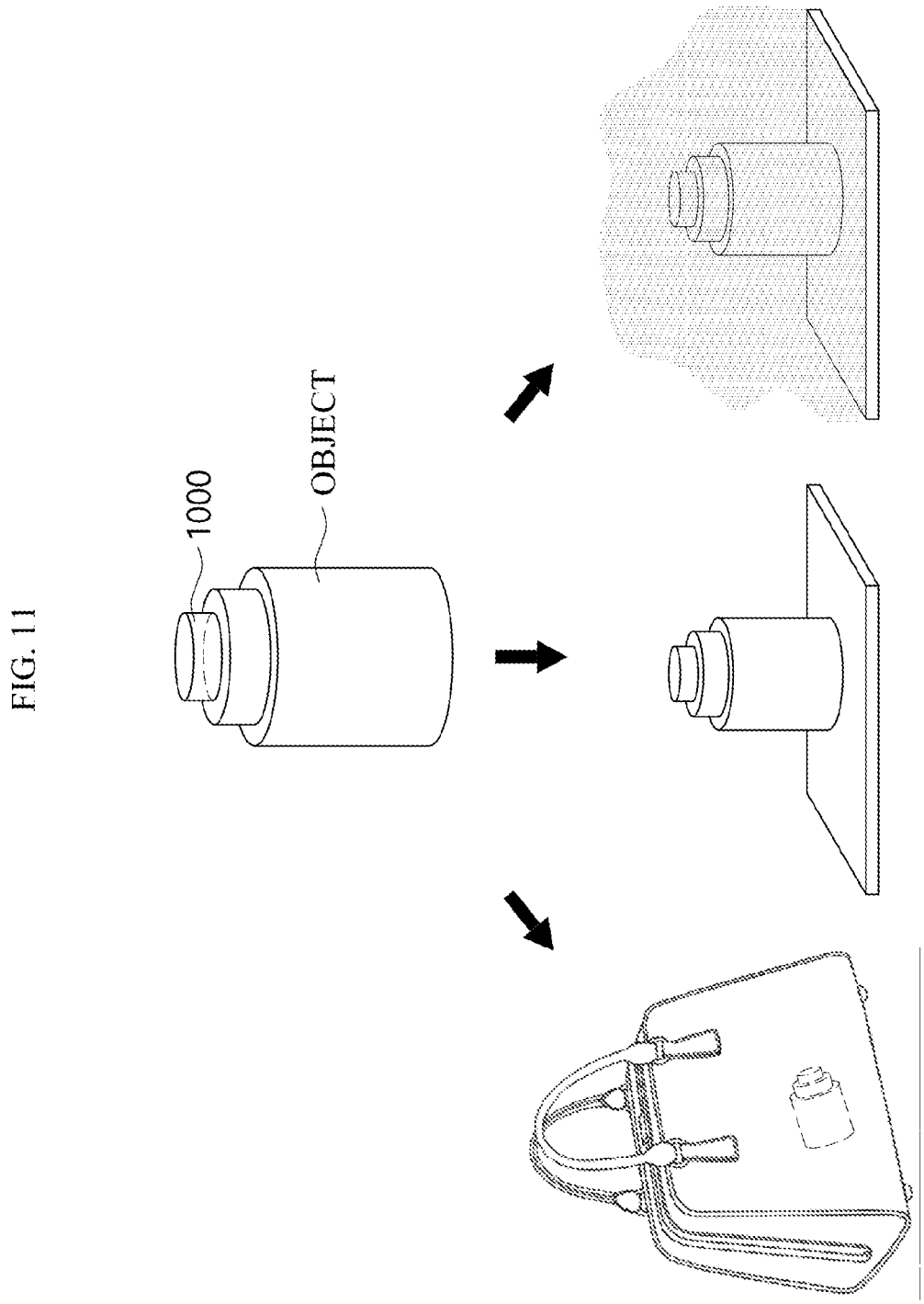

FIGS. 10 and 11 are diagrams illustrating states of the wireless communication device 1000 or environments around the wireless communication device 1000, which are detected by the sensor unit 1100 of the wireless communication device 1000.

Referring to FIG. 9, the wireless communication device 1000 may perform a step S1100 of obtaining a motion value from the motion sensor 1110, a step S1200 of determining whether the motion value satisfies a motion condition, a step S1300 of obtaining an ambient light value from the ambient light sensor 1120, a step S1400 of determining whether the ambient light value satisfies an ambient light condition, and a step S1500 of generating or changing activation data.

Hereinafter, each operation will be described in detail.

The wireless communication device 1000 may obtain the motion value from the motion sensor 1110 (S1100). For example, the wireless communication device 1000 may be attached to the object, and when the user moves or rotates the object for medication adherence, the first control unit 1400 may obtain a motion value corresponding to the movement and/or rotation of the object from the motion sensor 1110.

The motion sensor 1110 may include at least one of an acceleration sensor, a gyro sensor, and a geomagnetic sensor, and the motion value may include at least one of an acceleration value, a gyro value, and a geomagnetic value.

The wireless communication device 1000 may detect the movement of the object using the motion sensor 1110. For example, referring to FIG. 10, the wireless communication device 1000 may be attached to the object during the medication adherence process and may be moved, rotated, or inclined together with the object.

Here, the wireless communication device 1000 may detect a change in position of the wireless communication device 1000 according to a change in position of the object using an acceleration sensor and/or a gyro sensor. In this case, the change in position of the wireless communication device 1000 may correspond to a case in which the user moves the object for medication adherence.

In addition, here, the wireless communication device 1000 may detect a rotational movement of the wireless communication device 1000 according to a rotational movement of the object using the acceleration sensor and/or the gyro sensor. In this case, the rotational movement of the wireless communication device 1000 may reflect an action of the user such as opening the cap of the object for medication adherence.

In addition, here, the wireless communication device 1000 may detect a degree of inclination of the wireless communication device 1000 according to a degree of inclination of the object using the acceleration sensor, the gyro sensor, and/or the geomagnetic sensor. In this case, the degree of inclination of the wireless communication device 1000 may reflect an action of the user such as shaking or inclining the object during the medication adherence process.

Here, the motion sensor 1110 may detect a degree of a change in position, a degree of a rotational movement, or a degree of inclination of the wireless communication device 1000 attached to the object. For example, the degree of the change in position, the degree of the rotational movement, or the degree of the inclination of the wireless communication device 1000 may be reflected in an acceleration value, a gyro value, or a geomagnetic value among motion values.

The wireless communication device 1000 may determine whether the motion value satisfies the motion condition (S1200). The wireless communication device 1000 may determine whether the motion value satisfies the motion condition in order to detect the user's action of moving the object containing the medication while the user performs the medication adherence. For example, the first control unit 1400 may determine whether a motion condition to be described below is satisfied, on the basis of the motion value obtained from the motion sensor 1110.

The motion condition may be set as a condition for recognizing an action of the user taking the medication during the medication adherence process or taking out or preparing the medication before injecting the medication into the user's body.

The motion condition may include a condition in which an amount of change in the motion value is greater than or equal to a motion threshold value. For example, the motion condition may include a condition in which a difference between acceleration values obtained at different time points is greater than or equal to an acceleration threshold value, a condition in which a difference between gyro values obtained at different time points is greater than or equal to a gyro threshold value, a condition in which a difference between geomagnetic values obtained at different time points is greater than or equal to a geomagnetic threshold value, and/or a combination thereof.

Here, the motion threshold value may refer to a difference value between the motion values recognized that the wireless communication device 1000 is moved. As an example, the motion condition may be set as a case in which an amount of change in the acceleration value obtained from the acceleration sensor is 0.15 or more, and specifically, may be set as a case in which an amount of change in each of x-axis, y-axis, and z-axis values obtained from the acceleration sensor is 0.15 or more. As another example, the motion condition may be set as a case in which an amount of change in the gyro value obtained from the gyro sensor is 0.15 or more, and specifically, may be set as a case in which an amount of change in each of pitch, roll, and yaw values obtained from the gyro sensor is 0.15 or more.

Meanwhile, the motion threshold value may be set to be different according to the object to which the wireless communication device 1000 is attached. For example, in the case in which the wireless communication device 1000 is attached to the object such as a medication container, the wireless communication device 1000 may be moved relatively little or move slowly when the user takes the medication out thereof, and in the case in which the wireless communication device 1000 is attached to the object such as a medicine cabinet, the wireless communication device 1000 may be moved relatively more or move rapidly when the user takes the medication out thereof. In this case, the motion threshold value may be set to a smaller value when the wireless communication device 1000 is attached to a medicine cabinet than when the wireless communication device 1000 is attached to a medication container.

Alternatively, the motion condition may include a condition in which the motion value is greater than or equal to the motion threshold value. For example, the motion condition may include a condition in which the acceleration value is greater than or equal to the acceleration threshold value, a condition in which the gyro value is greater than or equal to the gyro threshold value, a condition in which the geomagnetic value is greater than or equal to the geomagnetic threshold value, and/or a combination thereof.

Here, the motion threshold value may be set to a minimum value recognized as the wireless communication device 1000 moving.

Meanwhile, the motion condition may be set as a condition in which the user's actions appearing in the process in which the user performs the medication adherence are sequentially detected.

For example, the motion condition may be set as a condition in which the gyro value becomes greater than or equal to the gyro threshold value after the acceleration value becomes greater than or equal to the acceleration threshold value. In this case, the motion condition may correspond to a case in which it is assumed that the user's action that should be detected by using the motion value is an action of rotating a part of the object to which the wireless communication device 1000 is attached after moving the object.

As another example, the motion condition may be set as a condition in which the acceleration value becomes greater than or equal to the acceleration threshold value after the geomagnetic value becomes greater than or equal to the geomagnetic threshold value. In this case, the motion condition may correspond to a case in which it is assumed that the user's action to be detected by using the motion value is an action of moving the object after shaking the object.

As still another example, the motion condition may be set as a condition in which the acceleration value becomes greater than or equal to the acceleration threshold value after the gyro value becomes greater than or equal to the gyro threshold value. In this case, the motion condition may correspond to a case in which it is assumed that the user's action that should be detected by using the motion value is an action of taking the medication out thereof after rotating a part of the object to which the wireless communication device 1000 is attached.

The step S1200 of determining whether the motion value satisfies the motion condition may be performed at a specific time point or at a specific time interval. As an example, the wireless communication device 1000 may determine whether the motion condition is satisfied at a time point at which a signal such as a connect request signal, a connection acknowledge request signal, a connection acknowledge signal, or a data signal is received from the wearable device 2000. As another example, the wireless communication device 1000 may determine whether the motion condition is satisfied for a predetermined time from the time point at which the above-described signal is received from the wearable device 2000. The time point of determining whether the motion condition is satisfied will be described in more detail below.

When it is determined that the motion condition is satisfied, the wireless communication device 1000 may determine whether the ambient light condition is satisfied, as will be described below. Alternatively, when it is determined that the motion condition is not satisfied, the wireless communication device 1000 may control the sensor unit 1100 so that the motion sensor 1110 is operated in a low power mode, the motion sensor 1110 is turned off, or whether the motion condition is satisfied is determined by re-obtaining the motion value from the motion sensor 1110.

The wireless communication device 1000 may obtain the ambient light value from the ambient light sensor 1120 (S1300). The ambient light value may be interpreted as a value of data reflecting the ambient light of the object to which the wireless communication device 1000 is attached by reflecting the ambient light of the wireless communication device 1000. In order to determine whether the medication adherence of the user starts, the ambient light of the object or the illuminance around the object may be checked.

Referring to FIG. 11, the object may be located in various places and the ambient light of the object may also be changed in various ways.

For example, the object may be stored in a bag or storage box for storage, and the user may go out with a bag or storage box in which the object is stored when going out. In this case, the ambient light of the object may be relatively dark.

Meanwhile, generally, when the user performs the medication adherence, the object may be located in a relatively bright place, and when the user does not perform the medication adherence, the object may be located in a relatively dark place. However, even when the user performs the medication adherence, the object may be located in the relatively dark place.

The wireless communication device 1000 may determine whether the ambient light value satisfies the ambient light condition (S1400). The wireless communication device 1000 may determine whether the ambient light condition related to the ambient light of the object is satisfied in order to check whether an environment for the medication adherence of the user is generated.

Here, the ambient light condition may be interpreted as a condition for recognizing a case in which the user does not perform the medication adherence. For example, as described above, in the case in which the user goes out with the bag in which the object is stored, even when the user does not perform the medication adherence, the object may be moved in the same manner as the case in which the user performs the medication adherence. In this case, the wireless communication device 1000 may check whether the motion condition is satisfied as well as whether the ambient light condition is satisfied to determine whether the user performs the medication adherence. Specifically, the ambient light condition may include a condition in which the ambient light value is greater than or equal to the ambient light threshold value. Here, the ambient light threshold value may be set in consideration of a brightness value that should be secured when medication adherence is performed, a brightness value that should be secured for medication classification, an average brightness value that secures a person's field of view, or the like.

Meanwhile, as illustrated in FIG. 11, even when there is no lighting around the object and the place is relatively dark, the user may perform the medication adherence. In consideration of such a situation, the above-described ambient light threshold value may be set to be very low.

The step S1400 of determining whether the ambient light value satisfies the ambient light condition may be performed at a specific time point or at a specific time interval. As an example, the wireless communication device 1000 may determine whether the ambient light condition is satisfied at a time point at which the motion condition is satisfied. As another example, the wireless communication device 1000 may determine whether the ambient light condition is satisfied for predetermined time period from the time point at which the motion condition is satisfied. The time point of determining whether the ambient light condition is satisfied will be described in more detail below.

When it is determined that the ambient light condition is satisfied, the wireless communication device 1000 may generate or change activation data as will be described below. Alternatively, when it is determined that the ambient light condition is not satisfied, the wireless communication device 1000 may control the sensor unit 1100 so that the motion sensor 1110 and/or the ambient light sensor 1120 are/is operated in a low power mode as will be described below, the motion sensor 1110 and/or the ambient light sensor 1120 are/is turned off, whether the motion condition is satisfied is determined by obtaining the motion value from the motion sensor 1110, or whether the ambient light condition is satisfied is determined by re-obtaining the ambient light value from the ambient light sensor 1120.

Even when the motion condition is satisfied, when the ambient light condition is not satisfied through the step S1400 of determining whether the ambient light value satisfies the ambient light condition, the wireless communication device 1000 may not generate activation data. Accordingly, even when the object is moved, the situation (e.g., in the case in which the user moves with a bag including the object when going out) in which the medication adherence is not performed may be distinguished. As a result, it is possible to prevent the camera module 2100 of the wearable device 2000 from being indiscriminately activated, and furthermore, to protect the privacy of the user or others.

The wireless communication device 1000 may transmit the activation data (S1500). The wireless communication device 1000 may generate or change the activation data according to a method of transmitting or receiving data with the wearable device 2000. A method of transmitting the activation data from the wireless communication device 1000 to the wearable device 2000 will be described in detail below.

Meanwhile, the order in which the above-described steps S1100 to S1400 are performed may be changed. As an example, the wireless communication device 1000 may obtain the ambient light value from the ambient light sensor 1120 to determine whether the ambient light condition is satisfied, and when it is determined that the ambient light condition is satisfied, the wireless communication device 1000 may obtain the motion value from the motion sensor 1110 to determine whether the motion value satisfies the motion condition, and when it is determined that the motion condition is satisfied, the wireless communication device 1000 may transmit the activation data. As another example, the wireless communication device 1000 may obtain the motion value and the ambient light value using the motion sensor 1110 and the ambient light sensor 1120, and when it is determined that the obtained motion value satisfies the motion condition, the wireless communication device 1000 may determine whether the ambient light value satisfies the ambient light condition, and when it is determined that the ambient light condition is satisfied, the wireless communication device 1000 may transmit the activation data.

On the other hand, at least one of the above-described steps S1100 to S1400 may be omitted. For example, the step S1300 of obtaining the ambient light value from the ambient light sensor 1120 and the step S1400 of determining whether the ambient light value satisfies the ambient light condition may be omitted. In other words, when it is determined that the motion value obtained by using the motion sensor 1110 satisfies the motion condition, the wireless communication device 1000 may generate activation data and transmit the activation data, thereby setting a time point at which the video shooting starts.

In this case, the motion condition may be set in consideration of the fact that specific movements of the user are sequentially performed during the medication adherence process.

For example, the motion condition may be set as a first condition in which the gyro value becomes greater than or equal to the gyro threshold value after the acceleration value becomes greater than or equal to the acceleration threshold value. The first condition may be a condition corresponding to a case in which the user rotates the object to which the wireless communication device 1000 is attached in order to take the medication out thereof after moving the object in performing the medication adherence.

As another example, the motion condition may be set as a second condition in which the acceleration value becomes greater than or equal to the acceleration threshold value after the gyro value becomes greater than or equal to the gyro threshold value. The second condition may be a condition corresponding to a case in which the user moves the object after rotating a portion of the object to which the wireless communication device 1000 is attached in order to take the medication out of the object in performing the medication adherence.

As still another example, the motion condition may be set as a third condition in which each of an amount of instantaneous change in acceleration value, an amount of change in acceleration value in a preset time interval, an amount of instantaneous change in gyro value, and/or an amount of change in gyro value in a preset time interval becomes greater than or equal to a corresponding threshold value.

Meanwhile, the motion condition may be set by combining at least two of the first condition, the second condition, and the third condition described above.

Hereinafter, a method of transmitting activation data in the wireless communication device 1000 will be described in detail with reference to FIGS. 12 to 14.

Figure 12:
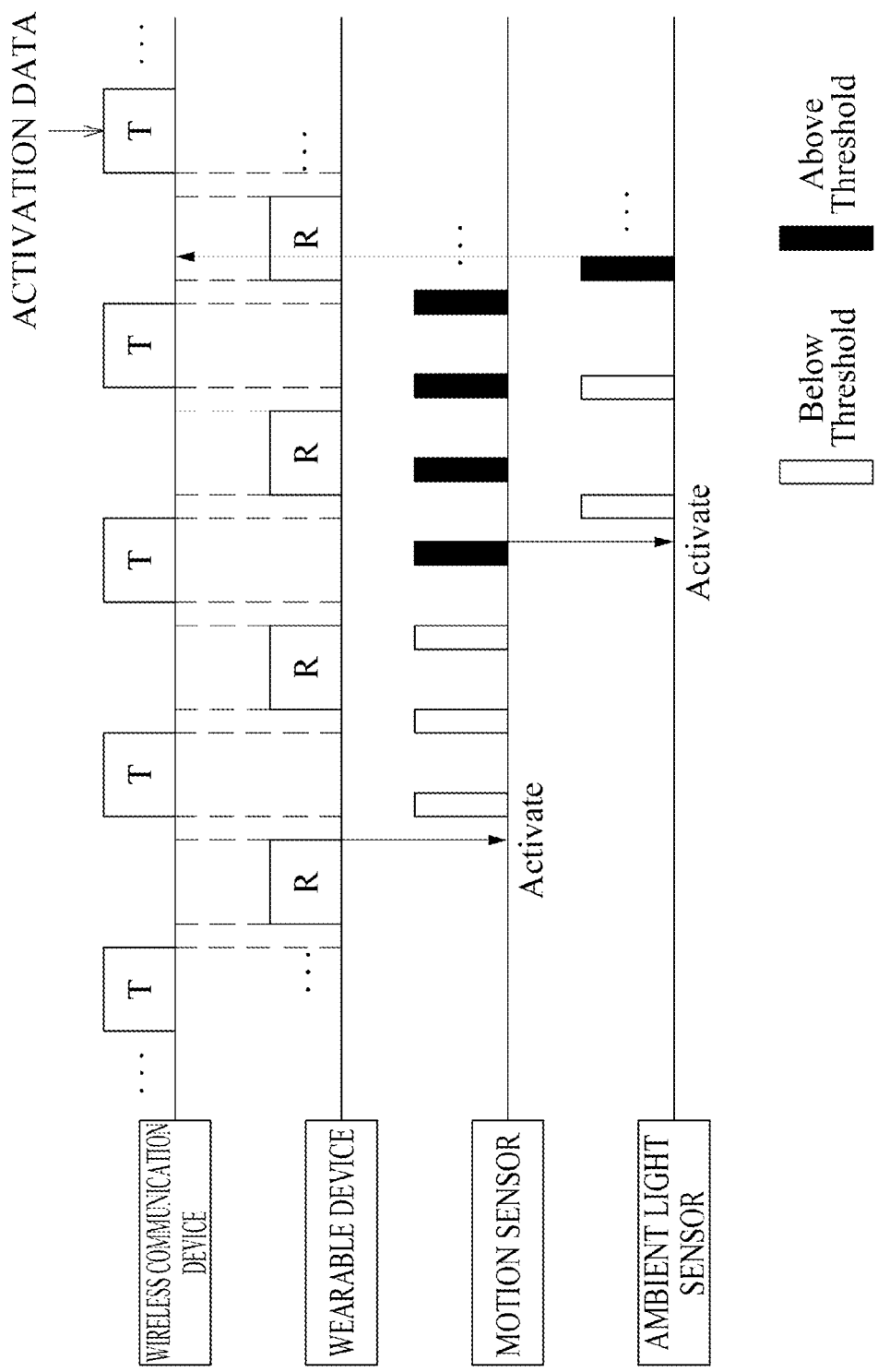
FIGS. 12 to 14 are diagrams illustrating processes of transmitting or receiving data in a medication adherence monitoring system according to an embodiment of the present invention.
Figure 13:
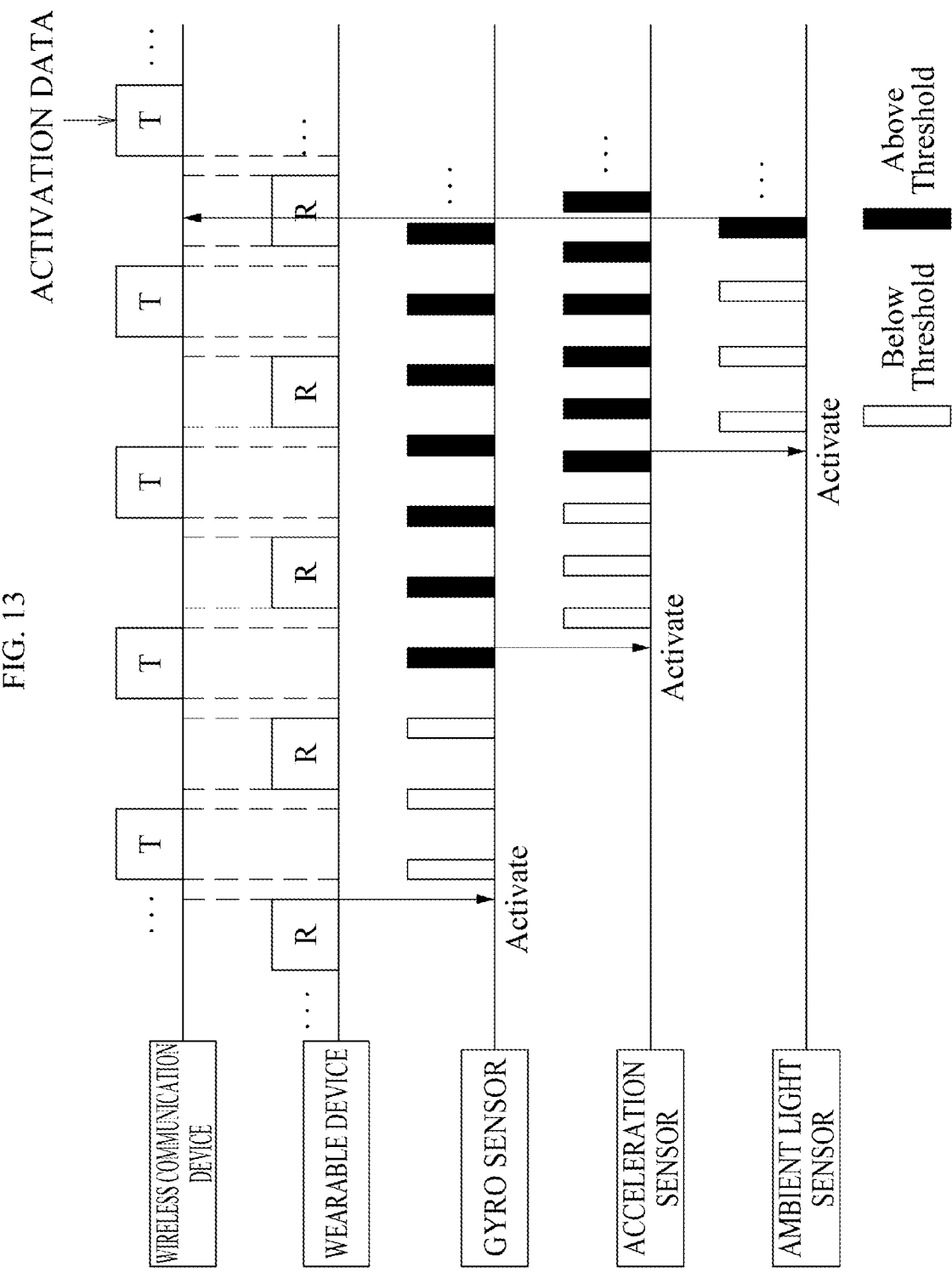
Figure 14:
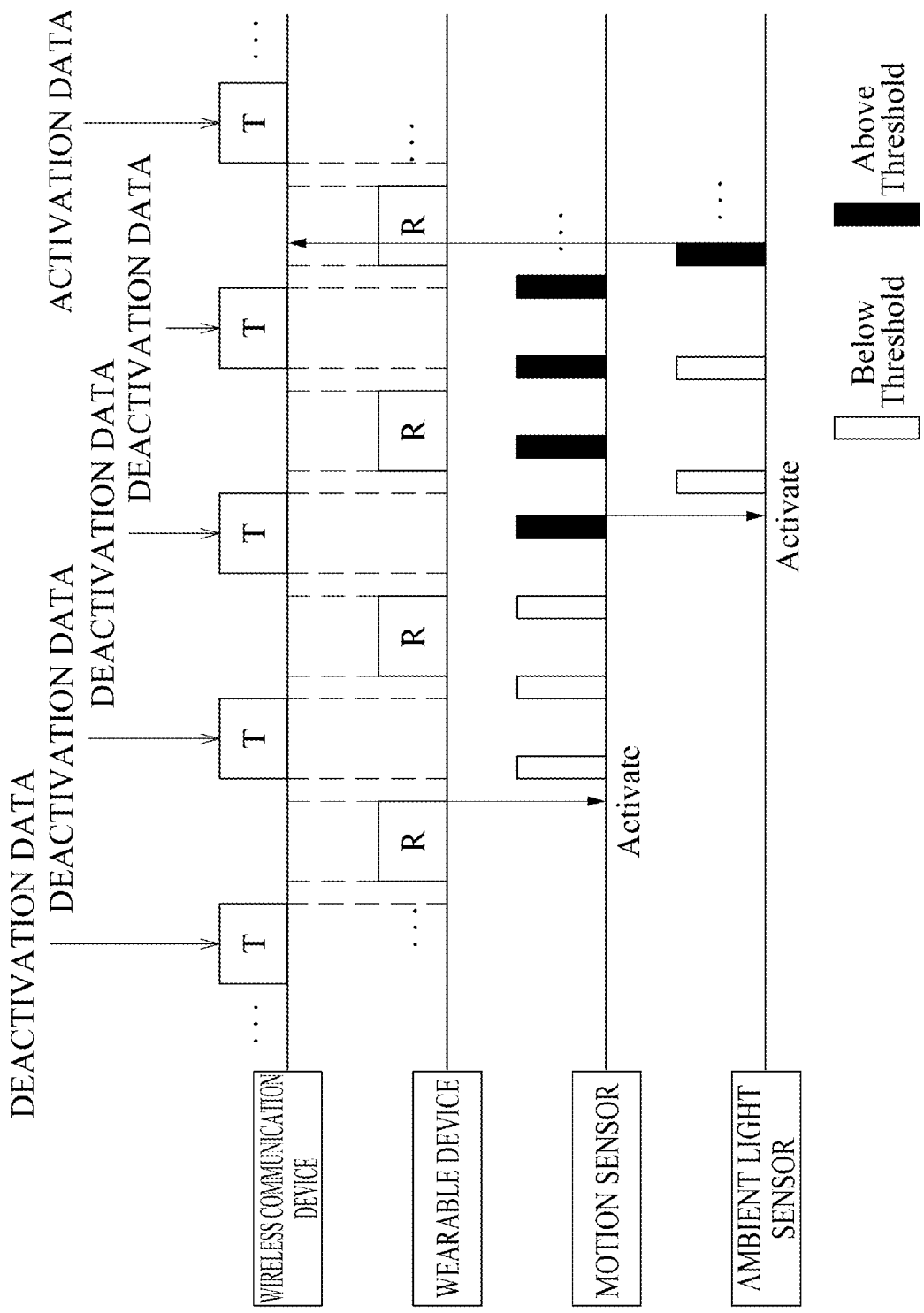

FIGS. 12 to 14 are diagrams illustrating processes of transmitting or receiving data in the medication adherence monitoring system 100 according to the embodiment of the present invention.

Referring to FIG. 12, the wireless communication device 1000 may transmit the activation data to the wearable device 2000 when the above-described motion condition and/or ambient light condition are/is satisfied. Hereinafter, the process in which the activation data is transmitted from the wireless communication device 1000 to the wearable device 2000 will be described in more detail.

The wireless communication device 1000 and the wearable device 2000 may exchange data after being connected to each other. Specifically, the wireless communication device 1000 and the wearable device 2000 may be connected to each other, the wireless communication device 1000 may transmit a signal to the wearable device 2000 at a preset period, and the wearable device 2000 may transmit a signal to the wireless communication device 1000 at a preset period.

Here, when the wearable device 2000 requests connection confirm from the wireless communication device 1000, a signal T may be a connection acknowledge signal or a data signal, a signal R may be a connection acknowledge request signal or a reception acknowledge signal indicating that the signal transmitted from the wireless communication device 1000 is received. The reception acknowledge signal might be also interpreted as a reception confirm signal which indicates confirmation of the reception.

Alternatively, when the wireless communication device 1000 requests connection confirm from the wearable device 2000, the signal T may be a connection acknowledge request signal or a data signal, and the signal R may be a connection acknowledge signal or a reception acknowledge signal indicating that the signal T is received.

Hereinafter, as the case in which the wearable device 2000 requests the connection confirm from the wireless communication device 1000, a case in which the wearable device 2000 transmits the connection acknowledge request signal or the reception acknowledge signal to the wireless communication device 1000 and the wireless communication device 1000 transmits the connection acknowledge signal or the data signal to the wearable device 2000 will be mainly described. However, the technological concept of the present invention is not limited thereto, and the above process may also be similarly applied to the case in which the wireless communication device 1000 requests the connection confirm from the wearable device 2000.

When the wireless communication device 1000 receives the signal R, the wireless communication device 1000 may obtain a motion value using the motion sensor 1110. As an example, when the first control unit 1400 receives the connection acknowledge request signal from the wearable device 2000, the first control unit 1400 may turn on or activate the motion sensor 1110 to periodically or temporarily obtain the motion value using the motion sensor 1110. As another example, when the first control unit 1400 receives the reception acknowledge signal from the wearable device 2000, the first control unit 1400 may turn on or activate the motion sensor 1110.

When the motion condition is satisfied, the wireless communication device 1000 may obtain an ambient light value using the ambient light sensor 1120. For example, when the motion value obtained by using the motion sensor 1110 becomes greater than or equal to the motion threshold value, the first control unit 1400 may turn on or activate the ambient light sensor 1110 to periodically or temporarily obtain the ambient light value using the ambient light sensor 1120.

Meanwhile, when the wireless communication device 1000 receives the signal R from the wearable device 2000, the wireless communication device 1000 may obtain the motion value and the ambient light value using the motion sensor 1110 and the ambient light sensor 1120. For example, when the first control unit 1400 receives the connection acknowledge request signal from the wearable device 2000, the first control unit 1400 may turn on or activate the motion sensor 1110 and the ambient light sensor 1120 to periodically or temporarily obtain the motion value and the ambient light value using the motion sensor 1110 and the ambient light sensor 1120.

When the motion condition and/or the ambient light condition are/is satisfied, the wireless communication device 1000 may generate activation data. As an example, when the motion value is greater than or equal to the motion threshold value and the ambient light value is greater than or equal to the ambient light threshold value, the first control unit 1400 may generate the activation data instructing activation of the camera module 2100 of the wearable device 2000 to allow the activation data to be included in a data signal transmitted to the wearable device 2000. As another example, when the motion value is greater than or equal to the motion threshold value or the ambient light value is greater than or equal to the ambient light threshold value, the first control unit 1400 may generate the activation data instructing activation of the camera module 2100 of the wearable device 2000 to allow the activation data to be included in the data signal transmitted to the wearable device 2000. Here, the activation data may be included in a data payload of the data signal. Furthermore, the data payload of the data signal may include the motion value and/or the ambient light value in addition to the activation data. Here, the wireless communication device 1000 may transmit the data signal together with the connection acknowledge signal, transmit the data signal instead of the connection acknowledge signal, or transmit the data signal separately from the connection acknowledge signal, to the wearable device 2000.

In other words, only when there is a need to shoot a video, the wireless communication device 1000 may generate the activation data to transmit the activation data to the wearable device 2000. When there is no need to shoot the video, the wireless communication device 1000 may not generate the activation data and, accordingly, the wireless communication device 1000 may transmit the data to the wearable device 2000 more rapidly.

Meanwhile, the wireless communication device 1000 may transmit an activation signal to the wearable device 2000. For example, when the motion condition and/or the ambient light condition are/is satisfied, the wireless communication device 1000 may transmit the activation signal to the wearable device 2000. Here, the activation signal may refer to a signal obtained by changing some values of data included in a signal (e.g., the connection acknowledge signal) which is transmitted from the wireless communication device 1000 to the wearable device 2000.

The above description may be similarly applied even when the motion sensor 1110 of the wireless communication device 1000 includes a plurality of sensors and sensed values are obtained at different time points. For example, referring to FIG. 13, the motion sensor 1110 may include an acceleration sensor and a gyro sensor. In this case, when the wireless communication device 1000 receives the connection acknowledge request signal or the reception acknowledge signal from the wearable device 2000, the wireless communication device 1000 may turn on or activate the gyro sensor. When the gyro value obtained by using the gyro sensor is greater than or equal to the gyro threshold value, the wireless communication device 1000 may turn on or activate the acceleration sensor, when the acceleration value obtained by using the acceleration sensor is greater than or equal to the acceleration threshold value, the wireless communication device 1000 may turn on or activate the ambient light sensor, and when the ambient light value obtained by using the ambient light sensor is greater than or equal to the ambient light threshold value, the wireless communication device 1000 may generate activation data instructing activation of the camera module 2100 of the wearable device 2000 to allow the activation data to be included in the data signal transmitted to the wearable device 2000.

Meanwhile, the wireless communication device 1000 may transmit activation data and deactivation data to the wearable device 2000. For example, referring to FIG. 14, when the motion condition and/or the ambient light condition are/is not satisfied, the wireless communication device 1000 may transmit a data signal including the deactivation data to the wearable device 2000, and when the motion condition and/or the ambient light condition are/is satisfied, the wireless communication device 1000 may transmit a data signal including the activation data to the wearable device 2000. Here, the deactivation data and the activation data may be included in the data payload of the data signal and expressed as a specific value (e.g., 0 or 1).

Meanwhile, the wireless communication device 1000 may obtain the sensed value from the sensor unit 1100 on the basis of the time point at which the signal is transmitted to the wearable device 2000. For example, when the first control unit 1400 transmits the connection acknowledge signal to the wearable device 2000, the first control unit 1400 may turn on or activate the sensor unit 1100 to obtain the sensed value, generate activation data on the basis of the obtained sensed value, and provide the activation data to the wearable device 2000.

The wireless communication device 1000 may provide the additional data to the wearable device 2000. For example, the first control unit 1400 may provide identification data, manufacturer data, motion data, ambient light data, and/or transmission strength data in addition to the activation data to the second control unit 2500 through the first communication unit 1300. The above additional data may be transmitted to the wearable device 2000 using the above-described data signal, and the wearable device 2000 may determine whether the camera module 2100 is activated by using the additional data. A method of using the additional data in the wearable device 2000 will be described below.

Hereinafter, an operating state of the wireless communication device 1000 will be described with reference to FIGS. 15 to 17. In the medication adherence monitoring system 100, the wireless communication device 1000 needs to be operated each time the user performs the medication adherence, and thus the battery needs to be efficiently managed. As will be described below, by operating the wireless communication device 1000 in various states, power consumption occurring in the wireless communication device 1000 may be reduced and the efficiency of the battery may be improved.

Figure 15:
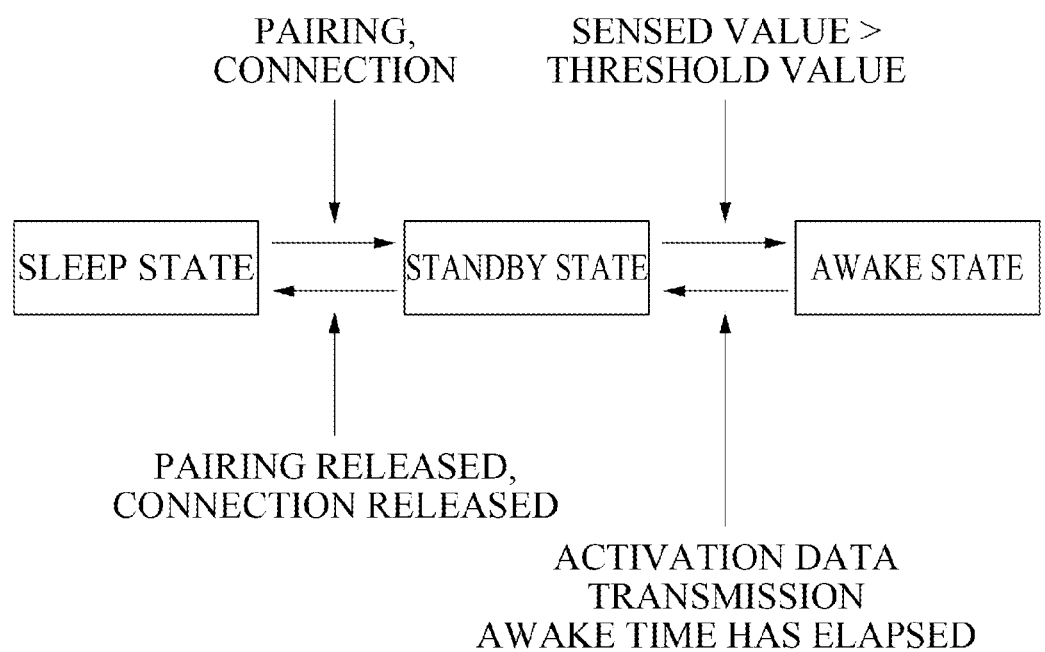
FIG. 15 is a diagram illustrating an operating state of a wireless communication device according to an embodiment of the present invention.

FIG. 15 is a diagram illustrating an operating state of a wireless communication device 1000 according to an embodiment of the present invention.

Referring to FIG. 15, the wireless communication device 1000 may be operated in a sleep state, a standby state, or an awake state.

The wireless communication device 1000 may wait for connection with the wearable device 2000 in a standby state. As an example, the first control unit 1400 may operate the sensor unit 1100 in the above-described low power mode and may not obtain the sensed value or may obtain the sensed value in a period greater than or equal to a preset period. As another example, the sensor unit 1100 may not detect the movement of the wireless communication device 1000 or the ambient light of the wireless communication device 1000. Further, in the sleep state, the first control unit 1400 may provide minimum power with which the sensor unit 1100 may not be turned off to the sensor unit 1100. The wireless communication device 1000 may be driven with relatively low power in the sleep state.

The wireless communication device 1000 may monitor the movement of the wireless communication device 1000 or an environment around the wireless communication device 1000 in the standby state. For example, the wireless communication device 1000 may obtain the sensed value by activating the sensor unit 1100 in the standby state. Specifically, the first control unit 1400 may obtain the motion value and the ambient light value by activating the motion sensor 1110 and the ambient light sensor 1120 in the standby state.

On the other hand, the wireless communication device 1000 may obtain the sensed value by activating at least a part of the sensor unit 1100 in the standby state. For example, the first control unit 1400 may activate a part of the sensor unit 1100 and may not activate another part of the sensor unit 1100. Specifically, the first control unit 1400 may activate the motion sensor 1110 and may not activate the ambient light sensor 1120.

Further, the wireless communication device 1000 may operate the sensor unit 1100 in a low power mode or a normal mode in the standby state. For example, the first control unit 1400 may operate a part of the sensor unit 1100 in the normal mode and operate another part of the sensor unit 1100 in the low power mode in the standby state. Specifically, the first control unit 1400 may operate the motion sensor 1110 in the normal mode and operate the ambient light sensor 1120 in the low power mode in the standby state. In this case, when the above-described motion condition is satisfied, the first control unit 1400 may operate the ambient light sensor 1120 in the normal mode.

As described above, only a part of the sensor unit 1100 may be selectively activated or operated in the normal mode, and thus the efficiency of the battery of the wireless communication device 1000 may be improved.

The wireless communication device 1000 may determine whether it is necessary to initiate shooting the video, in the awake state. For example, the first control unit 1400 may determine whether it is necessary to initiate shooting the video on the basis of the sensed value of the sensor unit 1100, and when it is determined that it is necessary to initiate shooting the video, the first control unit 1400 may generate activation data to provide the activation data to the wearable device 2000. More specifically, when the above-described motion condition and/or ambient light condition are/is satisfied in the awake state, the first control unit 1400 may generate the activation data to provide the activation data to the wearable device 2000.

The wireless communication device 1000 may activate at least some sensors of the sensor unit 1100 in the awake state. For example, when the wireless communication device 1000 activates the motion sensor 1110 in the sleep state or the standby state, the wireless communication device 1000 may activate the ambient light sensor 1120 in the awake state.

The operation state of the wireless communication device 1000 may be changed from the sleep state to the standby state. For example, when the wireless communication device 1000 is paired with or connected to the wearable device 2000 while being operated in the sleep state, the wireless communication device 1000 may be operated in the standby state. Specifically, when the wireless communication device 1000 and the wearable device 2000 are located within a preset distance and the first control unit 1400 receives a scan request signal, a connect request signal, a connection acknowledge request signal, or a connection acknowledge signal from the wearable device 2000 while being operated in the sleep state, the first control unit 1400 may be operated in the standby state. Such a change in the operation state may be understood to be in order to prepare for more rapidly detection of the movement of the wireless communication device 1000 or the environment around the wireless communication device 1000 when the user who wears the wearable device 2000 approaches the wireless communication device 1000 in the medication adherence of the user.

The operation state of the wireless communication device 1000 may be changed from the standby state to the awake state. For example, when the sensed value obtained by the first control unit 1400 using the sensor unit 1100 is greater than or equal to a threshold value, the first control unit 1400 may be operated in the awake state. Specifically, when the motion value obtained by the first control unit 1400 using the motion sensor 1110 in the standby state is greater than or equal to the motion threshold value, the first control unit 1400 may be operated in the awake state and may activate the ambient light sensor 1120 or obtain the ambient light value using the ambient light sensor to determine whether it is necessary to initiate shooting the video. Such a change in the operation state may be understood to be in order for more rapidly determining whether it is necessary to initiate shooting the video according to the movement of the object containing the medication while the user performs the medication adherence.

The operation state of the wireless communication device 1000 may be changed from the awake state to the standby state. As an example, when the first control unit 1400 transmits the activation data to the wearable device 2000, the first control unit 1400 may change the operation state from the awake state to the standby state. As another example, when a predetermined awake time has elapsed, the first control unit 1400 may change the operation state from the awake state to the standby state. As still another example, when the first control unit 1400 determines whether it is necessary to initiate shooting the video, the first control unit 1400 may change the operation state from the awake state to the standby state. Such a change in the operation state is to prevent unnecessary power consumption because it is not necessary to make the same determination again after determining whether it is necessary to initiate shooting the video.

The operation state of the wireless communication device 1000 may be changed from the standby state to the sleep state. For example, when the pairing or connection between the wireless communication device 1000 and the wearable device 2000 is released, the first control unit 1400 may change the operation state from the standby state to the sleep state. More specifically, when the first control unit 1400 does not receive a connection acknowledge signal, a connection acknowledge request signal, or a scan request signal from the wearable device 2000 for a predetermined time while being operated in the standby state, the first control unit 1400 may change the operation state from the standby state to the sleep state. Such a change in the operation state is to minimize power consumption of the wireless communication device 1000 when the pairing or connection between the wireless communication device 1000 and the wearable device 2000 is released.

According to an embodiment of the present invention, the wireless communication device 1000 may change the operation state as follows according to the medication adherence of the user.

When the wireless communication device 1000 does not communicate with the wearable device 2000, the wireless communication device 1000 may be operated in the sleep state. For example, when the user who wears the wearable device 2000 is located beyond a specific distance from the object to which the wireless communication device 1000 is attached and the wireless communication device 1000 is not able to communicate with the wearable device 2000, the wireless communication device 1000 may be operated in the sleep state in order to reduce power consumption. In other words, the case in which the wireless communication device 1000 is operated in the sleep state may correspond to a situation before the user performs the medication adherence or a situation in which the user is away from the object after the medication adherence is performed.

When the wireless communication device 1000 transmits or receives data to or from the wearable device 2000, the wireless communication device 1000 may be operated in a standby state. For example, when the user who wears the wearable device 2000 is located within a specific distance from the object to which the wireless communication device 1000 is attached and the wireless communication device 1000 is able to communicate with the wearable device 2000, the wireless communication device 1000 may obtain the sensed value from the sensor unit 1100 in order to detect the movement of the object. The case in which the wireless communication device 1000 is operated in the standby state may correspond to a situation in which the user approaches the object to perform the medication adherence.

When the sensed value is greater than or equal to the sensor threshold value, the wireless communication device 1000 may be operated in the awake state. For example, when the motion value obtained from the motion sensor 1110 according to the movement of the object is greater than or equal to the motion threshold value, the wireless communication device 1000 may obtain the ambient light value from the ambient light sensor 1120, and when the ambient light value is greater than or equal to the ambient light threshold value, the wireless communication device 1000 may generate the activation data to transmit the activation data to the wearable device 2000. The case in which the wireless communication device 1000 is operated in the awake state may correspond to a situation in which the user initiates the medication adherence and needs to shoot a video.

In the above, the method of transmitting or receiving the data through the pairing process and the connection process with the wearable device 2000 by the wireless communication device 1000 has been described.

On the other hand, the wireless communication device 1000 may transmit the data to the wearable device 2000 without the above-described pairing process and the connection process with the wearable device 2000, and a description thereof will be given with reference to FIG. 16.

Figure 16:
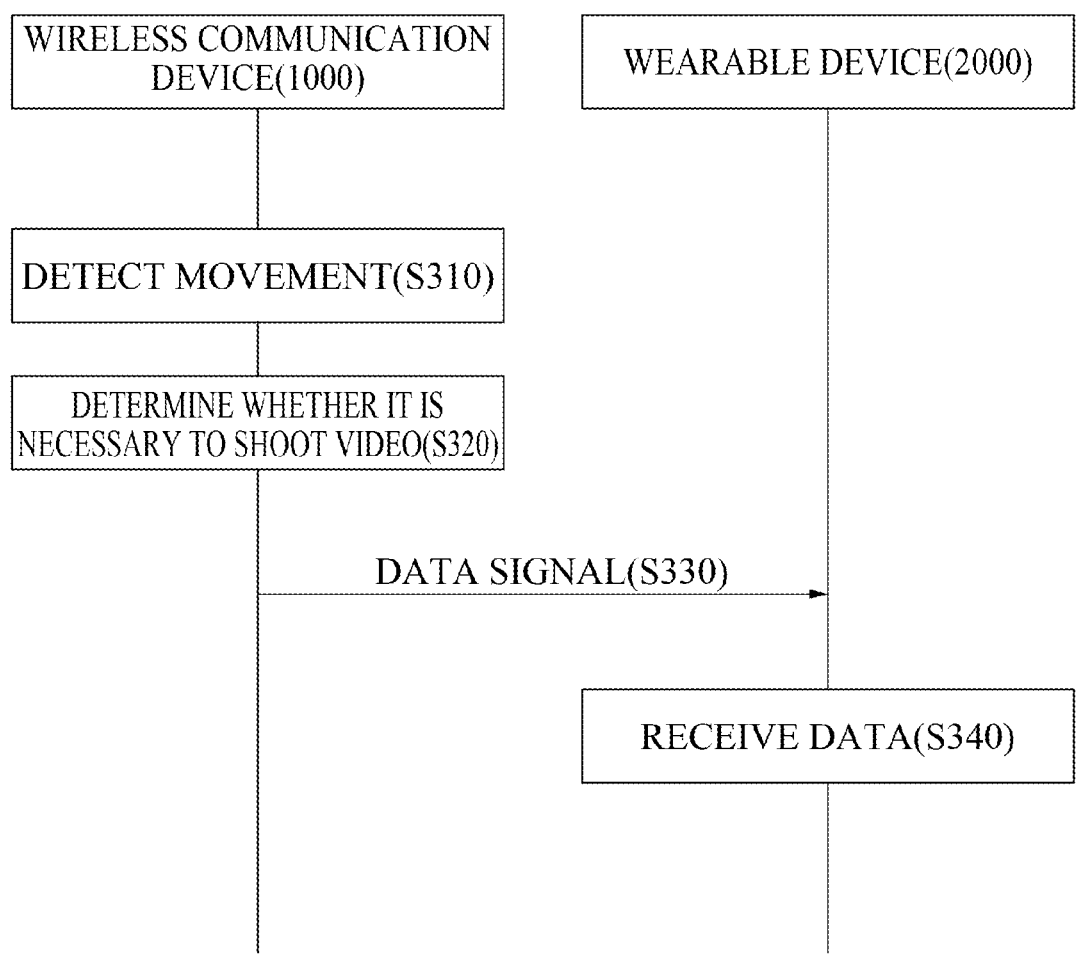
FIG. 16 is a diagram illustrating a method of transmitting data to a wearable device by a wireless communication device according to an embodiment of the present invention.

FIG. 16 is a diagram illustrating a method of transmitting data to the wearable device 2000 by the wireless communication device 1000 according to the embodiment of the present invention.

Referring to FIG. 16, the wireless communication device 1000 may transmit the data to the wearable device 2000 through a step S310 of detecting the movement of the wireless communication device 1000, a step S320 of determining whether it is necessary to shoot a video, a step S330 of transmitting a data signal to the outside, and a step S340 of receiving, by the wearable device 2000, the data.

Hereinafter, each operation will be described in detail.

The wireless communication device 1000 may detect its own movement (S310). For example, the first control unit 1400 may obtain a sensed value reflecting the movement of the wireless communication device 1000 using the motion sensor 1110. In this case, the first control unit 1400 may operate the motion sensor 1110 of the sensor unit 1100 in a normal mode and operate the ambient light sensor 1120 in a low power mode before obtaining the sensed value.

The wireless communication device 1000 may determine whether it is necessary to shoot the video (S320). For example, the first control unit 1400 may determine whether it is necessary to shoot the video on the basis of whether a motion sensed value and a sensed ambient light value obtained from the motion sensor 1110 and the ambient light sensor 1120 are greater than or equal to a motion threshold value and a ambient light threshold value, respectively. Here, the wireless communication device 1000 may operate the ambient light sensor 1120 in the normal mode in order to obtain the sensed ambient light value. The determination of whether it is necessary to shoot the video is the same as the content described in FIG. 9, and duplicate content will be omitted. When it is determined that it is necessary to shoot the video, the wireless communication device 1000 may generate activation data.

The wireless communication device 1000 may transmit the data signal to the outside (S330). For example, when it is determined that it is necessary to shoot the video, the first control unit 1400 may generate the data signal to transmit it to the outside. In this case, the data signal transmitted from the wireless communication device 1000 may not target only the wearable device 2000 and may be received by not only the wearable device 2000 but also another external device.

Here, the wireless communication device 1000 may use a data signal having the above-described advertising channel packet structure or data channel packet structure. As an example, the data signal transmitted to the outside by the first control unit 1400 may have the advertising channel packet structure and, in this case, the activation data may be included in the advertising payload. As another example, the data signal transmitted to the outside by the first control unit 1400 may have the data channel packet structure and, in this case, the activation data may be included in the data payload.

The wearable device 2000 may receive the data signal transmitted from the wireless communication device 1000. For example, the wearable device 2000 may receive the data signal by periodically receiving an external signal in a frequency band including a frequency of the data signal transmitted from the wireless communication device 1000.

Meanwhile, the wearable device 2000 may use an access address, an advertiser address, and/or a UUID included in the received data signal in order to determine whether the received data signal is the data signal transmitted from the wireless communication device 1000.

The above-described methods of transmitting or receiving data between the wireless communication device 1000 and the wearable device 2000 may minimize user intervention in the medication adherence monitoring system 100. In other words, when the user performs the medication adherence, the video of the user who performs the medication adherence may be shot by the wireless communication device 1000 and the wearable device 2000 without additional manipulation, and whether the user performs the medication adherence may be automatically determined based on the video.

Meanwhile, according to an embodiment of the present invention, the medication adherence monitoring system 100 may be implemented by using user intervention. As an example, the wireless communication device 1000 may include an input module capable of receiving an user input externally, a wireless user may provide the user input through the input module of the wireless communication device 1000 when performing the medication adherence, and the wireless communication device 1000 may transmit the activation data to the wearable device 2000 on the basis of the received user input. Here, the input module may be implemented as a physical pressing button, a touch panel, or a gesture recognition module. As another example, the wearable device 2000 may receive the user input through the input/output unit 2200 and activate the camera module 2100 on the basis of the user input.

As described above, when the user input is used in the medication adherence monitoring system 100, a time point at which the video of the user who performs the medication adherence is shot may be clearly set, and thus the accuracy of the medication adherence monitoring system 100 may be improved.

Hereinafter, the operation of the wearable device 2000 in the medication adherence monitoring system 100 will be described with reference to FIGS. 17 and 18.

Figure 17:
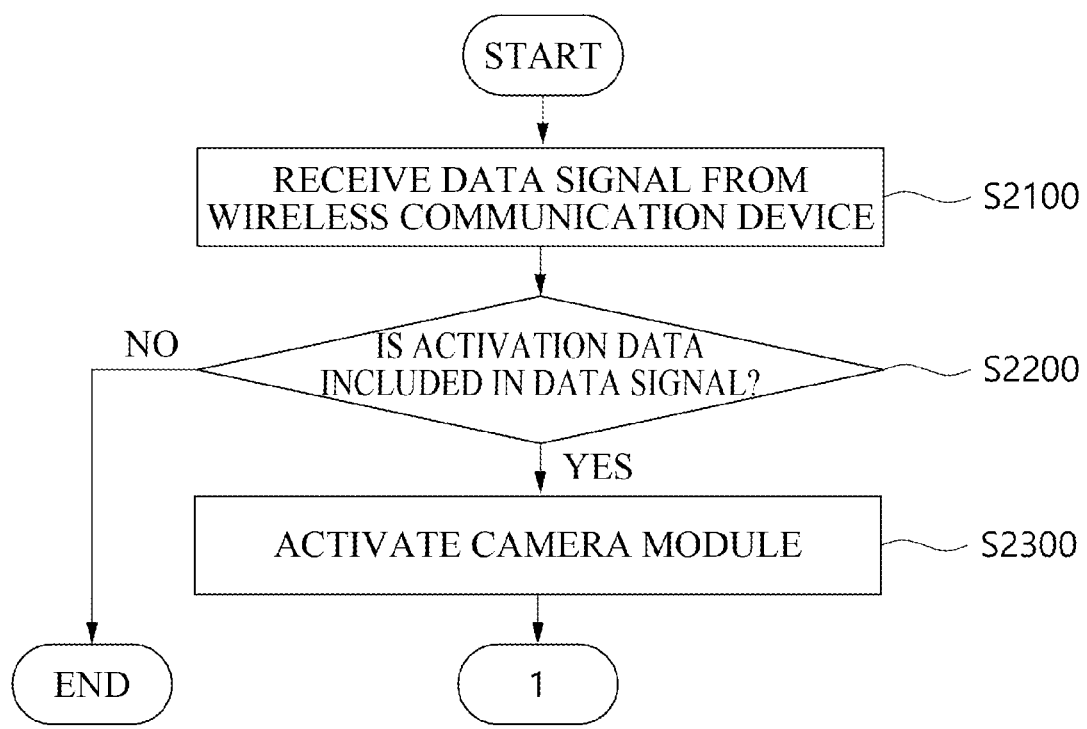
FIGS. 17 and 18 are diagrams illustrating an operation process of a wearable device in a medication adherence monitoring system according to an embodiment of the present invention.
Figure 18:
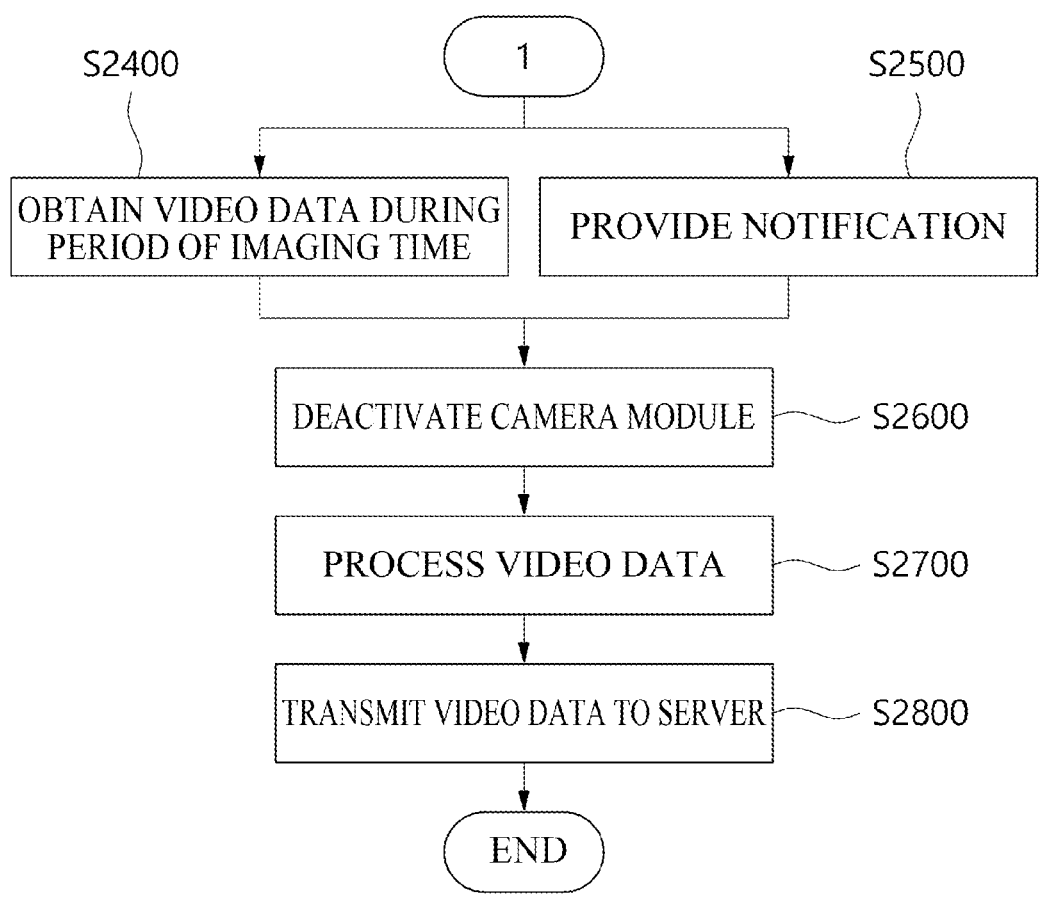

FIGS. 17 and 18 are diagrams illustrating an operation process of the wearable device 2000 in the medication adherence monitoring system 100 according to the embodiment of the present invention.

In the medication adherence monitoring system 100, the wearable device 2000 may shoot a video related to the medication adherence of the user to provide the shot video to the server 3000. In the wearable device 2000, functions such as a function of shooting a video using the signals received from the wireless communication device 1000, a function of transmitting video data obtained by shooting the video to the server 3000, and a function of preventing the video from indiscriminately being shot in situations other than the situation in which the user performs the medication adherence may be treated as important.

Referring to FIG. 17, the wearable device 2000 may perform a step S2100 of receiving a data signal from the wireless communication device 1000, a step S2200 of checking whether activation data is included in the data signal, and a step S2300 of activating the camera module 2100.

Hereinafter, each operation will be described in detail.

The wearable device 2000 may receive the data signal from the wireless communication device 1000 (S2100). For example, the second control unit 2500 may receive the data signal from the wireless communication device 1000 using the second communication unit 2400. Here, the wearable device 2000 may perform the above-described pairing process and/or connection process in order to receive the data signal from the wireless communication device 1000 or may periodically receive a signal of a specific frequency band. In addition, here, the data signal may refer to the data signal described in step S240 and, furthermore, may refer to the above-described advertising signal, scan response signal, connection acknowledge signal, and/or connection acknowledge request signal.

The wearable device 2000 may check whether the received data signal is the data signal received from the wireless communication device 1000. For example, the second control unit 2500 may compare access address, advertising address, and/or general unique identification information included in the received data signal with information pre-stored in the second memory 2300 to identify a subject that has transmitted the data signal. In this case, when the identified transmission subject is unclear or is not a data transmission/reception target, the wearable device 2000 may ignore the received data signal.

The wearable device 2000 may determine whether the activation data is included in the received data signal (S2200). For example, when it is determined that the activation data instructing activation of the camera module 2100 is included in the received data signal, the second control unit 2500 may activate the camera module 2100 as will be described below, and when it is determined that the activation data is not included, the second control unit 2500 may ignore the received data signal. Specifically, when it is determined that the activation data is included in a data payload of the received data signal, the second control unit 2500 may activate the camera module 2100, and when it is determined that the activation data is not included or the deactivation data is included, the second control unit 2500 may not activate the camera module 2100.

Meanwhile, in the case of the medication adherence monitoring system 100 implemented so that the wireless communication device 1000 transmits an activation signal to the wearable device 2000 only when the motion condition and the ambient light condition are satisfied, the second control unit 2500 may activate the camera module 2100 upon receiving the activation signal.

The wearable device 2000 may activate the camera module 2100 (S2300). For example, the second control unit 2500 may start shooting a video by activating the camera module 2100.

Referring to FIG. 18, the wearable device 2000 may perform a step S2400 of obtaining video data during an imaging time, a step S2500 of providing a notification, a step S2600 of deactivating the camera module 2100, a step S2700 of processing video data, and a step S2800 of transmitting the video data to the server 3000.

Hereinafter, each operation will be described in detail.

The wearable device 2000 may obtain the video data during the imaging time (S2400). For example, when the second control unit 2500 receives the activation data from the wireless communication device 1000, the second control unit 2500 may obtain the video data by activating the camera module 2100 and shooting the video during an imaging time which is set in a method which will be described below.

The imaging time may be set in various methods.

For example, the imaging time may be set long enough so that auxiliary actions, such as taking the medication out of the object, injecting the medication into the body, and/or drinking water for the medication adherence, may be photographed during the process in which the user performs the medication adherence. For example, the imaging time may be set in consideration of a time point at which the user performs the medication adherence. Specifically, the imaging time may be set within a range of 5 seconds to 300 seconds. Preferably, the imaging time may be set to 5 seconds, 10 seconds, 15 seconds, 20 seconds, 30 seconds, 40 seconds, 60 seconds, 90 seconds, 120 seconds, 150 seconds, 180 seconds, 210 seconds, 240 seconds, 270 seconds, 300 seconds, etc.

As another example, the imaging time may be set differently according to the type of medication adherence of the user. For example, the imaging time may be set based on the data signal received from the wireless communication device 1000. Specifically, the wearable device 2000 may identity the type of the wireless communication device 1000 on the basis of the access address, the advertising address, the general unique identification information, and/or the information included in the advertising payload or the data payload, which are included in the data signal received from the wireless communication device 1000, may determine the type of medication adherence of the user according to the identified type of the wireless communication device 1000, and set the imaging time to correspond to the type of medication adherence of the user. In this case, information about the type of medication adherence may be pre-stored in the wearable device 2000 or may be included in the data received from the server 3000.

As described above, by variously setting the imaging time, the video data related to at least a part or most of the process of the medication adherence of the user in the medication adherence monitoring system 100 may be secured.

Meanwhile, the imaging time may be set relatively short in order to secure only the video data related to a part of the process of the medication adherence of the user. For example, the imaging time may be set to secure only the video data related to a first half process (e.g., a process of taking the medication out of the object, a process of putting the medication in the user's hand, a process of bringing the medication to the user's mouth, and/or a process of putting the medication into the user's mouth) of the process of the medication adherence of the user. In this case, the video shooting may be minimized to prevent video data that infringes on the privacy of the user or surroundings from being obtained, and to reduce an amount of heat generated due to the amount of data transmission when the video data is transmitted to the server 3000 later.

The wearable device 2000 may provide a notification (S2500). For example, the second control unit 2500 may provide the notification to the user through the input/output unit 2200 while activating the camera module 2100.

The notification may include an activation notification indicating that the camera module 2100 is activated, a shooting notification indicating that a video is shot by the camera module 2100, and/or a deactivation notification indicating that the camera module 2100 is deactivated due to the end of the camera shooting. In this case, the activation notification, the shooting notification, and/or the deactivation notification may be implemented in the same way or in different ways.

The notification may be provided visually, audibly, tactilely, or a combination thereof and may be provided temporarily or periodically. As an example, the notification may be provided to the user using a display of the wearable device 2000. As another example, the notification may be provided to the user through a beep sound or vibration using a speaker of the wearable device 2000.

The above-described notification is provided to the user from the wearable device 200, and thus the user may determine whether the video is shot in the wearable device 2000 and may take measures such as deactivating the camera module 2100 through a user input when the video is being shot unnecessarily.

Meanwhile, the above-described step S2500 of providing the notification may be omitted.

The wearable device 2000 may deactivate the camera module 2100 (S2600). For example, the second control unit 2500 may deactivate the camera module 2100 when the imaging time has elapsed after activating the camera module 2100.

The wearable device 2000 may process the video data (S2700). For example, the second control unit 2500 may delete part of the video data or add data to the video data before transmitting the video data to the server 3000. Specifically, the second control unit 2500 may process the video data through correction, such as deleting a frame determined to have a privacy invasion problem among the video data obtained through video shooting or lowering the resolution. Alternatively, the second control unit 2500 may delete part of the video data in order to reduce an amount of data transmitted to the server 3000.

The step S2700 of processing the video data may be omitted.

The wearable device 2000 may transmit the video data to the server 3000 (S2800). For example, the second control unit 2500 may transmit the video data obtained through the video shooting or the processed video data to the server 3000 using the second communication unit 2400.

A time point at which the wearable device 2000 transmits the video data to the server 3000 may be variously set. As an example, the second control unit 2500 may transmit the video data to the server 3000 within a predetermined time from a time point at which the camera module 2100 is deactivated or a time point at which the video data is processed. As another example, the second control unit 2500 may transmit the video data to the server 3000 right after obtaining the video data. As still another example, the second control unit 2500 may provide the video data to the server 3000 after at least a waiting time has elapsed from the time point at which the camera module 2100 is deactivated or the time point at which the video data is processed. Here, the waiting time may be interpreted as a time required for the wearable device 2000 to lower a temperature increased due to heat generated by the video shooting in the wearable device 2000 to a certain temperature range (e.g., room temperature). For example, the waiting time may be set within a range of 5 seconds to 30 seconds.

Meanwhile, the wearable device 2000 may inquire whether to transmit the video data of the user before transmitting the video data to the server 3000. For example, the second control unit 2500 may output an inquiry message related to whether to transmit the video data to the user through the input/output unit 2200 in consideration of a time point of receiving the activation data, a time point of obtaining the video data, a previous time point of performing the medication adherence, and/or a scheduled time point of performing the medication adherence of the user. Specifically, when the time point of receiving the activation data and the time point of obtaining the video data are within a preset time from the previous time point of performing the medication adherence or are out of an error range from the scheduled time point of performing the medication adherence of the user, the second control unit 2500 may output the inquiry message.

The wearable device 2000 may or may not transmit the video data to the server 3000 according to the user response to the inquiry message.

The wearable device 2000 may delete the video data. For example, the second control unit 2500 may delete the video data stored in the second memory 2300 after transmitting the video data to the server 3000. In this case, the second control unit 2500 may delete the video data after receiving a video data reception acknowledge message from the server 3000, and when the second control unit 2500 does not receive the video data reception acknowledge message or receives an unreceived message from the server 3000, the second control unit 2500 may re-transmit the video data to the server 3000.

In the above, the case in which the activation data obtained from the wireless communication device 1000 is used when the wearable device 2000 activates the camera module 2100 has been mainly described.

Meanwhile, even when the wireless communication device 1000 determines that it is necessary to shoot the video, the user may not perform the medication adherence. In order to prevent the user from shooting the video when the user does not perform the medication adherence, the wearable device 2000 may determine whether it is necessary to additionally shoot a video. In other words, even though the user is at a certain distance from the object regardless of the medication adherence, when the object moves by another person or by sliding, etc., the wireless communication device 1000 may detect the movement of the object and transmit a signal instructing activation of the camera module 2100 by the wearable device 1000. Therefore, the wearable device 2000 may or may not activate the camera module 2100 by determining whether it is necessary to additionally shoot the video.

Hereinafter, the process of determining whether it is necessary to shoot the video prior to the activation of the camera module 2100 in the wearable device 2000 will be described with reference to FIGS. 19 to 21.

Figure 19:
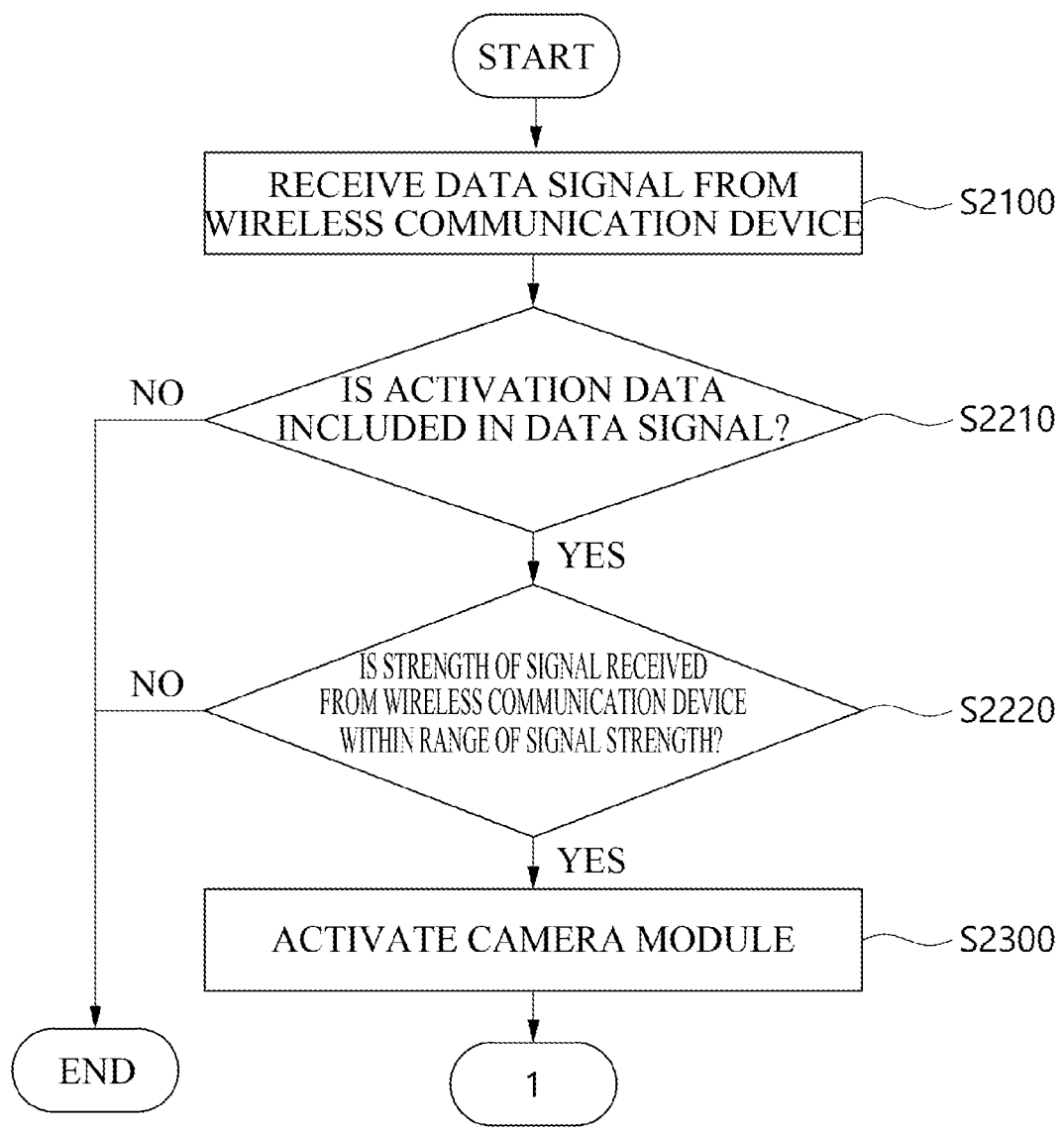
FIG. 19 is a diagram illustrating a process of activating a camera module using signal strength in a wearable device according to an embodiment of the present invention.

FIG. 19 is a diagram illustrating a process of activating the camera module 2100 using signal strength in the wearable device 2000 according to the embodiment of the present invention.

Figure 20:
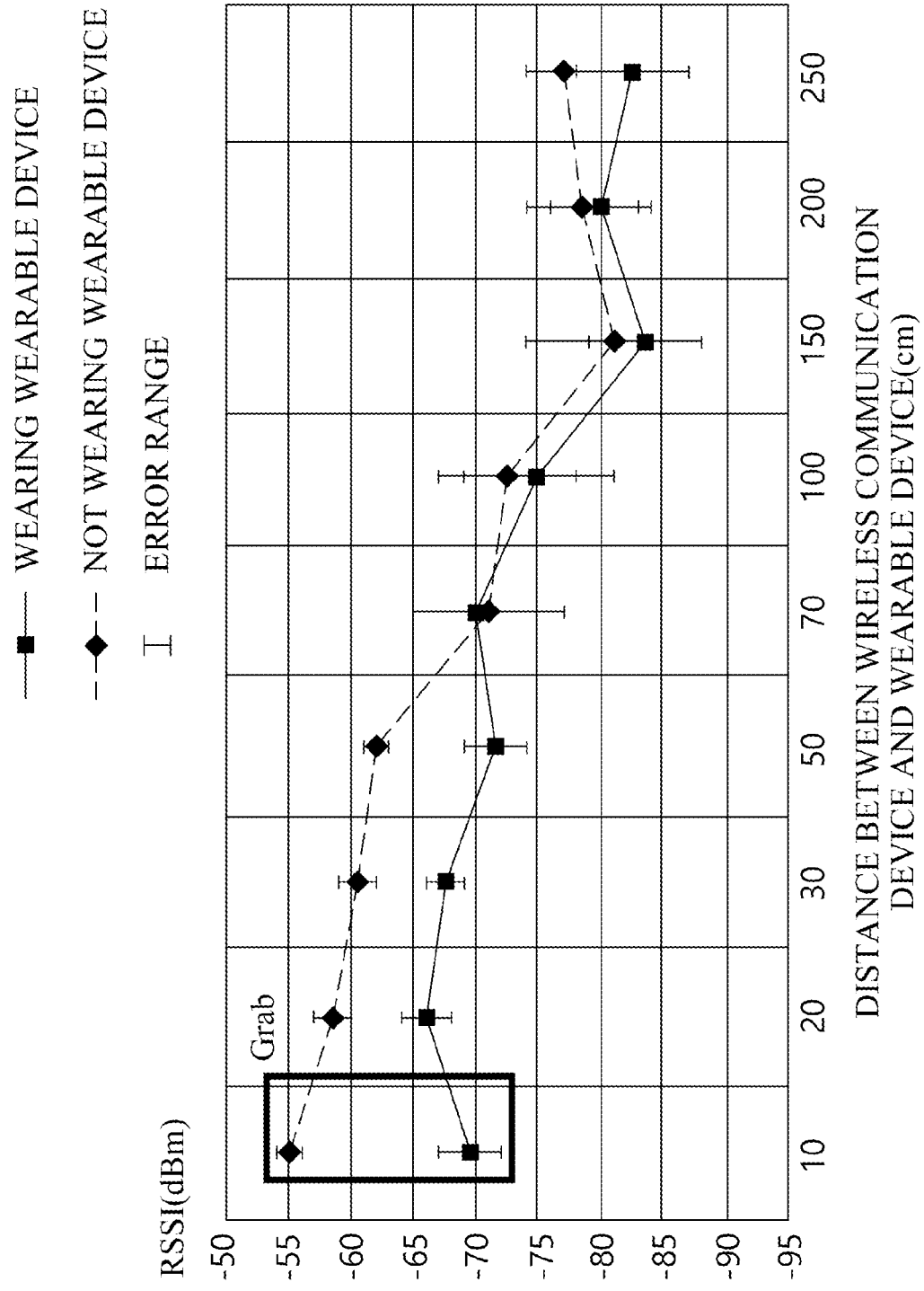
FIG. 20 is a diagram illustrating signal strength according to a distance between a wireless communication device and a wearable device according to an embodiment of the present invention.

FIG. 20 is a diagram illustrating signal strength according to a distance between the wireless communication device 1000 and the wearable device 2000 according to the embodiment of the present invention.

FIG. 21 is a diagram illustrating the strength of a signal received by the wearable device 2000 according to a place where the wireless communication device 1000 according to the embodiment of the present invention is located.

Referring to FIG. 19, the wearable device 2000 may perform a step S2100 of receiving a data signal from the wireless communication device 1000, a step S2210 of determining whether activation data is included in the data signal, a step S2220 of determining whether the strength of a signal obtained from the wireless communication device is included in a range of signal strength, and a step S2300 of activating the camera module 2100.

Here, the range of signal strength may refer to a range of reception strength of the signal received from the wireless communication device 1000 for activating the camera module 2100 by the wearable device 2000. For example, even when the wearable device 2000 obtains the activation data from the wireless communication device 1000, when the reception strength of the signal received from the wireless communication device 1000 is not included in the range of signal strength, the wearable device 2000 may not activate the camera module 2100.

Hereinafter, each operation will be described in detail.

Meanwhile, since the step S2100 of receiving the data signal from the wireless communication device 1000 and the step S2300 of activating the camera module 2100 in the wearable device 2000 are the same as those described in FIG. 16, duplicate content will be omitted.

The wearable device 2000 may determine whether the activation data is included in the received data signal (S2210). Since the present step S2210 is the same as the step S2200 described in FIG. 16, duplicate content will be omitted.

The wearable device 2000 may determine whether the strength of the signal received from the wireless communication device 1000 is included in the range of signal strength (S2220). For example, the second control unit 2500 may determine whether a received signal strength indicator (RSSI) value of the signal received from the wireless communication device 1000 is within the range of signal strength. When it is determined that the RSSI value is included in the range of signal strength, the process may proceed to the step S2300 of activating the camera module 2100, and when it is determined that the RSSI value is not included in the range of signal strength, the activation data obtained from the wireless communication device 1000 may be ignored.

Here, the signal received from the wireless communication device 1000 may include at least one of the above-described advertising signal, scan response signal, connection acknowledge signal, connection acknowledge request signal, and/or data signal. As an example, the wearable device 2000 may determine whether the RSSI value of the advertising signal received from the wireless communication device 1000 is within the range of signal strength. As another example, the wearable device 2000 may determine whether the RSSI value of the data signal received from the wireless communication device 1000 is within the range of signal strength. As still another example, the wearable device 2000 may determine whether the strength of each of the signals received from the wireless communication device 1000 or an average value thereof is within the range of signal strength in a preset time interval from the time point at which the data signal is received from the wireless communication device 1000.

The range of signal strength may be set in consideration of the signal strength according to the distance between the wireless communication device 1000 and the wearable device 2000. Specifically, the range of signal strength may be set in consideration of a change in the signal strength corresponding to a change in the distance between the wireless communication device 1000 which is attached to the object containing the medication and the wearable device 2000 which is worn on at least a part of the user's body in the process in which the user performs the medication adherence.

Referring to FIG. 20, the strength of the signal from the wireless communication device 1000 which is received by the wearable device 2000 may be changed according to a positional relationship between the wireless communication device 1000 and the wearable device 2000. In other words, the strength of the signal received by the wearable device 2000 may be changed according to a degree in which the user approaches the object in which the medication is stored for the medication adherence. As an example, when the distance between the wearable device 2000 which is worn on the user and the wireless communication device 1000 is changed from 10 cm to 250 cm, the RSSI value measured by the wearable device 2000 may have a value between −54 dBm to −81 dBMm. As another example, when the distance between the wearable device 2000 which is not worn on the user and the wireless communication device 1000 is changed from 10 cm to 250 cm, the RSSI value measured by the wearable device 2000 may have a value between −64 dBm to −88 dBMm.

As illustrated in FIG. 20, the RSSI value of the signal received by the wearable device 2000 may be changed according to whether the user performs the medication adherence or according to the process of the medication adherence of the user. Therefore, the range of signal strength should be set in consideration of the RSSI value changed according to the situation.

For example, the range of signal strength may be set to −90 dBm or higher. Referring to FIG. 20, when the RSSI value is less than −90 dBm, the distance between the wireless communication device 1000 and the wearable device 2000 may exceed about 250 cm, and thus this case may correspond to the case in which the user does not perform the medication adherence. Further, when the RSSI value is greater than or equal to −90 dBm and less than −70 dBm, the distance between the wireless communication device 1000 and the wearable device 2000 is within a range of about 70 cm to 200 cm, this case may correspond to the case in which the user approaches the object in which the medication is stored for the medication adherence or the user is located close to the object in which the medication is stored, and thus this case may be interpreted as being unclear whether the user performs the medication adherence. Therefore, when the range of signal strength is set to −90 dBm or higher, even when the possibility of the medication adherence of the user is low, the wearable device 2000 may shoot a video. Therefore, in most cases, the case of not shooting the video even through the user performs the medication adherence may be excluded. In other words, the wearable device 2000 may obtain the video data for analyzing whether the medication adherence is performed when most users perform the medication adherence, and thus it has a critical significance that the range of signal strength is set to −90 dBm or higher.

As another example, the range of signal strength may be set to −70 dBm or higher. Referring to FIG. 20, when the RSSI value is greater than or equal to −70 dBm and less than −50 dBm, the distance between the wireless communication device 1000 and the wearable device 2000 is within a range of about 10 cm to 100 cm, this case may correspond to the case in which the user sufficiently approaches the object in which the medication is stored, and thus this case may be interpreted as the probability of the medication adherence of the user is high. Therefore, when the range of signal strength is set to −70 dBm or higher, the wearable device 2000 may shoot the video when the possibility of the medication adherence of the user is high, and thus a situation may be prevented in which the video is shot even when the user does not perform the medication adherence. In other words, the wearable device 2000 mainly shoots the video when the user performs the medication adherence, unnecessary video shooting by the wearable device 2000 is prevented, and further, battery power consumption of the wearable device 2000 due to the unnecessary video shooting is prevented, and thus it has a critical significance that the range of signal strength is set to −70 dBm or higher.

As described above, the range of signal strength may be set to be a specific reference value or higher, and the range of signal strength may be selected in a range of −120 dBm to −60 dBm in consideration of critical significance. More preferably, the specific reference value may be selected in a range of −100 dBm to −80 dBm.

The range of signal strength may be set to a specific range having an upper limit value and a lower limit value.

For example, the range of signal strength may be set to a range of −70 dBm to −50 dBm. Referring to FIG. 20, when the RSSI value is set to −50 dBm or higher, the distance between the wireless communication device 1000 and the wearable device 2000 is about 10 cm or less, this case may correspond to the case in which the object to which the wireless communication device 1000 is attached and the wearable device 2000 are located very close, and thus this case may be interpreted as a state in which the wireless communication device 1000 and the wearable device 2000 are stored together. Therefore, when the range of signal strength is set to a range of −70 dBm to −50 dBm, the wearable device 2000 may shoot the video in a situation in which the user is likely to perform the medication adherence, but may not shoot the video in a situation in which the wireless communication device 1000 and the wearable device 2000 are placed abnormally close enough that it is impossible for the user to perform the medication adherence. As a result, the wearable device 2000 shoots the video when the user performs the medication adherence, but does not shoot the video in an exceptional situation in which the user does not perform the medication adherence even when the wireless communication device 1000 and the wearable device 2000 are placed close together, and thus it has a critical significance that the range of signal strength is set to a range of −70 dBm to −50 dBm.

Meanwhile, the range of signal strength may be set in consideration of the signal strength when the wearable device 2000 worn by the user receives the signal from the wireless communication device 1000 attached to the object when the object in which the medication is stored is held.

For example, as illustrated in FIG. 20, when the user grabs the object, the distance between the wireless communication device 1000 and the wearable device 2000 is about 10 cm and the RSSI value of the signal received by the wearable device 2000 is in a range of about −56 dBm to −54 dBm, and thus the range of signal strength may be set to −60 dBm or higher. In this case, considering that the average length of a person's hand is about 17 cm to 20 cm (male) or about 15 cm to 18 cm (female) and the average length of a person's palm is about 7 cm to 9 cm (male) or about 6 cm to 8 cm (female), a length of 10 cm may be understood as the distance between the wireless communication device 1000 and the wearable device 2000 when the user grabs the object, and thus it has a critical significance that the range of signal strength is set to −60 dBm or higher in consideration of the above lengths.

As another example, as illustrated in FIG. 20, the range of signal strength may be set in consideration of the fact that the signal strength is changed according to whether the wearable device 2000 is worn by the user. For example, the range of signal strength may be set to −75 dBm or higher.

As still another example, considering that the position where the wearable device 2000 is worn may be different for each user, the range of signal strength may be set based on the case in which the distance between the wireless communication device 1000 and the wearable device 2000 is within a certain distance. For example, when the distance between the wireless communication device 1000 and the wearable device 2000 is about 70 cm, the range of signal strength may be set to −75 dBm or higher or −80 dBm or higher in consideration of the RSSI value of the signal received by the wearable device 2000.

The range of signal strength may be set in consideration of places where the wireless communication device 1000 and/or the wearable device 2000 are/is located and of the strength of the signal received by the wearable device 2000.

The strength of the signal received by the wearable device 2000 may vary according to the place where the wireless communication device 1000 is located. Considering that the place where the user performs the medication adherence is not constant and may be changed, referring to a table of FIG. 20, the range of signal strength may be set to −80 dBm or higher.

Meanwhile, in setting the above-described signal strength and the range of signal strength, the signal transmission strength of the wireless communication device 1000 may be considered. As an example, the wireless communication device 1000 may adjust the transmission strength (Tx Power) of the signal transmitted to the outside, and the wearable device 2000 may set the range of signal strength in consideration of the transmission strength included in the data signal received from the wireless communication device 1000. As another example, the transmission strength of the wireless communication device 1000 may be set so that the range of signal strength is set to the above-described value in the wearable device 2000.

In the above, in determining whether the range of the strength of the signal from the wireless communication device 1000 which is received the wearable device 2000 is included in the range of signal strength, the method of setting the range of signal strength has been described. As described above, by activating the camera module 2100 in consideration of the strength of the signal received by the wearable device 2000, even when the user does not perform the medication adherence and the wireless communication device 1000 transmits the activation data to the wearable device 2000 (e.g., when another person moves the object while the user is away from the object where the medication is stored, or when the wearable device 2000 and the wireless communication device 1000 are moved while being placed close together, etc.), the video may be prevented from being taken unnecessarily.

Meanwhile, before activating the camera module 2100, the wearable device 2000 may determine whether conditions other than the above-described signal strength are satisfied. As an example, the wearable device 2000 may determine whether the wireless communication device 1000 corresponds to the object in which the medication is stored, on the basis of the access address, the general unique identification information, and the advertising address included in the data signal received from the wireless communication device 1000, and/or the data included in the advertising payload or the data payload. As another example, when the sensed value obtained by using the sensor unit 1100 of the wireless communication device 1000 is included in the received signal, the wearable device 2000 may determine whether it is necessary to shoot the video by determining whether the above-described motion condition and/or the ambient light condition are/is satisfied by using the sensed value. When the wearable device 2000 uses the sensed value, the step S2210 of determining whether the activation data is included in the data signal may be omitted.

The wearable device 2000 may provide a result of monitoring the medication adherence of the user to the user. For example, the wearable device 2000 may receive the result of monitoring the medication adherence from the server 3000 and output the result of monitoring the medication adherence to the user using the input/output unit 2200. Specifically, the wearable device 2000 may provide information on whether the user performs the medication adherence and/or a time point at which the medication adherence is performed to the user using the input/output unit 2200. Furthermore, the wearable device 2000 may provide information related to the medication adherence, such as a type of the medication, history of the medication adherence, compliance of the medication adherence, and/or information (e.g., medication effects, symptoms, side effects, etc.) about the medication being adhered to by the user.

Here, the server 3000 may receive the video data from the wearable device 2000, calculate the result of monitoring the medication adherence, and provide the monitoring result to the wearable device 2000. Detailed descriptions thereof will be described below.

Meanwhile, the result of monitoring the medication adherence and the information related to the medication adherence, which are described above, may be provided to the user through the terminal device 4000. Further, the result of monitoring the medication adherence and the information related to the medication adherence, which are described above, for managing the medication adherence of the user may be provided to medical personnel, a manager, or a guardian.

The wearable device 2000 may provide a duplicate medication notification to the user.

When the user has severe forgetfulness or suffers from a mental illness such as dementia, the user may perform the medication adherence in duplicate, and thus the wearable device 2000 may provide the duplicate medication notification to prevent the user from taking an excessive amount of medication.

The wearable device 2000 may determine whether the user performs the medication adherence in duplicate. For example, when the wearable device 2000 receives the result of monitoring the medication adherence of the user from the server 3000, the wearable device 2000 may determine whether the user performs the medication adherence in duplicate on the basis of a period at which the user performs the medication adherence. Specifically, when the time point at which the user performs the medication adherence, which is included in the result of monitoring the medication adherence received from the server 3000, is within a time described in the medication instruction from the time point when it is determined that the medication adherence has been most recently performed, the wearable device 2000 may determine that the user has performed the medication adherence in duplicate. In other words, the wearable device 2000 may obtain and store the information on whether the medication adherence is performed and the information about the time point at which the medication adherence is performed from the server 3000, and may compare the time point at which the user performs the medication adherence with the time point at which the medication adherence is to be performed to determine whether the user performs the medication adherence in duplicate. In this case, the wearable device 2000 may receive the time point at which the user performs the medication adherence and the information on how to take the medication from the server 3000.

The wearable device 2000 may provide the duplicate medication notification when the user performs the medication adherence in duplicate. For example, when it is determined that the user performs the medication adherence in duplicate, the wearable device 2000 may provide a notification indicating that the medication has been duplicated.

The wearable device 2000 may determine whether the user intends to perform the medication adherence in duplicate. For example, when the wearable device 2000 receives the activation data from the wireless communication device 1000, the wearable device 2000 may determine whether the user intends to perform the medication adherence in duplicate by comparing the time point at which the activation data is received with the time point at which the user has performed the medication adherence in the past. Specifically, when the time point at which the wearable device 2000 receives the activation data from the wireless communication device 1000 is within the time described in the medication instruction from the time point when it is determined that the medication adherence has been most recently performed, the wearable device 2000 may determine that the user intends to perform the medication adherence in duplicate. In this case, the wearable device 2000 may receive the time point at which the user performs the medication adherence and the information on how to take the medication from the server 3000.

The wearable device 2000 may provide a duplicate medication warning notification in order to prevent the user from performing the medication adherence in duplicate. For example, when it is determined that the user intends to perform the medication adherence in duplicate, the wearable device 2000 may provide a notification to warn the user of the duplicate medication.

Meanwhile, the above-described duplicate medication notification or duplicate medication warning notification may be provided to medical personnel, a manager, or a guardian in addition to the user.

Further, the process of determining whether the duplicate medication is performed or process of estimating the duplicate medication, which is described above, may be performed in the server 3000.

Hereinafter, the operation of the server 3000 in the medication adherence monitoring system 100 will be described with reference to FIGS. 22 and 23.

Meanwhile, the server 3000 may be divided into an analysis server that analyzes data and a management server that manages data according to its role, and the server 3000 described below may be understood as an analysis server.

Figure 22:
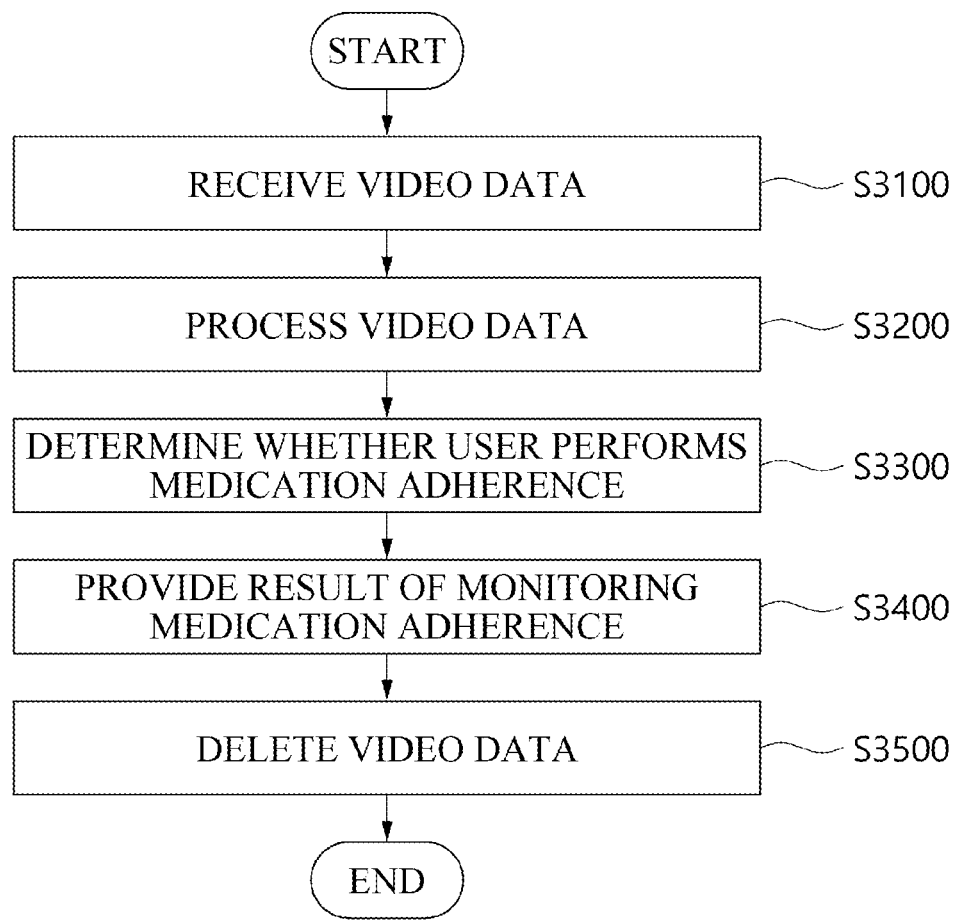
FIG. 22 is a diagram illustrating an operation process of a server according to an embodiment of the present invention.

FIG. 22 is a diagram illustrating an operation process of the server 3000 according to the embodiment of the present invention.

Referring to FIG. 22, the server 3000 may perform a step S3100 of receiving video data, a step S3200 of processing the video data, a step S3300 of determining whether the user performs medication adherence, a step S3400 of providing a result of monitoring the medication adherence, and a step S3500 of deleting the video data.

Hereinafter, each operation will be described in detail.

The server 3000 may receive the video data (S3100). For example, the server 3000 may receive the video data from wearable device 2000 through wired and/or wireless communication.

The server 3000 may process the video data (S3200). For example, the server 3000 may process the video data according to an input data format of an artificial neural network for video data analysis, which will be described below. Specifically, part of the video data may be deleted or null data may be added.

The server 3000 may process the video data to protect the privacy of the user. For example, the server 3000 may process the video data through correction, such as deleting a frame determined to have a privacy invasion problem among the video data or lowering the resolution.

The server 3000 may process the video data to show the video related to medication adherence of the user to the user or the like. For example, the server 3000 may extract a frame (e.g., a frame related to a process of taking the medication out of the object, a process of putting the medication in the user's hand, a process of bringing the medication to the user's mouth, and/or a process of putting the medication into the user's mouth) related to the process in which the user performs the medication adherence from among the video data to provide the frame to the user or the like.

The step S3200 of processing the video data by the server 3000 may be omitted.

The server 3000 may determine whether the user performs the medication adherence (S3300). For example, the server 3000 may determine whether the medication adherence is performed by analyzing the video data obtained from the wearable device 2000 using deep learning-based image analysis algorithms or artificial neural networks, such as a machine learning algorithm, Convolution Neural Network (CNN), Region based Convolution Neural Network (R-CNN), Recurrent Neural Network (RNN), Fast R-CNN, Faster R-CNN, Long Short Term Memory network (LSTM), Residual Network (ResNet), You Only Look Once (YOLO), Generative Adversarial Network (GAN), and the like. A method of determining whether the medication adherence is performed in the server 3000 will be described in detail below.

The server 3000 may provide data on the result of monitoring the medication adherence (S3400). As an example, the server 3000 may transmit data on whether the user performs the medication adherence to the wireless communication device 1000, the wearable device 2000, and/or the terminal device 4000. As another example, the server 3000 may transmit the data on the result of monitoring the medication adherence to a management server that manages data for the medication adherence of the user.

The server 3000 may delete the video data (S3500). For example, the server 3000 may delete the video data received from the wearable device 2000 and/or the video data obtained by processing the video data when it is determined whether the user performs the medication adherence by analyzing the video data. The server 3000 may prevent the privacy of the user or others due to preservation of the video data from being invaded by deleting the video data after analyzing the video data. However, when the video data needs to be stored, such as having a need to provide the video data to the user or the like, this step S3500 may be omitted.

The server 3000 may use various methods as described above in determining whether the medication adherence is performed. Hereinafter, a method of analyzing video data using an artificial neural network in the server 3000 will be mainly described with reference to FIG. 23, but the technological concept of the present invention is not limited thereto.

Figure 23:
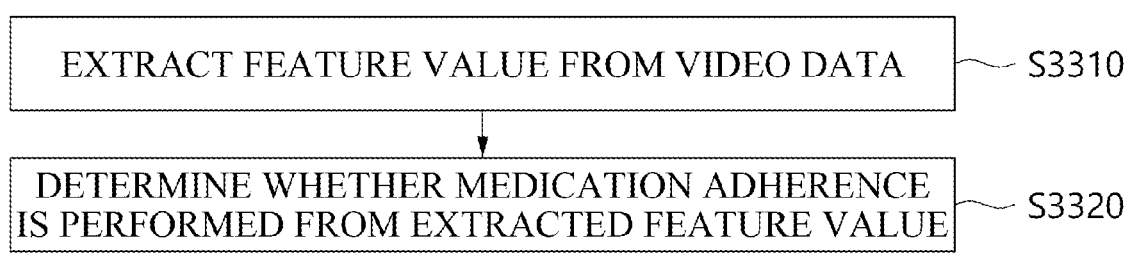
FIG. 23 is a diagram illustrating a process of analyzing video data in a server according to an embodiment of the present invention.

FIG. 23 is a diagram illustrating a process of analyzing the video data in the server 3000 according to the embodiment of the present invention.

Referring to FIG. 23, the step S3300 of determining whether the user performs the medication adherence may include a step S3310 of extracting a feature value from the video data and a step S3320 of determining whether the medication adherence is performed by using the extracted feature value.

The server 3000 may extract the feature value from the video data (S3310). For example, the server 3000 may extract the feature value from the video data obtained from the wearable device 2000 using a detection model.

The feature value may refer to a value indicating whether a major feature is included in the medication adherence process. For example, the feature value may refer to a value indicating whether a video or an image includes the medication, the object, the user's hand, the user's mouth, the user's hand holding the object, the hand holding the medication, and/or an action of putting the medication into the mouth.

In other words, the server 3000 may input the video data to the detection model to detect an object and motion related to the medication adherence included for each frame included in the video data. The server 3000 may detect the object and motion for all or part of the image frames included in the video data. The fact that the server 3000 inputs the video data to the detection model to detect the object related to the medication adherence may mean that the server 3000 determines whether the object related to the medication adherence is present in the video data, and the fact that the server 3000 inputs the video data to the detection model to detect the motion related to the medication adherence may mean that the server 3000 determines whether the motion related to the medication adherence is present in the video data.

The detection model may refer to an artificial neural network that is trained to receive video data and extract feature values. For example, the detection model may be an artificial neural network trained with a data set labeled with feature values on a video related to medication adherence. Specifically, the data set for training the detection model may include data obtained by shooting a plurality of videos related to medication adherence and labeling the object and motion related to the medication adherence for each image frame included in each video. The detection model may be implemented with the above-described deep learning-based image analysis algorithm.

The server 3000 may determine whether the medication adherence is performed by using the extracted feature value (S3320). For example, the server 3000 may determine whether the user performs the medication adherence from the extracted feature value using a confirmation model. Specifically, the server 3000 may obtain an output value indicating whether the user performs the medication adherence by inputting the image frame of the above-described video data and the feature value extracted from each image frame as it is or by processing and inputting the image frame and the feature value into the confirmation model.

Here, the confirmation model may refer to an artificial neural network that is trained to receive the feature value and output the value indicating whether the medication adherence is performed. For example, the confirmation model may be an artificial neural network trained with the data set labeled with whether the medication adherence is performed on the feature values for each video data frame. Specifically, the data set for training the confirmation model may include the data in which the image frame and the feature value corresponding thereto are labeled with the value indicating whether or not the medication adherence is performed. The confirmation model may be implemented with the above-described deep learning-based image analysis algorithm.

In the above, the operation of the medication adherence monitoring system 100 has been described.

Meanwhile, the method and process of performing the medication adherence may vary for each person. As an example, a time required for performing the medication adherence may vary for each user, and some users may perform the medication adherence for a time significantly exceeding an average time expected as a time required for the medication adherence. As another example, in the case of taking multiple medications for medication adherence, all medications may be taken at one time or the medications may be taken several times one by one, according to the user.

As described above, since the method or process of performing the medication adherence may be different for each user, the medication adherence monitoring system 100 needs to be operated in consideration of a specific situation as follows.

Hereinafter, the operation of the medication adherence monitoring system 100 when the user moves the object while shooting the video will be described with reference to FIGS. 24 to 28.

Figure 24:
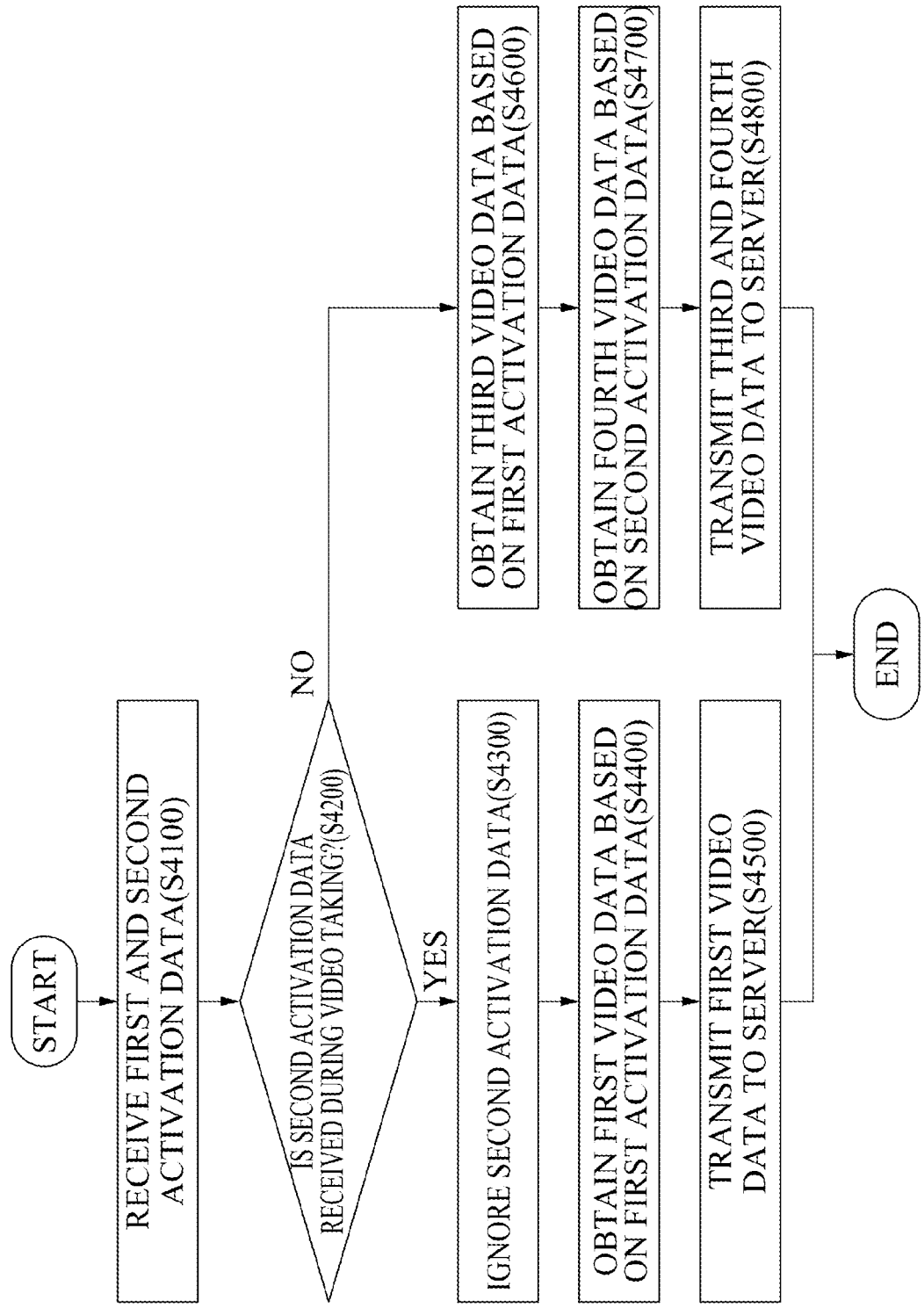
FIGS. 24 and 25 are diagrams illustrating operation processes performed by a wearable device when a user moves an object while shooting a video according to an embodiment of the present invention.
Figure 25:
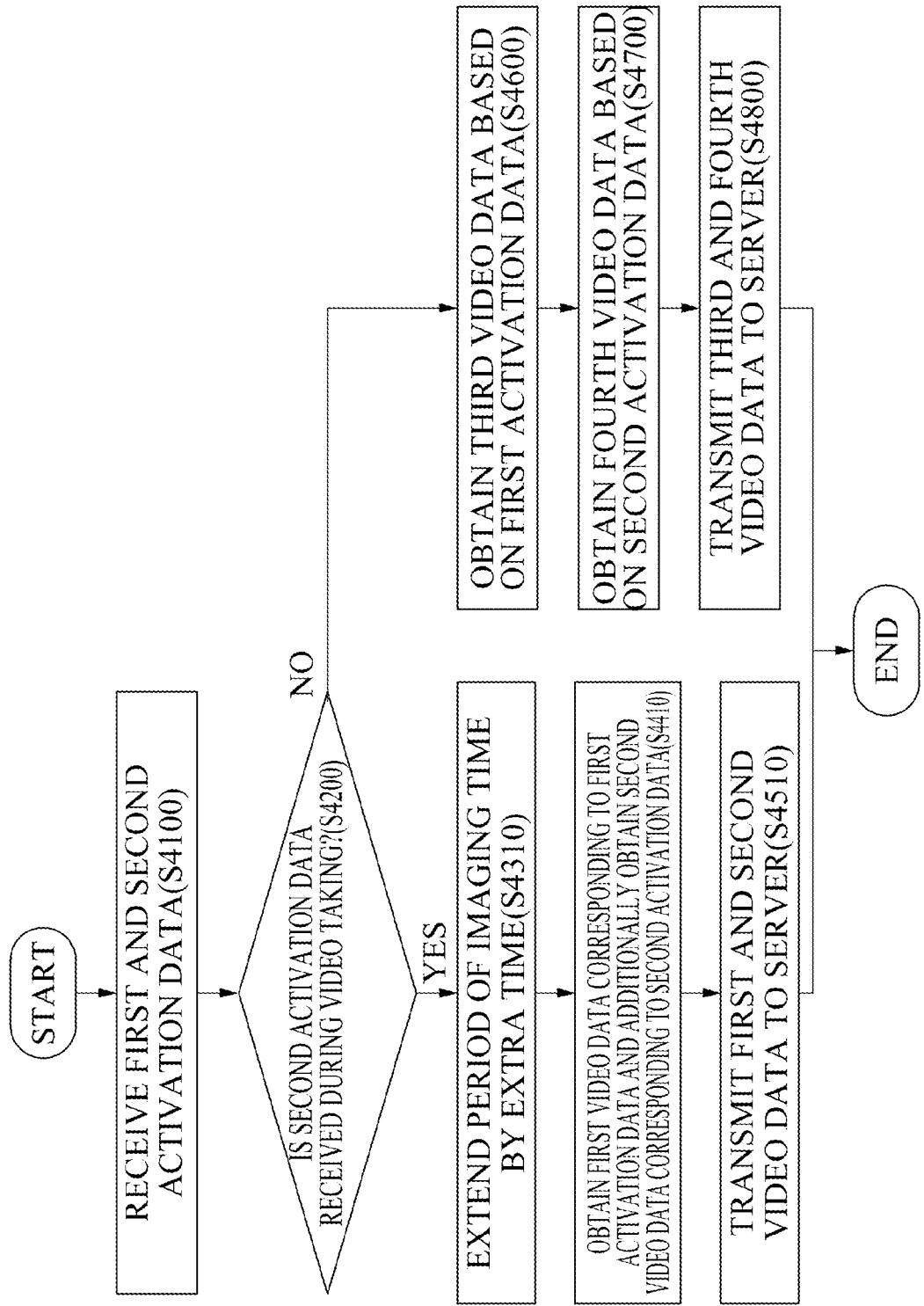

FIGS. 24 and 25 are diagrams illustrating operation processes performed by the wearable device 2000 when the user moves the object while shooting the video according to the embodiment of the present invention.

Referring to FIG. 24, the wearable device 2000 may perform a step S4100 of receiving first and second activation data, a step S4200 of determining whether the second activation data is received during video taking, a step S4300 of ignoring the second activation data, a step S4400 of obtaining first video data on the basis of the first activation data, a step S4500 of transmitting the first video data to the server 3000, a step S4600 of obtaining third video data on the basis of the first activation data, a step S4700 of obtaining fourth video data on the basis of the second activation data, and a step S4800 of transmitting the third and fourth video data to the server 3000.

Hereinafter, each operation will be described in detail.

The wearable device 2000 may receive the first and second activation data (S4100). For example, when the user moves the object to which the wireless communication device 1000 is attached at a first time point in the process of performing the medication adherence, the wireless communication device 1000 may perform the operations illustrated in FIG. 8 to transmit the first activation data, and when the user moves the object to which the wireless communication device 1000 is attached at a second time point after the first time point, the wireless communication device 1000 may similarly transmit the second activation data so that the wearable device 2000 may receive the first and second activation data.

The wearable device 2000 may determine whether the second activation data is received during the video taking (S4200). For example, the wearable device 2000 may activate the camera module 2100 on the basis of the first activation data and determine whether a time point at which the second activation data is received is in the middle of the video taking. In other words, the wearable device 2000 may determine whether the time point at which the second activation data is received is present between a time point at which the camera module 2100 is activated and a time point at which the camera module 2100 is deactivated.

The wearable device 2000 may ignore the second activation data (S4300). For example, when it is determined that the time point at which the second activation data is received is present between the time point at which the camera module 2100 is activated and the time point at which the camera module 2100 is deactivated, the wearable device 2000 may not perform any operation in response to the second activation data.

The wearable device 2000 may obtain the first video data on the basis of the first activation data (S4400). As described elsewhere in the present invention, the wearable device 2000 may obtain the first video data by shooting the video for a predetermined first imaging time on the basis of the first activation data. In this case, although the wearable device 2000 receives the first and second activation data, the wearable device 2000 may obtain only the first video data.

The wearable device 2000 may transmit the first video data to the server 3000 (S4500). As described elsewhere in the present invention, the wearable device 2000 may transmit the first video data to the server 3000 for data analysis after a predetermined period of waiting time has elapsed from the time point at which the first video data is obtained.

When it is determined that the time point at which the second activation data is received is not in the middle of the video taking, the wearable device 2000 may obtain the third video data on the basis of the first activation data (S4600) and obtain the fourth video data on the basis of the second activation data (S4700). In other words, the wearable device 2000 may obtain the third and fourth video data corresponding to the first and second activation data received at different time points.

The wearable device 2000 may transmit the third and fourth video data to the server 3000 (S4800). As described elsewhere in the present invention, the wearable device 2000 may transmit the third and fourth video data to the server 3000 for data analysis.

Meanwhile, the wearable device 2000 may discontinuously or continuously transmit the third video data and the fourth video data to the server 3000. As an example, before the fourth video data is obtained after the third video data is obtained, the wearable device 2000 may transmit the third video data to the server 3000. As another example, after a predetermined waiting time has elapsed after the fourth video data is obtained, the wearable device 2000 may continuously transmit the third and fourth video data to the server 3000. In this case, it is possible to prevent heat from being generated due to excessive data transmission from the wearable device 2000 to the server 3000 or data transmission during the video taking.

Referring to FIG. 25, the wearable device 2000 may perform a step S4100 of receiving first and second activation data, a step S4200 of determining whether the second activation data is received during video taking, a step S4310 of extending an imaging time by an extra time (or an additional period of time), a step S4410 of obtaining first video data corresponding to the first activation data and additionally obtaining second video data corresponding to the second activation data, a step S4510 of transmitting the first and second video data to the server 3000, a step S4600 of obtaining third video data on the basis of the first activation data, a step S4700 of obtaining fourth video data on the basis of the second activation data, and a step S4800 of transmitting the third and fourth video data to the server 3000.

Hereinafter, each operation will be described in detail. However, duplicate parts between step S4100, step S4200, step S4600, step S4700, and step S4800 and the operations described in FIG. 23 will be omitted.

When the second activation data is received during the video taking, the wearable device 2000 may extend the imaging time by an extra time (S4310). As an example, when the time point at which the second activation data is received is within the imaging time from the time point at which the camera module 2100 is activated by the first activation data, the wearable device 2000 may shoot the video for the extra time in addition to the imaging time. As another example, the wearable device 2000 may reset a timer for setting a time for taking a video, and take the video for a longer time than the existing imaging time.

The extra time may be set in various ways. As an example, the extra time may be set based on a signal that is received by the wearable device 2000 from the wireless communication device 1000. Specifically, the extra time may be set based on unique identification information of the wireless communication device 1000 obtained by the wearable device 2000 from the wireless communication device 1000. As another example, the extra time may be set based on the imaging time according to the first activation data. For example, the extra time may be set to be less than or equal to the imaging time. As still another example, when the video is additionally taken by resetting the timer as described above, the extra time may vary according to the time point at which the timer is reset.

The wearable device 2000 may obtain the first video data corresponding to the first activation data and additionally obtain the second video data corresponding to the second activation data (S4410). For example, when the wearable device 2000 receives the first activation data, the wearable device 2000 may obtain the first video data by taking the video for the imaging time, and obtain the second video data by taking the video for the extra time. Here, the first video data and the second video data may be understood as dividing the entire video data obtained by taking the video during the imaging time and the extra time into video data corresponding to the imaging time and video data corresponding to the extra time.

The wearable device 2000 may transmit the first and second video data to the server 3000 (S4510). For example, similar to the content described in FIG. 23, the wearable device 2000 may continuously or discontinuously transmit the first and second video data to the server 3000.

Figure 26:
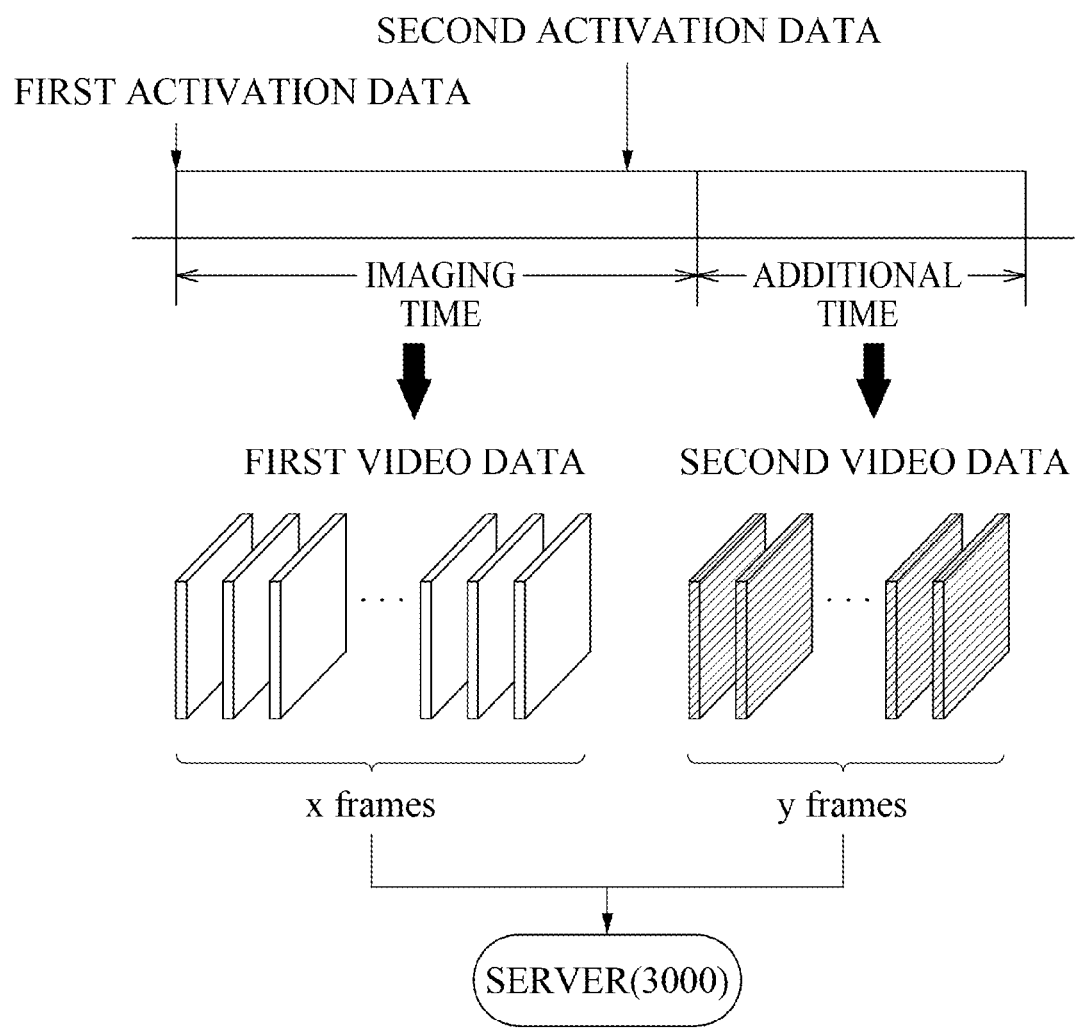
FIGS. 26 to 28 are diagrams illustrating a method of processing and analyzing video data in a server when a user moves an object while shooting a video according to an embodiment of the present invention.
Figure 27:
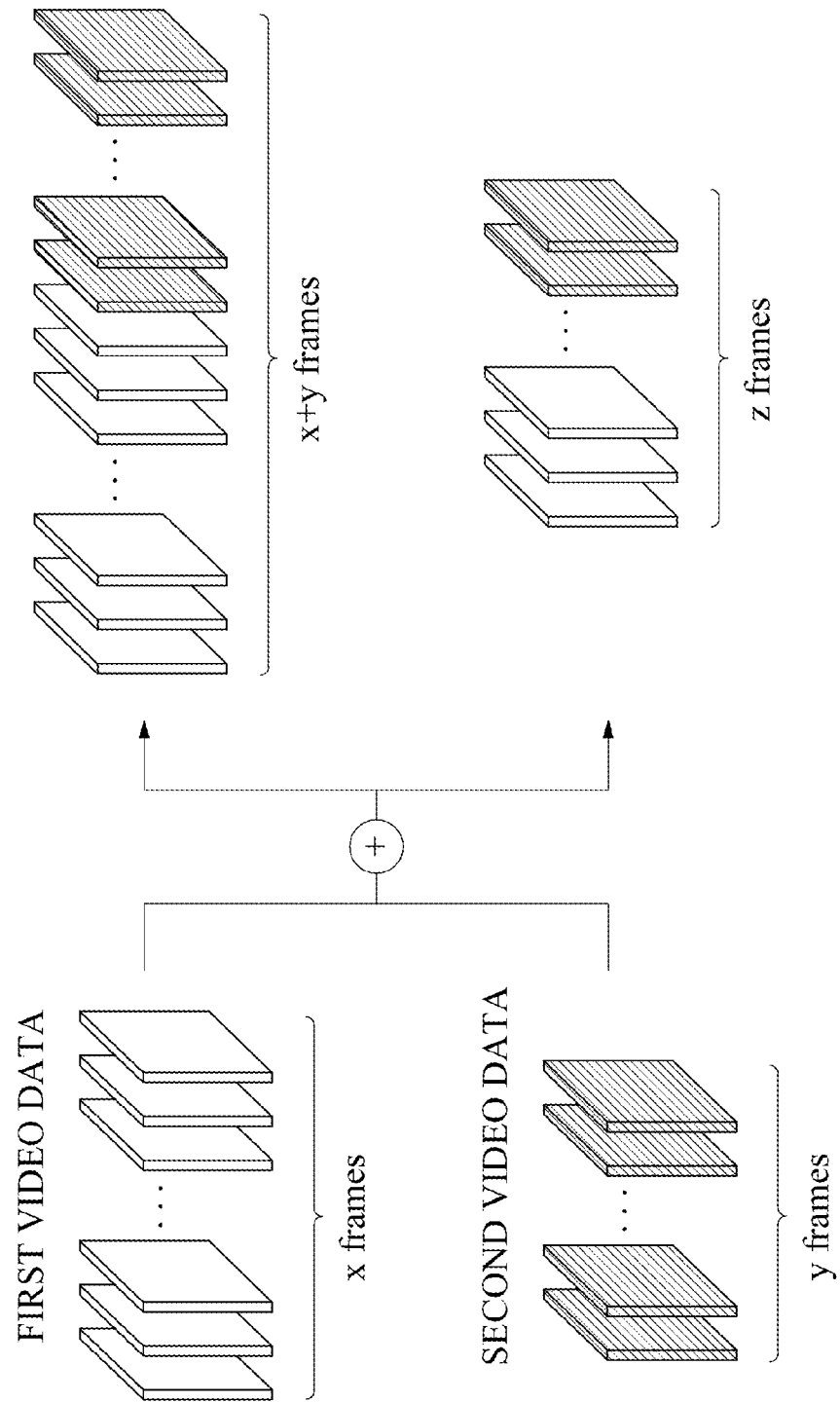
Figure 28:
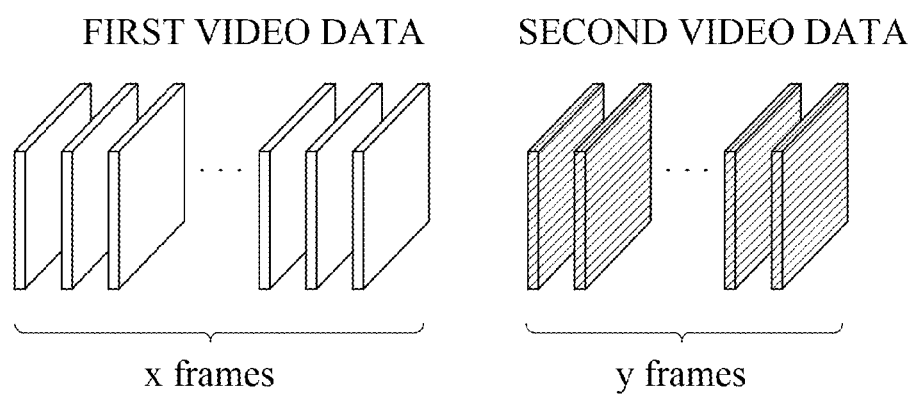

FIGS. 26 to 28 are diagrams illustrating a method of processing and analyzing video data in the server 3000 when the user moves the object while taking the video according to the embodiment of the present invention.

Referring to FIG. 26, the server 3000 may receive the first and second video data from the wearable device 2000. For example, ad described in FIG. 25, the wearable device 2000 may take the video for the imaging time and the extra time and, accordingly, may transmit the first video data corresponding to the imaging time and the second video data corresponding to the extra time to the server 3000.

Here, the first and second video data may be divided by the wearable device 2000 and transmitted to the server 3000 or may be transmitted as one piece of video data to be divided by the server 3000.

In addition, here, the number of frames of the first video data may be different from the number of frames of the second video data. For example, in the case in which the extra time is shorter than the period of imaging time, when the first video data has x frames, the second video data may have y frames less than that of the first video data.

Referring to FIG. 27, the server 3000 may merge the first video data and the second video data prior to data analysis.

For example, the server 3000 may connect the first video data and the second video data in series and merge. For example, the server 3000 may obtain merged video data by attaching the second video data to the first video data and may analyze the merged video data to determine whether the user performs medication adherence.

As another example, the server 3000 may combine and merge the first video data and the second video data. For example, the server 3000 may obtain merged video data by merging at least a part of the first video data and at least a part of the second video data and may analyze the merged video data to determine whether the user performs the medication adherence.

The server 3000 may process the merged video data to have a specific number of frames prior to data analysis for determining whether the user performs the medication adherence. For example, the server 3000 may adjust the number of frames of the video data obtained by merging the first video data and the second video data so as to correspond to the number of input nodes of an artificial neural network (e.g., the above-described detection model or confirmation model) used to determine whether the medication adherence is performed.

Referring to FIG. 28, the server 3000 may determine whether the medication adherence is performed for each piece of video data. For example, when the server 3000 receives the first and second video data from the wearable device 2000 as described in steps S4600 to S4800 in FIGS. 24 and 25, the server 3000 may determine whether the user performs the medication adherence without merging the first and second video data, and finally determine whether the user performs the medication adherence on the basis of a result of the determination.

In this case, the server 3000 may expect that the second video data whose shooting initiation time point is relatively later will further reflect the process of the medication adherence of the user, and thus the server 3000 may set the importance of the second video data to be higher than the importance of the first video data.

More specifically, as shown in table of FIG. 28, as a result of analyzing the first video data and the second video data, when it is confirmed that the user performs the medication adherence in both of the first video data and the second video data, the server 3000 may determine that the user has performed the medication adherence. Further, when it is confirmed that the user does not perform the medication adherence in the first video data but the user performs the medication adherence in the second video data, the server 3000 may finally determine that the user has performed the medication adherence. Further, when it is confirmed that the user performs the medication adherence in the first video data but the user does not perform the medication adherence in the second video data, the server 3000 may finally determine that the user has not performed the medication adherence. Further, when it is confirmed that the user does not perform the medication adherence in both of the first video data and the second video data, the server 3000 may finally determine that the user has not performed the medication adherence.

In the above, the second video data is expected to reflect the process of the medication adherence of the user more than the first video data so that the importance of the second video data is set to be higher than that of the first video data, but the technological concept of the present invention is not limited thereto, and the importance of the first video data may be set to be higher than that of the second video data.

In the above, when the number of types of medication that the user adheres to is one, the operation of the medication adherence monitoring system 100 has been described in the case in which the user moves the object containing the medication and thus the wireless communication device 1000 attached to the object transmits the activation data to the wearable device 2000 several times.

Hereinafter, when the user adheres to a plurality of medications, the operation of the medication adherence monitoring system 100 will be described in the case in which the activation data is transmitted to the wearable device 2000 by each of a plurality of wireless communication devices.

Figure 29:
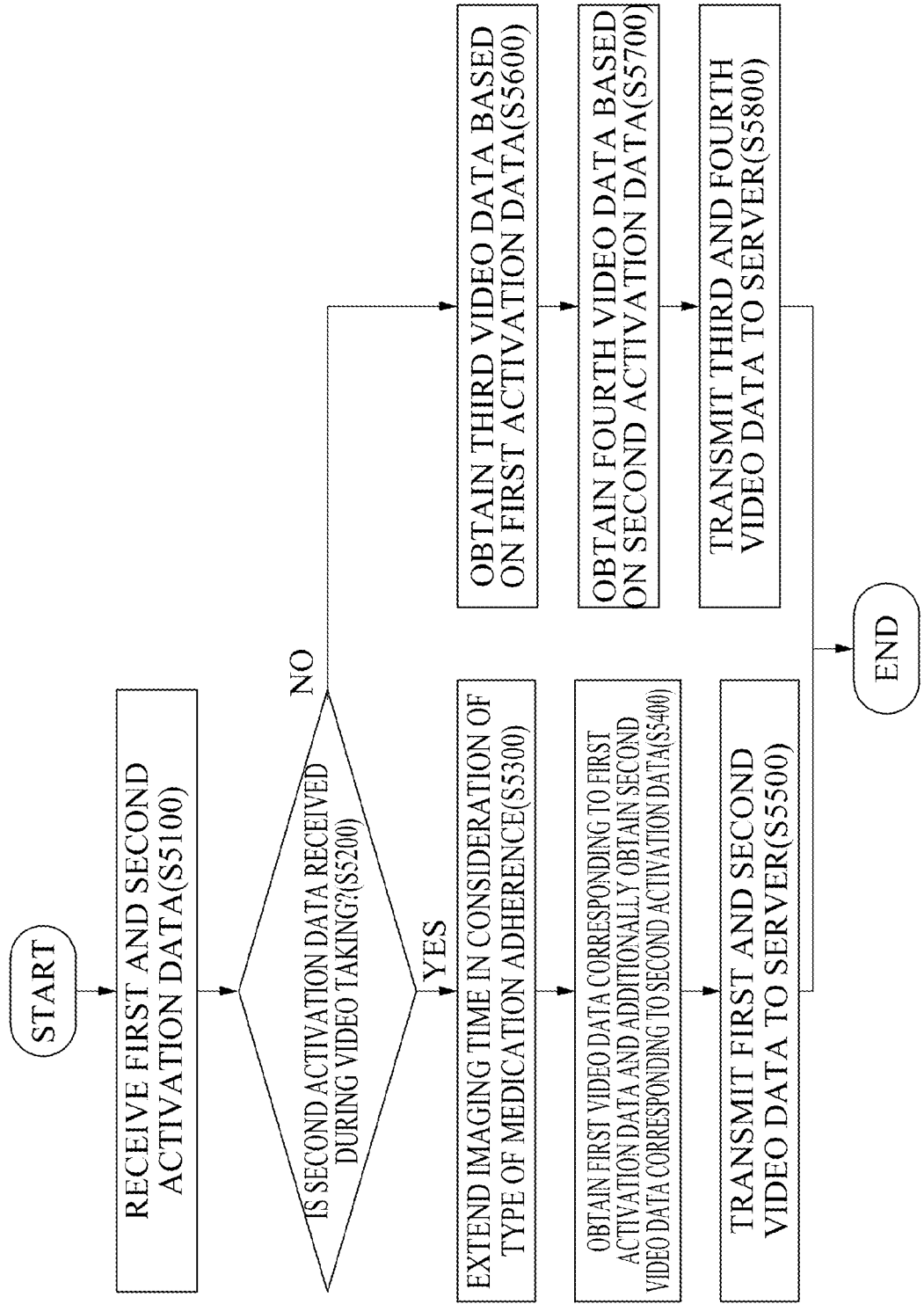
FIG. 29 is a diagram illustrating an operation process performed by a wearable device when a user moves an object while shooting a video in a case in which the user adheres to different medications according to an embodiment of the present invention.

FIG. 29 is a diagram illustrating an operation process performed by the wearable device 2000 when the user moves the object while shooting a video in a case in which the user performs adherence on different medications according to the embodiment of the present invention.

Referring to FIG. 29, the wearable device 2000 may perform a step S5100 of receiving first and second activation data, a step S5200 of determining whether the second activation data is received during video taking, a step S5300 of extending an imaging time in consideration of the type of medication adherence, a step S5400 of obtaining first video data corresponding to the first activation data and additionally obtaining second video data corresponding to the second activation data, a step S5500 of transmitting the first and second video data to the server 3000, a step S5600 of obtaining third video data on the basis of the first activation data, a step S5700 of obtaining fourth video data on the basis of the second activation data, and a step S5800 of transmitting the third and fourth video data to the server 3000.

Hereinafter, each operation will be described in detail.

The wearable device 2000 may receive the first and second activation data (S5100). For example, when the user adheres to a first medication and a second medication of different types, the wearable device 2000 may receive the first activation data and the second activation data from a first wireless communication device and a second wireless communication device corresponding to the first and second medications, respectively. In this case, each of the first activation data and the second activation data may include information about the type of each medication adherence.

The wearable device 2000 may determine whether the second activation data is received during the video shooting (S5200). For example, when the wearable device 2000 receives the first activation data and activates the camera module 2100 to receive the second activation data during the video shooting, the wearable device 2000 may determine that the second activation data is received during the video shooting.

Meanwhile, since the types of the medication that the user adheres to are different, the wearable device 2000 may receive the first activation data to shoot the video during a first imaging time corresponding to the adherence of the first medication, and may receive the second activation data to shoot the video during a second imaging time. In this case, the second imaging time may correspond to the adherence to the second medication. For example, the adherence to the first medication may refer to an action of taking the medication and the first imaging time may refer to a time corresponding to the taking of the medication, and the adherence to the second medication may refer to an action of administering an eye drop and the second imaging time may refer to a time corresponding to the administering of the eye drop.

Therefore, the wearable device 2000 may determine whether the second activation data is received within the first imaging time from the time point at which the camera module 2100 is activated, on the basis of the first activation data.

Here, the first imaging time and the second imaging time may be set based on information included in the signals that the wearable device 2000 receives from the first wireless communication device and the second wireless communication device, respectively.

The wearable device 2000 may extend the imaging time in consideration of the type of medication adherence (S5300). For example, when the wearable device 2000 receives the second activation data during the video shooting on the basis of the first activation data, the wearable device 2000 may further shoot the video for an extra time after the first imaging time has elapsed from the time point at which the camera module 2100 is activated.

Here, the extra time may be set based on the first imaging time and/or the second imaging time. For example, the extra time may be smaller than the second imaging time. Since the extra time is set to be smaller than the second imaging time, it is possible to prevent unnecessary videos from being shot.

The wearable device 2000 may obtain the first video data corresponding to the first activation data and additionally obtain the second video data corresponding to the second activation data (S5400).

Here, the first and second video data may be divided according to different criteria. As an example, the first video data may correspond to the first imaging time and the second video data may correspond to the extra time. As another example, the first video data may correspond to an interval between the time point at which the camera module 2100 is activated and the time point at which the second activation data is received, and the second video data may correspond to an interval between the time point at which the second activation data is received and the time point at which the camera module 2100 is deactivated, on the basis of the first activation data.

The wearable device 2000 may transmit the first and second video data to the server 3000 (S5500). For example, the wearable device 2000 may continuously or discontinuously transmit the first video data and the second video data to the server 3000. In addition, for example, the wearable device 2000 may divide and transmit the first video data and the second video data to the server 3000.

When it is determined that the second activation data is not received during the video shooting, the wearable device 2000 may obtain the third video data on the basis of the first activation data (S5600). Since the content of step S5600 is the same as the content of step S4600 described in FIGS. 24 and 25, a description thereof will be omitted.

The wearable device 2000 may obtain the fourth video data on the basis of the second activation data (S5700). Since the content of step S5700 is the same as the content of step S4700 described in FIGS. 24 and 25, a description thereof will be omitted.

The wearable device 2000 may transmit the third and fourth video data to the server 3000 (S5800). Since the content of step S5800 is the same as the content of step S4800 described in FIGS. 24 and 25, a description thereof will be omitted.

The server 3000 may use the video data received from the wearable device 2000 to determine whether the user performs the medication adherence multiple times. As an example, when the server 3000 receives the first video data and the second video data from the wearable device 2000, the server 3000 may use a first artificial neural network to determine whether the user performs first medication adherence from the first video data, and may use a second artificial neural network to determine whether the user performs second medication adherence from the second video data. As another example, the server 3000 may use the first and second video data received from the wearable device 2000 as one input data and use an artificial neural network to determine whether each of the first medication adherence and the second medication adherence is performed. The determination of whether to adhere to different medications will be described in detail below.

In the above, the case of monitoring whether the user performs the medication adherence has been mainly described, but the user may perform various actions for healthcare, such as health promotion or disease prevention, in addition to the medication adherence. In this case, when the medication adherence monitoring system 100 is used, it is possible to monitor and manage the user's health management actions, similar to the medication adherence.

Hereinafter, a health management system for monitoring the user's health management actions using the medication adherence monitoring system 100 will be described with reference to FIGS. 30 and 31. The health management system may have the same configuration as the medication adherence monitoring system 100, but some components may be operated differently in detecting the user's actions.

Figure 30:
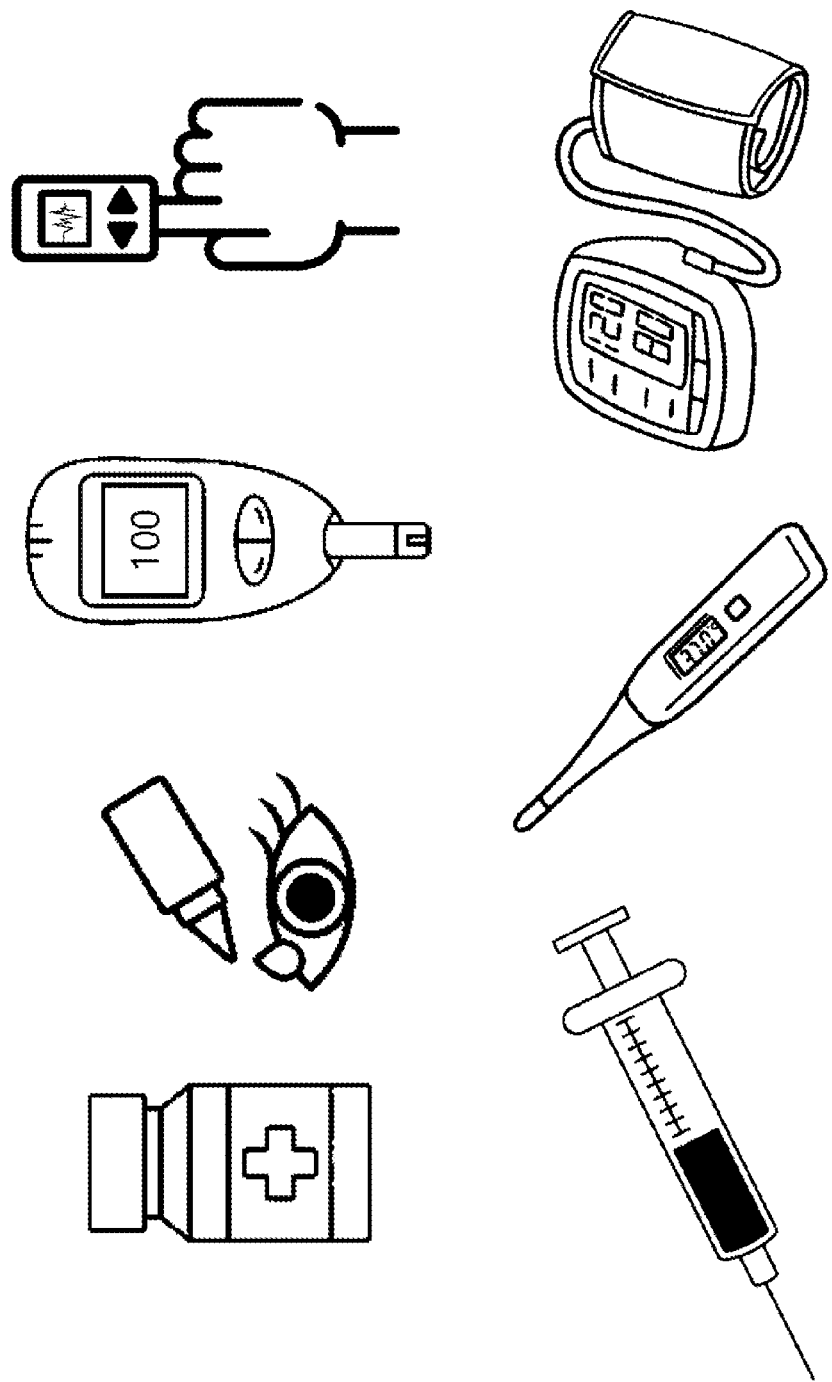
FIG. 30 is a diagram illustrating user's health management actions according to an embodiment of the present invention.

FIG. 30 is a diagram illustrating user's health management actions according to an embodiment of the present invention.

Referring to FIG. 30, the user's health management actions may include actions for health monitoring, promotion, or assistance, or disease prevention, such as medication adherence, blood glucose measurement, electrocardiogram measurement, blood pressure measurement, and/or temperature measurement. Furthermore, the health management actions may include using exercise equipment, taking health supplements, managing a diet, or undergoing food therapy.

The health management system may have the same configuration as the medication adherence monitoring system 100. For example, the health management system may include a wireless communication device 1000, a wearable device 2000, a server 3000, and a terminal device 4000. Here, like the medication adherence monitoring system 100, the wireless communication device 1000 may detect the initiation of the user's health management actions to provide activation data to the wearable device 2000, the wearable device 2000 may shoot a video on the basis of the activation data to obtain video data related to the user's health management actions, and the server 3000 may analyze the video data obtained from the wearable device 2000 to determine whether the user performs the health management actions.

However, the configuration of the health management system may be implemented differently from the medication adherence monitoring system 100 or the health management system may perform a function different from that of the medication adherence monitoring system 100 according to the health management actions.

For example, when the health management action is measuring blood pressure, the wireless communication device 1000 may be attached to a blood pressure monitor to detect the user's use of the blood pressure monitor. Specifically, the wireless communication device 1000 may be attached to a cuff of the blood pressure monitor to detect the user's use of the blood pressure monitor and provide activation data to the wearable device 2000.

As another example, when the health management action is managing a diet or undergoing food therapy, the wireless communication device 1000 may be attached to a container containing food to check whether the user consumes food. Specifically, the wireless communication device 1000 may be attached to an inner side of a lid of a food container to detect that the lid of the food container is opened by using a motion sensor and/or an ambient light sensor and provide activation data to the wearable device 2000. Alternatively, the wireless communication device 1000 may be configured as a part of the food container and may detect that the lid of the food container is opened and provide the activation data to the wearable device 2000.

Meanwhile, the health management system may be operated similarly to the medication adherence monitoring system 100 but some components thereof may be operated differently. For example, in the health management system, the wearable device 2000 may set an imaging time on the basis of signals received from the wireless communication device 1000.

Hereinafter, the operation of the wearable device 2000 in the health management system will be described with reference to FIG. 31.

Figure 31:
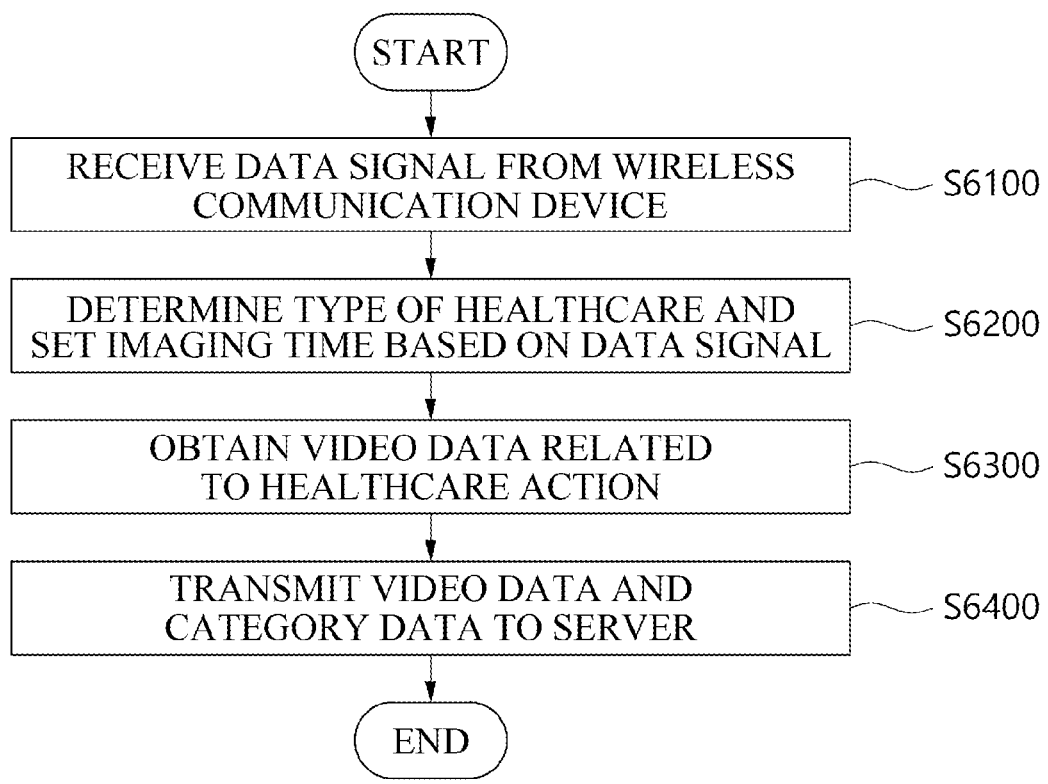
FIG. 31 is a diagram illustrating an operation process of a wearable device in a health management system according to an embodiment of the present invention.

FIG. 31 is a diagram illustrating an operation process of a wearable device 2000 in a health management system according to an embodiment of the present invention.

Referring to FIG. 31, the health management system may perform a step S6100 of receiving, by the wearable device 2000, a data signal from the wireless communication device 1000, a step S6200 of determining a health management type and setting an imaging time on the basis of the data signal, a step S6300 of obtaining video data related to a health management action, and a step S6400 of determining whether the health management action is performed by using the video data.

Hereinafter, each operation will be described in detail.

The wearable device 2000 may receive the data signal from the wireless communication device 1000 (S6100). Here, the data signal may refer to a data packet including the above-described specific data and may include identification data, manufacturer data, transmission strength data, motion data, ambient light data, and/or activation data of the wireless communication device 1000. Furthermore, the data signal may further include data indicating the type of the user's health management action.

The wearable device 2000 may determine the health management type and set an imaging time on the basis of the data signal (S6200). As an example, the second control unit 2500 may determine the type of the health management action performed by the user on the basis of the identification data included in the data signal. Specifically, the second control unit 2500 may compare reference data for the health management action, which is pre-stored in the second memory 2300 or received from the server 3000, with the identification data to determine the type of the health management action performed by the user. As another example, the second control unit 2500 may determine the type of health management action performed by the user on the basis of the data indicating the type of health management action included in the data signal. Specifically, the second control unit 2500 may compare the reference data for the health management action, which is pre-stored in the second memory 2300 or received from the server 3000, with the data indicating the type of health management action to determine the type of health management action performed by the user. Here, the wearable device 2000 may store a result of determining the type of health management action as category data.

The wearable device 2000 may set the imaging time according to the determined type of health management action. The wearable device 2000 may shoot a video for a different imaging time according to the type of health management action performed by the user by setting the imaging time in consideration of the data indicating the identification data or the type of health management action. For example, when the data indicating the identification data or the type of health management action indicates the user's use of the blood pressure monitor, the imaging time may be set sufficiently long as a period of time required to use the blood pressure monitor.

The wearable device 2000 may obtain the video data related to the health management action (S6300). For example, the second control unit 2500 may obtain the video data by shooting the video for the set imaging time in consideration of the data indicating the identification data or the type of health management action.

The wearable device 2000 may transmit the video data and the category data to the server 3000 (S6400). For example, the second control unit 2500 may transmit the video data and the category data to the server 3000 by using the second communication unit 2400. Here, the category data may refer to data for identifying the type of the user's health management action as described above. However, the wearable device 2000 may transmit the unique identification data of the wireless communication device 1000 received from the wireless communication device 1000 without transmitting the category data to the server 3000.

In the above, the method of determining whether the user performs the medication adherence by using the medication adherence monitoring system 100 has been described.

Hereinafter, structures and a design method of the wireless communication device 1000 and the wearable device 2000 which constitute the medication adherence monitoring system 100 will be described with reference to FIGS. 32 to 35.

Figure 32:
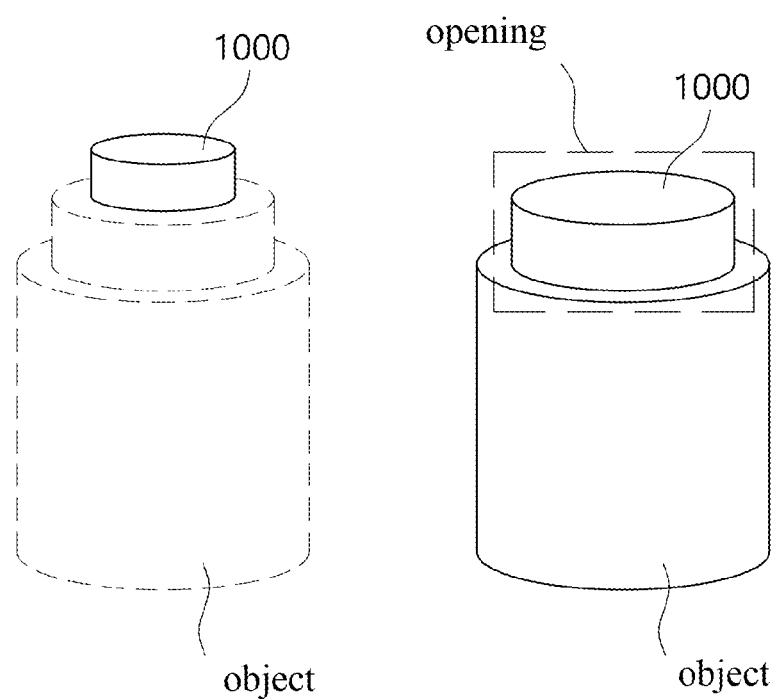
FIG. 32 is a diagram illustrating an object and a wireless communication device attached to the object according to an embodiment of the present invention.

FIG. 32 is a diagram illustrating an object and a wireless communication device 1000 attached to the object according to an embodiment of the present invention.

Referring to FIG. 32, the wireless communication device 1000 may be attached to or detached from an object for accommodating a medication. For example, at least a portion of the wireless communication device 1000 may include an attachment region, and the wireless communication device 1000 may be attached to the object through the attachment region or may be detached from the object due to an external force. As another example, the wireless communication device 1000 may be attached to or detached from the object through a separate attachment member.

The wireless communication device 1000 may be implemented in various shapes. For example, the wireless communication device 1000 may be implemented to have a shape such as a hemispherical shape, a cylindrical shape, a polygonal column shape, a truncated conical shape, a truncated polygonal pyramid shape, or the like.

Meanwhile, the wireless communication device 1000 may be implemented as a portion of the object. For example, referring to FIG. 32 again, the wireless communication device 1000 may be implemented as an opening (e.g., a cap or lid portion) of the object.

Figure 33:
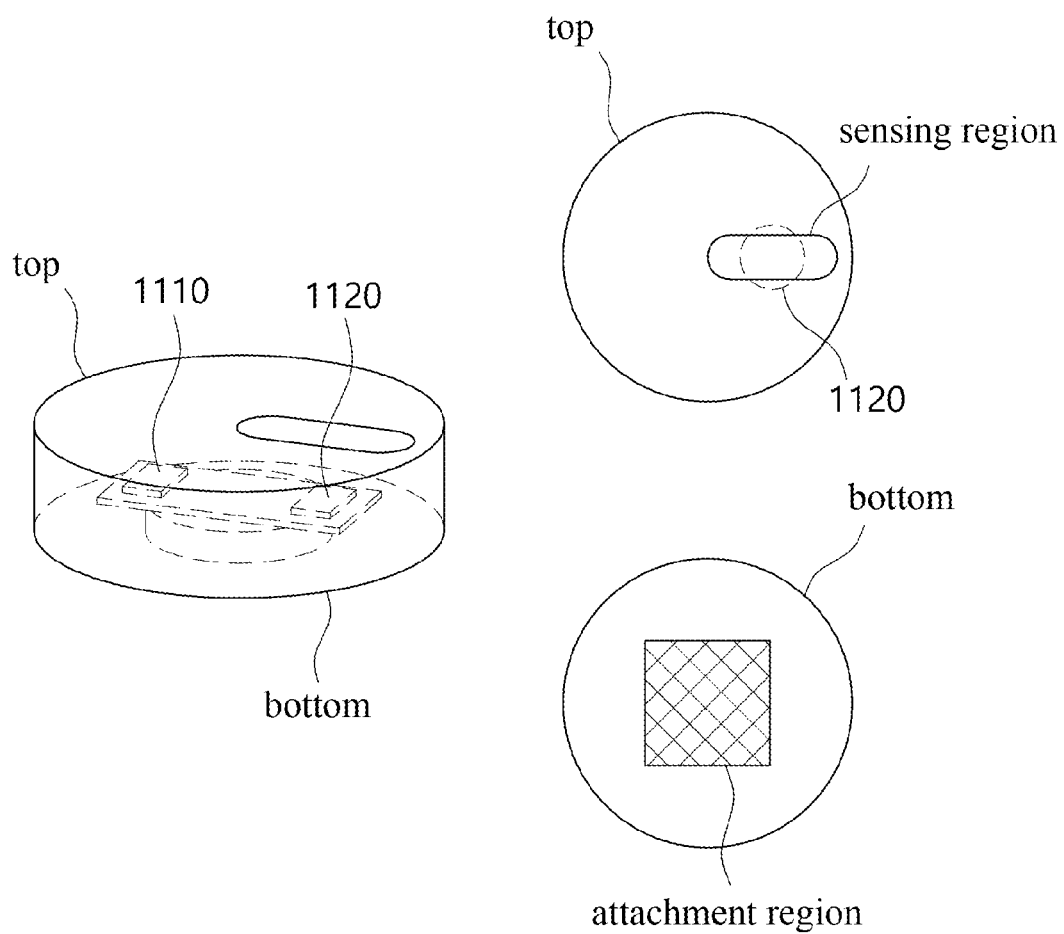
FIG. 33 is a diagram illustrating a structure of a wireless communication device according to an embodiment of the present invention.

FIG. 33 is a diagram illustrating a structure of a wireless communication device 1000 according to an embodiment of the present invention.

Referring to FIG. 33, the wireless communication device 1000 may be implemented as a figure having a top including a sensing region and a bottom including an attachment region.

The top may refer to a surface that is not attached to an object. For example, since an attachment region is not formed on the top of the wireless communication device 1000, the wireless communication device 1000 may not be attached to the object through the top.

The bottom may refer to a surface that is attached to the object. For example, since the attachment region is formed on the bottom of the wireless communication device 1000, the wireless communication device 1000 may be attached to the object through the bottom.

The sensing region may be understood as a region in which at least some sensors of a sensor unit 1100 of the wireless communication device 1000 detect an environment around the wireless communication device 1000. For example, an ambient light sensor 1120 may detect brightness around the wireless communication device 1000 through the sensing region.

As described above, in the wireless communication device 1000, the sensing region and the attachment region are formed on different surfaces so that the sensing region and the attachment region may not overlap. Accordingly, even when the wireless communication device 1000 is attached to the object, the wireless communication device 1000 does not interfere with the sensor unit 1100 from detecting the environment around the wireless communication device 1000.

Meanwhile, the sensing region is not necessarily formed on the top of the wireless communication device 1000 and may be formed on another surface (e.g., a side surface or a bottom) of the wireless communication device 1000. However, the sensing region may be formed on a surface different from the attachment region or may be formed so as not to overlap the attachment region as collecting the ambient light around the wireless communication device through the sensing region would not be disturbed by the attachment region.

The wireless communication device 1000 may include a housing which defines an inner space, and the components of the wireless communication device 1000 may be disposed in the inner space of the housing. For example, in the inner space of the housing, a plate for supporting a sensor unit 1100, a first memory 1200, a first communication unit 1300, and a first control unit 1400 (hereinafter, referred to as a "sensor unit" etc.) and a battery for supplying power may be disposed.

Here, the battery, the plate, the sensor unit, and the like may be sequentially disposed in the inner space of the housing. For example, referring to FIG. 33, the battery may be disposed on the bottom including the attachment region, the plate may be disposed on the battery, the sensor unit and the like may be disposed on the plate, and the top including the sensing region may be located above the sensor unit and the like. In this case, the sensor unit and the like may be disposed at different positions on the plate, and the sensor unit 1100 and the sensing region may be located to correspond to each other. Specifically, a motion sensor 1110 and the ambient light sensor 1120 may be disposed on the plate to be spaced a preset distance from each other, and the ambient light sensor 1120 may be disposed within a region spaced a preset distance from a central axis of the sensing region of the top, on the plate.

Figure 34:
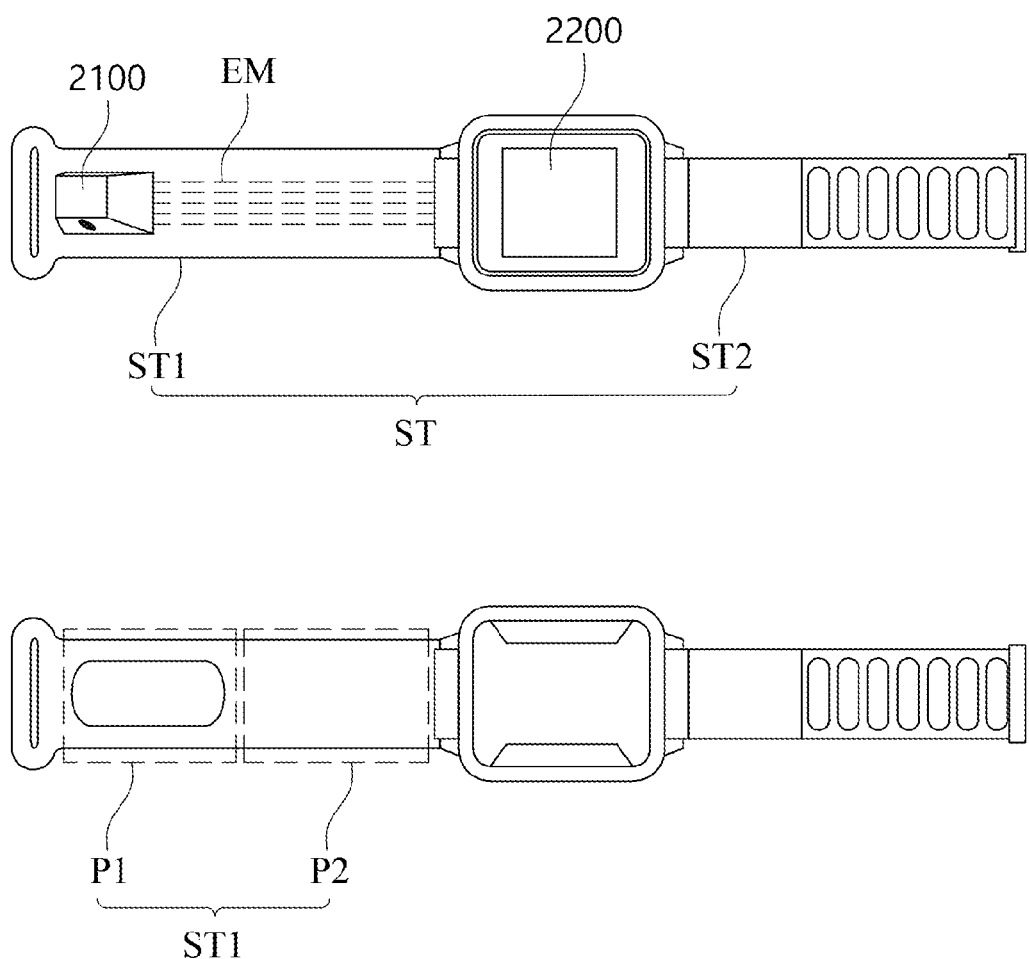
FIG. 34 is a diagram illustrating a configuration and structure of a wearable device of an embodiment of the present invention.

FIG. 34 is a diagram illustrating a configuration and structure of a wearable device 2000 according to an embodiment of the present invention.

FIG. 35 is a diagram illustrating a field of view FoV of a camera module 2100 according to a slope of the camera module 2100 according to an embodiment of the present invention.

Referring to FIG. 34, the wearable device 2000 may be implemented in the form of being worn on a user's wrist. For example, the wearable device 2000 may be implemented in the form of a band or watch worn on the wrist. Hereinafter, the wearable device 2000 is mainly described as being worn on the user's wrist, but the technological concept of the present invention is not limited thereto. Even when the wearable device 2000 is worn on at least a portion of the user's body rather than the wrist, the configuration and structure of the wearable device 2000 may be similarly applied.

Meanwhile, in the wearable device 2000, a position at which the camera module 2100 is disposed should be mainly determined when considering the operation of the medication adherence monitoring system 100. For example, when the wearable device 2000 is worn on the user's wrist, the wearable device 2000 needs to capture an image of the user's palm. However, a back or side surface of the user's hand may be photographed according to the arrangement position of the camera module 2100 on the wearable device 2000, and thus it may be difficult to obtain image data required for analysis.

Hereinafter, the configuration of the wearable device 2000 and the arrangement position of the camera module 2100 will be described and, furthermore, a mechanical design method of the wearable device 2000 in consideration of the arrangement of the camera module 2100 will be described.

The wearable device 2000 may include a component of which a size or a length is adjustable by the user. For example, the wearable device 2000 may include a first strap ST1 including a first end coupled to a first side of the main body 2200 and a second end including a first connection portion, and a second strap ST2 including a third end coupled to a second side of the main body 2200 and a second connection portion. Here, the first connection portion and the second connection portion are connected to each other to allow sizes thereof to be adjusted. Specifically, the wearable device 2000 may include the first strap ST1 including a hook, a buckle, and/or a loop, and the second strap ST2 of which a length is adjustable by passing through the buckle of the first strap ST1 or being caught by the hook while passing through the buckle. The second strap ST2 may further include a fixing portion where at least part of the second connection portion passing the first connection portion of the first strap ST1 is attachable. As another example, the wearable device 2000 may include a hook and one strap ST of which a size is adjustable. The first strap ST1 and the second strap ST2 are configured to have correlation described above, so that the second strap ST2 does not cover the camera module disposed on the first strap ST2 as mentioned below. Hereinafter, the wearable device 2000 is mainly described as including the first strap ST1 and the second strap ST2, but the technological concept of the present invention is not limited thereto.

The main body 2200 mentioned above may have an inner space surrounded by at least a top side, a bottom side, a first side, a second side, a third side and a fourth side. The first side the first side and the second side facing each other, the third side and the fourth side facing each other. Furthermore, the main body may have a length defined by the first side and the second side, and a width defined by the third side and the fourth side.

The wearable device 2000 further comprise a display unit exposed through the top side, a controller disposed in the inner space and configured to control the display unit output the information, and an electric connection line electrically connecting the controller and the camera module.

The camera module 2100 may be disposed on the wearable device 2000 to be spaced a preset distance from main body 2200. For example, when the wearable device 2000 is worn on the user's wrist, the camera module 2100 may be disposed to be spaced a preset distance from the main body 2200 so as to face the main body 2200. Here, the preset distance may be determined in consideration of an average wrist circumference of persons.

The first strap ST1 and the second strap ST2 may be designed in consideration of the camera module 2100. For example, when the camera module 2100 is disposed on the first strap ST1, the first strap ST1 may include the buckle, and the second strap ST2 may be designed to be adjustable in length by passing through the hook of the first strap ST1. In other words, the first strap ST1 on which the camera module 2100 is disposed includes the buckle, and the second strap ST2 on which the camera module 2100 is not disposed may pass through the buckle of the first strap ST1 so that the size of the wearable device 2000 may be adjusted.

In this case, the length of the first strap ST1 may be greater than the length of the second strap ST2. For example, in the wearable device 2000, in order for the camera module 2100 to be spaced the preset distance from the main body 2200, the first strap ST1 may have a length corresponding to the preset distance and the second strap ST2 may have a length relatively smaller than the length of the first strap ST1.

Further, when the wearable device 2000 is worn on the user's wrist, the first strap ST1 is disposed further outward than the second strap ST2 relative to the user's wrist, and thus it is possible to prevent the camera module 2100 from being pressed or covered by the second strap ST2.

By the way, the camera module wherein the camera module may be installed inside the strap ST while a lens of the camera module is positioned between a top surface and a bottom surface of the strap ST.

Referring to FIG. 34 again, the wearable device 2000 may include the main body 2200, and the first strap ST1 and the second strap ST2 which are connected to both ends of the main body 2200, and when the camera module 2100 is disposed on the first strap ST1, the camera module 2100 may be disposed on a portion of the first strap ST1 that is far apart from the main body 2200. For example, when the first strap ST1 includes a second portion P2 adjacent to the main body 2200 and a first portion P1 spaced apart from the main body 2200 based on a center thereof, the camera module 2100 may be located on the first portion P1. Through such arrangement of the camera module 2100, the user's palm may come into the field of view of the camera module 2100 as much as possible when the wearable device 2000 is worn on the user's wrist. In other words, the field of view of the camera module might head toward a direction along the width of the main body.

Meanwhile, when the wearable device 2000 includes one strap ST, the strap ST may include an adhesive portion for size adjustment. For example, the wearable device 2000 may include the main body 2200, and a connection member formed at one end of the main body 2200 and an adjusting member formed at the other end thereof. In this case, one end of the strap ST may be fixed to the connection member, and the other end of the strap ST is folded after passing through the adjusting member and adhered to the adhesive portion, where the adjusting member can be attachable or detachable, of the strap ST, and thus the size of the wearable device 2000 may be adjusted. In this case, the camera module 2100 may be disposed on a portion of the strap ST that is not the adhesive portion. Furthermore, the camera module 2100 may be disposed closer to a middle of the one end and the other end of the strap ST than the one end of the strap ST.

The camera module 2100 may be disposed on one surface of the strap ST. For example, the camera module 2100 may be disposed on a surface of the strap ST that is opposite to a surface surrounding the user's wrist when the wearable device 2000 is worn on the user's wrist. As another example, the camera module 2100 may be disposed on a side surface of the strap ST.

The camera module 2100 may be disposed to be inclined at a predetermined angle with respect to the strap ST. For example, referring to FIG. 35, a central axis ca of the camera module 2100 may have an angle in a range of 0 to 180° with respect to the strap ST.

Here, the field of view FoV of the camera module 2100 may be set according to a degree of inclination of the camera module 2100. For example, as the angle between the central axis ca of the camera module 2100 and the strap ST goes from 180° to 0°, the user's palm occupies a relatively large portion of the field of view FoV and, accordingly, an object other than the palm may not be photographed. Conversely, as the angle between the central axis ca of the camera module 2100 and the strap ST goes from 0° to 180°, the object other than the palm may come into the field of view FoV. In other words, as the angle between the central axis ca and the strap ST increases, the camera module 2100 has a relatively wide field of view FoV, but an object (e.g., other person) less related to medication adherence may come into the field of view FoV, which may cause problems such as privacy invasion and the like. As the angle between the central axis ca and the strap ST decreases, the camera module 2100 has a relatively narrow field of view FoV, but the object less related to the medication adherence may not come into the field of view FoV. Therefore, the degree of inclination of the camera module 2100 may be selected in an appropriate range so that the object less related to the medication adherence do not come into the field of view FoV while ensuring a sufficient field of view FoV. For example, the angle between the central axis ca of the camera module 2100 and the strap ST may be set in a range of 60° to 150°. More preferably, the angle between the central axis ca of the camera module 2100 and the strap ST may be set in a range of 90° to 120°.

In other words, the field of view FoV of the camera module 2100 may be set according to an optical axis of a lens of the camera module 2100. For example, the field of view FoV may be spread around the optical axis, and the palm may come into the field of view FoV as an angle between the optical axis and the strap ST increases. The angle between the optical axis and the strap ST could be acute. For example, the angle between the optical axis and the strap ST could be between 15 to 75°, preferably between 30° to 60°. Here, the angle might be determined as an angle between the optical axis and a surface of the strap ST where the camera module 2100 is disposed.

The camera module 2100 may be electrically connected to the second control unit 2500 of the wearable device 2000. For example, referring to FIG. 34 again, the second control unit 2500 and the camera module 2100 may be electrically connected to each other through electrical connecting members EM embedded in the strap ST on which the camera module 2100 is disposed. Specifically, when the wearable device 2000 includes the first strap ST1 and the second strap ST2 and the camera module 2100 is disposed on the first strap ST1, a portion of the first strap ST1 that is located between the second control unit 2500 and the camera module 2100 may have flexible electrical connecting members EM embedded therein. Here, the electrical connecting members EM may include a power supply line for supplying power to the camera module 2100, a data line for receiving image data from the camera module 2100, and a control line for controlling the camera module 2100.

Meanwhile, the camera module 2100 may not be electrically connected to the second control unit 2500 of the wearable device 2000 and may include a separate communication module to perform data communication with the second control unit 2500 of the wearable device 2000 or the server 3000.

Hereinafter, a method of confirming and inducing the user's wearing of the wearable device 2000 in the medication adherence monitoring system 100 according to an embodiment of the present invention will be described.

In the medication adherence monitoring system 100, the wearable device 2000 plays a major role in shooting a video or an image related to the medication adherence of the user. Therefore, in the medication adherence monitoring system 100, when the user performs the medication adherence, it is necessary for the user to wear the wearable device 2000 and it is necessary to prevent the user from performing the medication adherence without wearing the wearable device 2000.

In the medication adherence monitoring system 100, the wearable device 2000 may determine whether the user wears the wearable device 2000 by using a built-in sensor.

For example, the wearable device 2000 may determine whether the user wears the wearable device 2000 by using the number of steps of the user measured by using a built-in acceleration sensor and/or gravity sensor. Specifically, when the number of steps of the user measured by using the built-in sensors during a specific time interval is less than or equal to an average number of steps of a general person corresponding to the specific time interval or the minimum number of steps of the general person corresponding to the specific time interval, the wearable device 2000 may determine that the user does not wear the wearable device 2000. More specifically, when the number of steps of the user measured by using the built-in sensors for the past 24 hours based on a time point at which whether the user wears the wearable device 2000 is determined is less than or equal to a reference number of steps selected from a range of 3,000 to 6,000 steps, the wearable device 2000 may determine that the user does not wear the wearable device 2000. Alternatively, the wearable device 2000 may record the number of steps of the user in a preset period and specify a time interval in which the recorded number of steps is less than or equal to a preset number of steps or the number of steps is zero as a time interval in which the user does not wear the wearable device 2000.

As another example, the wearable device 2000 may determine whether the user wears the wearable device 2000 in consideration of the user's bio-signal measured by using a built-in bio-sensor. For example, the wearable device 2000 may determine whether the user wears the wearable device 2000 at the time point at which whether the user wears the wearable device 2000 is determined by using a heart rate sensor, a temperature sensor, and/or a biosensor that measures blood pressure, an electrocardiogram, blood oxygen saturation, etc.

Meanwhile, the medication adherence monitoring system 100 may determine whether the user wears the wearable device 2000 by using all of the above-described methods.

The medication adherence monitoring system 100 may temporarily or periodically determine whether the user wears the wearable device 2000. For example, the wearable device 2000 may determine whether the user wears the wearable device 2000 at each scheduled time point of the medication adherence of the user, once every 24 hours, at a time point at which the user initiates the medication adherence, or in a preset period. Specifically, the wearable device 2000 may determine whether the user wears the wearable device 2000 on the basis of information about the scheduled time point of the medication adherence of the user which is pre-stored therein or obtained from the server 3000. Alternatively, the wearable device 2000 may determine whether the user wears the wearable device 2000 at a time point of pairing or connecting with the wireless communication device 1000 or at a time point of receiving activation data from the wireless communication device 1000. In this case, the time point at which the wearable device 2000 is paired or connected with the wireless communication device 1000 or the time point at which the wearable device 2000 receives the activation data from the wireless communication device 1000 may be understood as a time point at which the user initiates the medication adherence or performs the medication adherence.

The medication adherence monitoring system 100 may provide a notification to a user or the like when it is determined that the user does not wear the wearable device 2000. For example, when it is determined that the user does not wear the wearable device 2000 when performing the medication adherence, the wearable device 2000 or the terminal device 4000 may output a non-wear notification, and when it is determined that the user does not wear the wearable device 2000 for a predetermined time, the wearable device 2000 or the terminal device 4000 may provide a notification to induce wearing the wearable device 2000 to the user. In this case, the terminal device 4000 may obtain information on whether the user wears the wearable device 2000 through the wearable device 2000 or the server 3000.

Meanwhile, a method of wearing the wearable device 2000 may be different for each person and a field of view of the camera module 2100 of the wearable device 2000 may vary according to the wearing method. For example, in the case in which the wearable device 2000 is worn on the wrist, when the wearable device 2000 is normally worn, the shooting direction of the camera module 2100 may be directed toward the outside of the user's body or toward the palm, and when the wearable device 2000 is incorrectly worn, the shooting direction of the camera module 2100 may be directed toward the user's body center or toward the arm, and thus a desired video may not be obtained.

The medication adherence monitoring system 100 may detect whether the wearable device 2000 is incorrectly worn and provide a notification to the user.

For example, the wearable device 2000 may determine whether the wearable device 2000 is incorrectly worn on the basis of a sensed value obtained by using the built-in sensor. Specifically, the wearable device 2000 may include a gravity sensor and determine whether the wearable device 2000 is incorrectly worn using the information about shooting direction of the camera module 2100 and the gravity direction obtained by using the gravity sensor.

As another example, the wearable device 2000 may determine whether the wearable device 2000 is incorrectly worn using video data obtained through the camera module 2100. For example, when the user wears the wearable device 2000 or when the wearable device 2000 receives a signal from the wireless communication device 1000, the wearable device 2000 may obtain a video or an image by using the camera module 2100 and may determine whether the wearable device 2000 is incorrectly worn by analyzing the obtained video or image.

When the wearable device 2000 is incorrectly worn, the medication adherence monitoring system 100 may provide a notification indicating to the user that the wearable device 2000 is incorrectly worn or a notification instructing the user to wear the wearable device 2000 again.

Hereinafter, a case in which the medication adherence monitoring system 100 is used as a digital therapeutic will be described with reference to FIG. 36.

Digital therapeutics may be understood as software programs that prevent, manage, or treat diseases. The digital therapeutics may be classified into complementary digital therapeutics that have indirect treatment effects and are used in conjunction with existing medicines, such as enhancing treatment effects of existing medicines through medication management, etc. and alternative digital therapeutics that have direct and independent treatment effects and directly control a user's action, such as drug addiction treatment applications or cognitive behavioral treatment applications. The medication adherence monitoring system 100 may serve as a complementary digital therapeutic in that it is used with an existing therapeutic agent and improves the effect of the existing therapeutic agent, as will be described below. Furthermore, the medication adherence monitoring system 100 may serve as an alternative digital therapeutic in that it induces health improvement of the user by controlling the user's action.

The medication adherence monitoring system 100 may monitor the presence or absence of side effects due to the medication adherence of the user.

Figure 36:
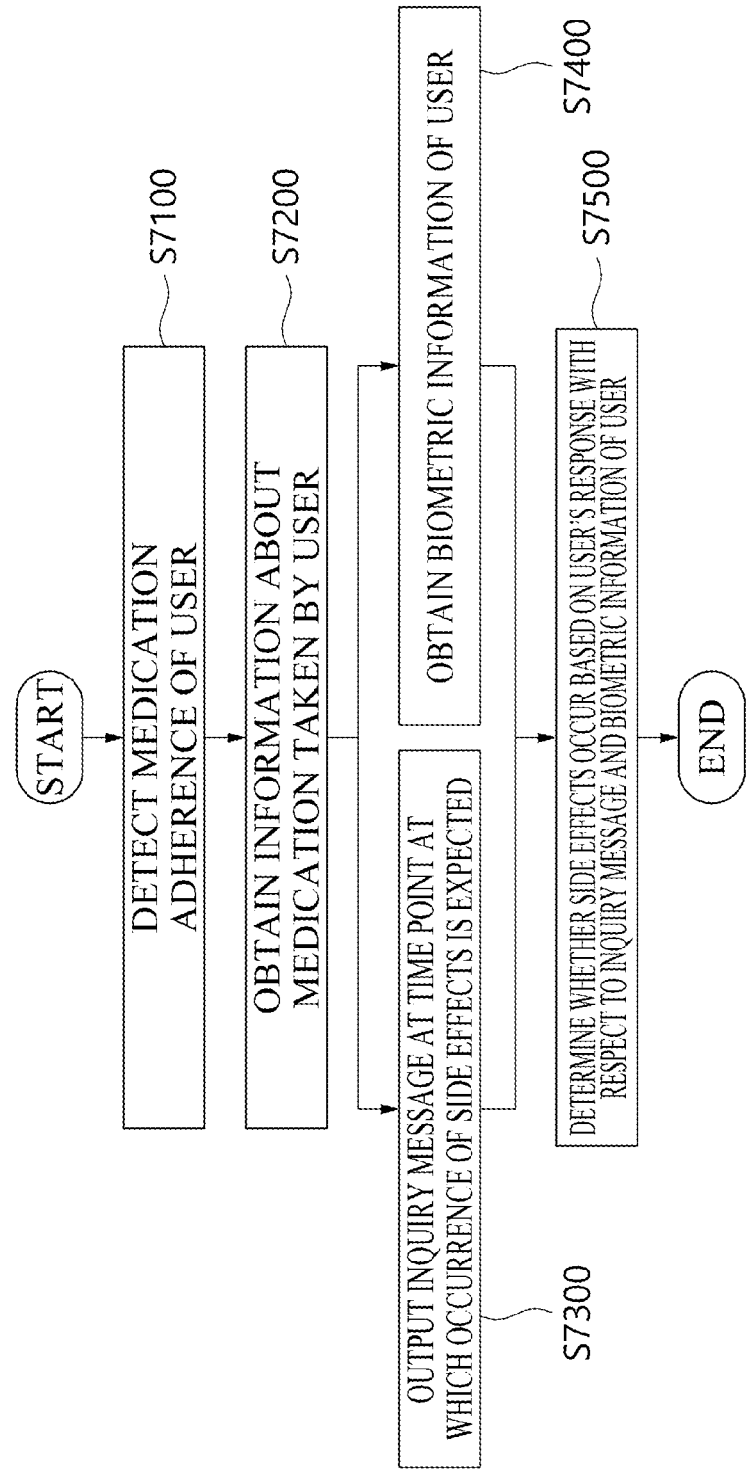
FIG. 36 is a diagram illustrating a method of preventing side effects using a medication adherence monitoring system according to an embodiment of the present invention.

FIG. 36 is a diagram illustrating a method of preventing side effects using the medication adherence monitoring system 100 according to the embodiment of the present invention.

Referring to FIG. 36, the medication adherence monitoring system 100 may perform a step S7100 of detecting the medication adherence of the user, a step S7200 of obtaining information about the medication which is adhered to by the user, a step S7300 of outputting an inquiry message at a time point at which the occurrence of side effects is expected, a step S7400 of obtaining biometric information of the user, and a step S7500 of determining whether side effects occur on the basis of the user's response to the inquiry message and the biometric information of the user.

Hereinafter, each operation will be described in detail.

The medication adherence monitoring system 100 may detect the medication adherence of the user (S7100). As described elsewhere in the present invention, the medication adherence monitoring system 100 may determine whether the user performs the medication adherence by using the wireless communication device 1000, the wearable device 2000, and the server 3000. In this case, the wearable device 2000 and/or the server 3000 may store information such as a type of medication adherence performed by the user, a time point at which the user performs the medication adherence, and/or the number of times the medication adherence is performed.

The medication adherence monitoring system 100 may obtain the information about the medication which is adhered to by the user (S7200). For example, the server 3000 may obtain information about side effects of the medication adherence performed by the user, the time point at which the occurrence of side effects is expected, and/or how to cope with the side effects using pre-stored reference data, and provide the obtained information to the wearable device 2000.

The medication adherence monitoring system 100 may output the inquiry message to the user at the time point at which the occurrence of side effects is expected (S7300). For example, the wearable device 2000 or the terminal device 4000 may output an inquiry message related to the side effect to the user at the time point at which the occurrence of side effects is expected on the basis of the information about the side effects obtained from the server 3000.

Here, the time point at which the inquiry message is output may be set based on a time point at which the time point at which the occurrence of side effects is expected has elapsed from the time point at which the user performs the medication adherence. Further, the inquiry message may be temporarily or periodically output at the time point or the time interval in which the occurrence of side effects is expected.

In addition, here, the inquiry message may be used to inquire whether an abnormal symptom has occurred, a pain score, and/or whether an expected symptom has occurred.

The medication adherence monitoring system 100 may obtain the biometric information of the user (S7400). For example, the wearable device 2000 may include a pulse sensor for detecting the user's pulse, a temperature sensor for detecting the user's body temperature, an acceleration sensor for detecting the user's motion such as shaking of the user's hand or falling, or a gyro sensor, and may temporarily or periodically obtain the biometric information of the user. The biometric information of the user may be temporarily or periodically obtained before and after the time point at which the side effects are expected or may be periodically obtained from the time point at which the user performs the medication adherence. Meanwhile, the biometric information of the user may include not only information measured by the sensor or the like, but also information that may be used to determine the presence or absence of side effects of medication, such as the user's past medical records or health checkup records.

The medication adherence monitoring system 100 may determine whether the side effects occur on the basis of the user's response to the inquiry message and the biometric information of the user (S7500). For example, the wearable device 2000 may transmit the user's response to the inquiry message and the biometric information of the user to the server 3000, and the server 3000 may determine the presence or absence of side effects of the medication by using the received information. Specifically, the server 3000 may determine the presence or absence of side effects of the medication by detecting whether the user is falling, whether a hand is shaking, or changes in pulse, heart rate, and body temperature. In this case, the server 3000 may determine the presence or absence of side effects of the medication by using a database of side effects or an artificial neural network trained to determine the presence or absence of side effects.

The medication adherence monitoring system 100 may serve as a digital therapeutic by providing a duplicate medication notification to prevent the user from overdosing on the medication.

The medication adherence monitoring system 100 may store pieces of information about the time points when it is determined that the user performs the medication adherence, may determine whether the user takes duplicate medications whenever the user has attempted to perform the medication adherence or the user performs the medication adherence, and provide a notification related to the duplicate medications to the user or the like.

Since the content for the medication adherence monitoring system 100 to determine the possibility of taking duplicate medications or whether to take duplicate medications and provide the notification related to the duplicate medications to the user or the like is described elsewhere in the present invention, a description thereof will be omitted.

As described above, the medication adherence monitoring system 100 may detect the side effects due to the medication adherence of the user or prevent the user from taking duplicate medications, and thus it is possible to determine the suitability of the medication adherence to the user or to further improve treatment effects of the medication adherence to the user. As a result, the medication adherence monitoring system 100 may serve as a complementary digital therapeutic having indirect treatment effects.

The medication adherence monitoring system 100 may serve as a digital therapeutic by assisting the user's health promotion. For example, the wearable device 2000 may receive information about the medication, biometric information or status information of the user, information on whether the user performs the medication adherence, or the like from the server 3000 to provide a health promotion induction notification to the user.

Here, the health promotion induction notification may be provided in consideration of the information about the medication that the user adheres to and the status information of the user. For example, the health promotion induction notification may include a sleep-inducing notification or exercise-inducing notification for improving the effectiveness of the medication that the user adheres to, an adverse action prevention notification for preventing side effects of the medication or diminished effectiveness, and the like.

As described above, the medication adherence monitoring system 100 may improve the user's health by inhibiting or inducing the user's action on the basis of a result of the medication adherence, which is obtained by determining whether the user performs the medication adherence, and information about the medication adherence. As a result, the medication adherence monitoring system 100 may serve as an alternative digital therapeutic in that it directly generates an effect of improving the user's health.

Hereinafter, a medication adherence managing tool to which the medication adherence monitoring system 100 is applied will be described with reference to FIGS. 37 to 39.

The medication adherence managing tool may refer to an auxiliary tool for managing the medication adherence of the user or a platform for inducing the medication adherence (hereinafter, referred to as the "medication adherence managing tool"). In particular, when the user suffers from forgetfulness or a mental illness such as dementia or when the user needs the protection or management of a guardian, the user may use the medication adherence managing tool. In this case, the above-described medication adherence monitoring system 100 may be applied to the medication adherence managing tool, and a part of the configuration or operation method of the medication adherence monitoring system 100 may be changed and applied according to the medication adherence managing tool.

Figure 37:
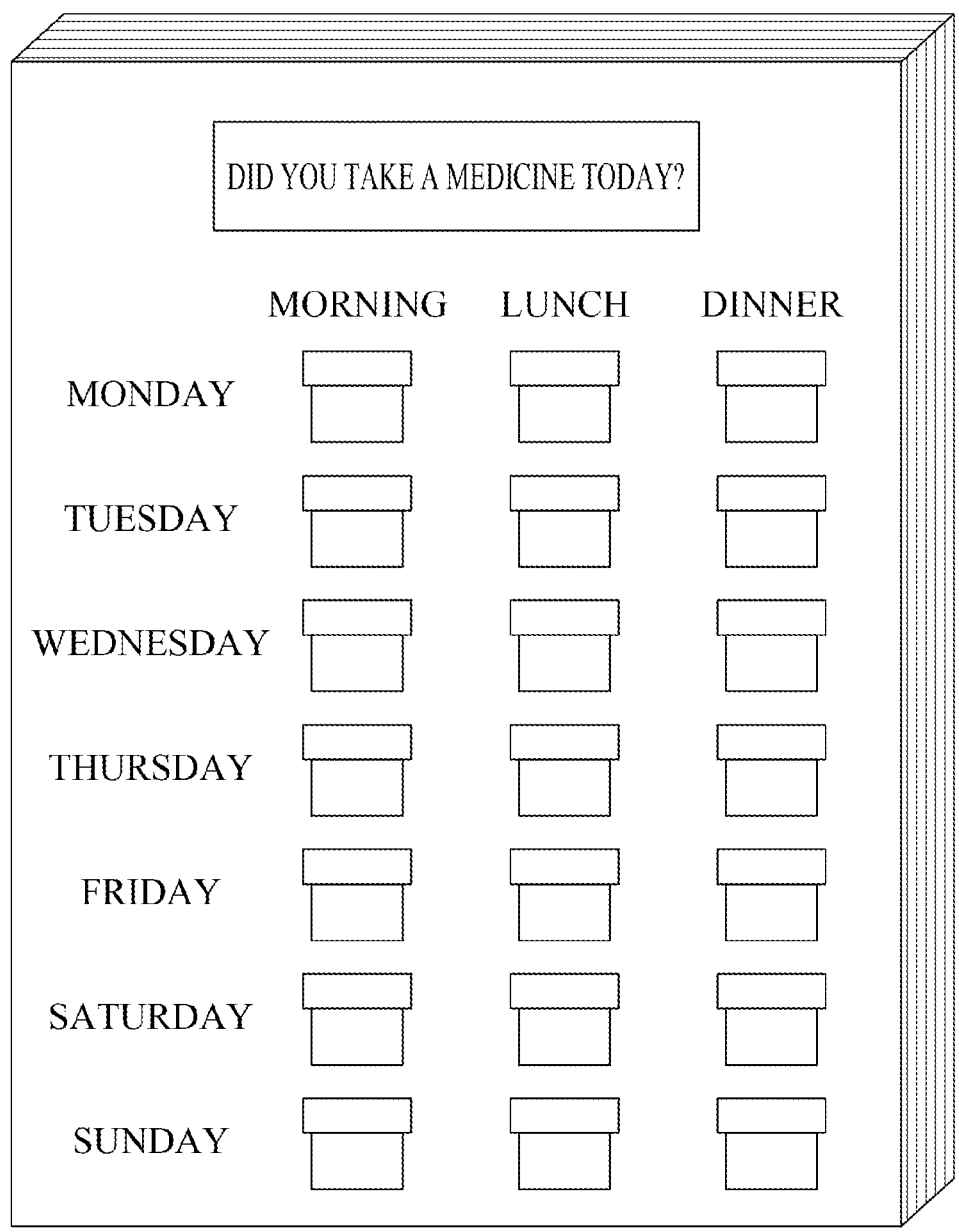
FIGS. 37 to 39 are diagrams illustrating medication adherence managing tools according to an embodiment of the present invention.
Figure 38:
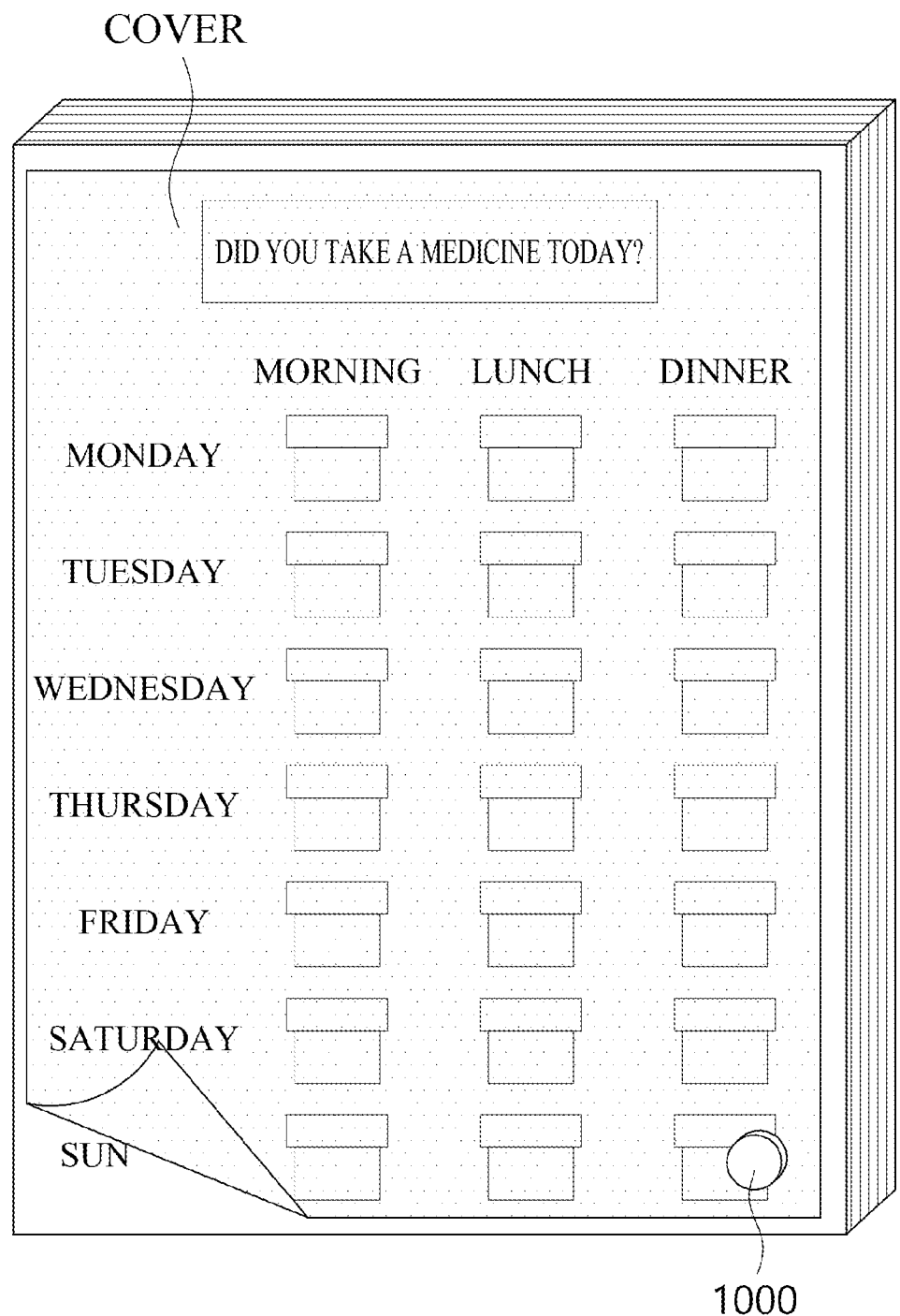
Figure 39:
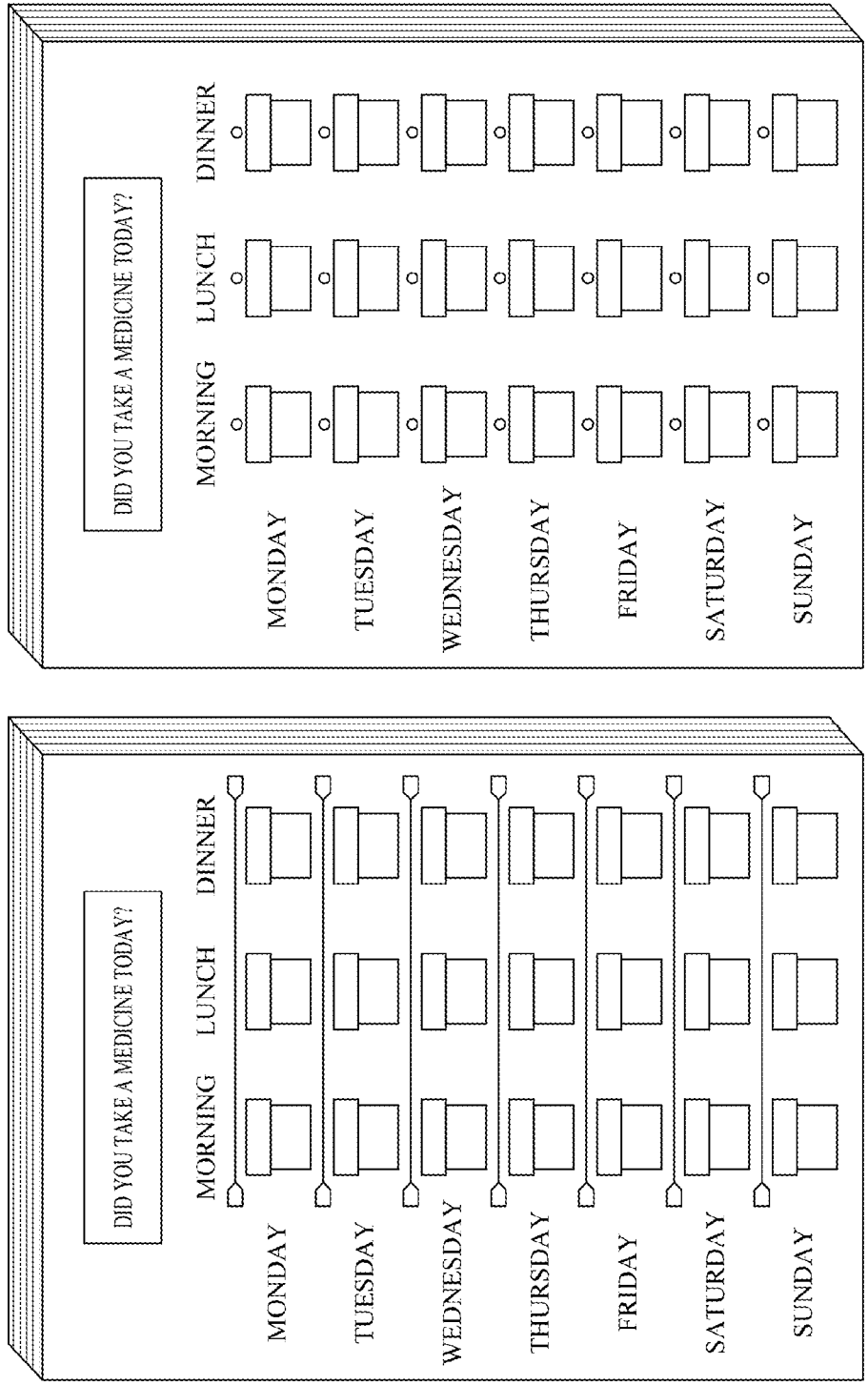

FIGS. 37 to 39 are diagrams illustrating examples of the medication adherence managing tool according to the embodiment of the present invention.

Referring to FIG. 37, the medication adherence managing tool may be implemented as a real-life product in order to induce medication adherence of the user. For example, the medication adherence managing tool may be implemented in the form of a calendar, and a medication accommodating unit for accommodating a medication for each day of week or for each time period may be disposed. The user may take the medication out of the medication accommodating unit according to the day of the week or the time period and perform the medication adherence.

Meanwhile, in the case of the medication adherence managing tool illustrated in FIG. 37, there is a problem in that it is difficult to dispose the wireless communication device 1000 in applying the medication adherence monitoring system 100. In order to solve such a problem, a component may be added to the medication adherence managing tool or a shape of the wireless communication device 1000 may be changed as follows.

Referring to FIG. 38, the medication adherence managing tool may itself perform the function of the wireless communication device 1000 described above. In other words, the medication adherence managing tool may determine whether it is necessary to shoot a video according to the attempt of the medication adherence of the user and transmit activation data to the wearable device 2000.

The medication adherence managing tool may include a sensor unit, a communication unit, and a control unit. For example, the medication adherence managing tool may detect whether the user approaches the medication accommodating unit using a proximity detection sensor disposed adjacent to the medication accommodating unit and transmit the activation data instructing activation of the camera module 2100 to the wearable device 2000. Here, the proximity detection sensor may include an infrared sensor, a passive infrared (PIR) sensor, an ultrasonic sensor, an ambient light sensor, or the like.

Meanwhile, referring to FIG. 39, the medication adherence managing tool may include a component in which the user's motion is detected by the wireless communication device 1000 when used by the user. For example, the medication adherence managing tool may include a cover that covers the medication accommodating unit and inevitably moves when used by the user, and the wireless communication device 1000 may be attached to the cover.

The wireless communication device 1000 may be attached to the cover of the medication adherence managing tool to detect movement of the cover. For example, the first control unit 1400 may obtain a motion value reflecting the movement of the cover using the motion sensor 1110, generate activation data on the basis of the motion value when a motion condition is satisfied, and transmit the generated activation data to the wearable device 2000.

In the above, the form in which the medication adherence managing tool is applied to a schedule managing tool similar to a calendar has been mainly described, but the technological concept of the present invention is not limited thereto, and the medication adherence monitoring system 100 may be applied to any case as long as it is involved in the medication adherence of the user or the induction of the medication adherence.

Meanwhile, the medication adherence monitoring system 100 may be used for monitoring a plurality of users, or a target group (hereinafter, referred to as a "monitoring target") for specific medication adherence. In this case, the medication adherence monitoring system 100 may provide a management service for easier and more efficient monitoring.

The management service may refer to programs or application provided through a wearable device 2000, a server 3000, a terminal device 4000, and/or a separate display device in order to manage the medication adherence of the monitoring target.

The management service may provide the information related to the medication adherence obtained in the medication adherence monitoring system 100. To this end, the management service may be implemented with a specific UI/UX design, a graphical user interface (GUI), or the like.

The management service may be provided to the user, medical personnel, a guardian, or a manager. In this case, the management service may be implemented with different interfaces according to a subject receiving the management service or the information provided by the management service. For example, the management service may include a manager interface provided to the medical personnel, the guardian, or the manager and a private interface provided to the user.

Hereinafter, the management service will be described in more detail with reference to FIGS. 40 to 45.

FIGS. 40 to 44 are diagrams illustrating a management service provided to medical personnel, a guardian, or a manager according to an embodiment of the present invention. Hereinafter, for convenience of description, the case in which the management service includes a manager interface output by the server 3000 is mainly described, but the technological concept of the present invention is not limited thereto, and, for example, even in the case in which the management service is output through the wearable device 2000 or the terminal device 4000, the management service may be similarly applied.

The server 3000 may provide the management service. For example, the server control unit 3400 may output the manager interface through the server input/output unit 3100. Specifically, the server control unit 3400 may display pieces of information about the medication adherence of the user on the server input/output unit 3100, as will be described below.

Here, the server input/output unit 3100 may include a server display on which information is displayed or output and a server input unit that receives an input from the manager or the like. The server control unit 3400 may display the information about the medication adherence of the user, which is stored in the server memory 3200 or obtained from the outside, on the server display, and may change or add the information displayed on the server display on the basis of the input obtained from the server input unit.

Figure 40:
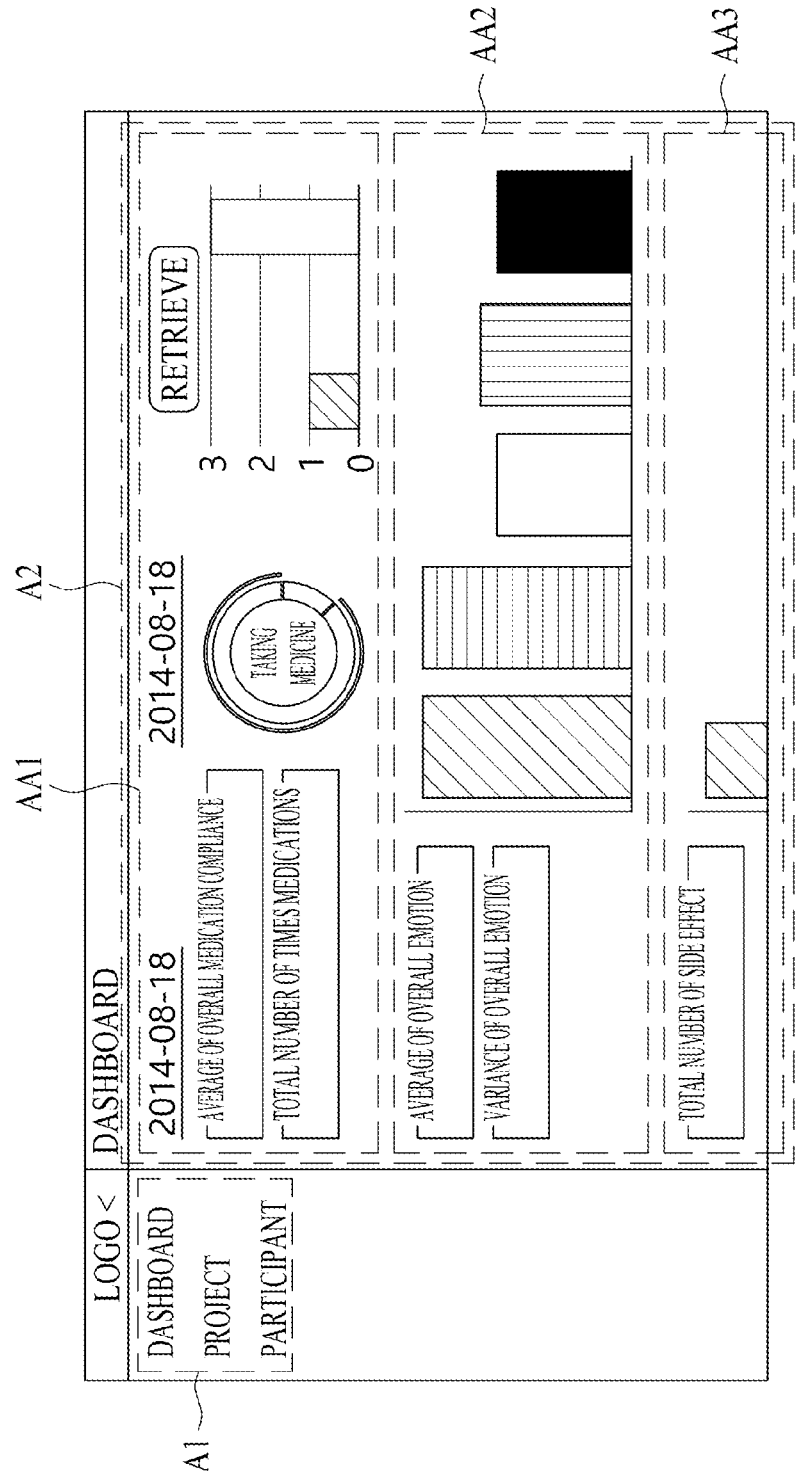

Referring to FIG. 40, contents output to the server display may be divided into a category area A1 and an information display area A2. The category area A1 may be understood as an area for selecting the type of information to be viewed. For example, in the category area A1, "dashboard," "project," and "participating member" may be displayed. The information display area A2 may be understood as an area for outputting information about the type selected in the category area A1. Hereinafter, contents that are displayed in the information display area A2 according to the type of information selected in the category area A1 will be described in detail.

Referring to FIG. 40, when "dashboard" is selected in the category area A1, summary information of the monitoring target may be displayed in the information display area A2. For example, in the information display area A2, the information obtained by using the medication adherence monitoring system 100 may be divided into a medication information area AA1, an emotion information area AA2, and a side effect information area AA3 and displayed.

In the medication information area AA1, information on whether the monitoring target performs the medication adherence may be displayed. For example, in the medication information area AA1, "date," "average of overall medication compliance" that indicates a degree of medication adherence of all monitoring targets, "total number of times medications taken" that indicates the number of times of medication adherence of all monitoring targets, "medication compliance graph" that visually represents medication compliance, and "distribution graph" that visually represents a distribution of monitoring targets for each medication compliance section may be displayed.

In the emotion information area AA2, emotional information input from the monitoring target may be displayed. For example, in the emotional information area AA2, "average of overall emotion" and "variance of overall emotion" related to emotional levels (e.g., for mood, 5: very good, 4: good, 3: normal, 2: bad, and 1: very bad) that are periodically input from the monitoring target, and "graph of emotions" that visually represents the emotional levels may be displayed.

In the side effect information area AA3, information obtained by determining the presence or absence of side effects of the monitoring target may be displayed. For example, in the side effect information area AA3, "total number of side effect inputs" that indicates the number of side effects of the monitoring target, "average of side effects per member" that indicates the average of the number of times of side effects per member of the monitoring target, and "side effect count graph" that visually represents side effect occurrence information may be displayed.

The server 3000 may output a screen including the above-described areas A1, A2, AA1, AA2, and AA3 through the server display. Further, the server 3000 may change the information displayed in the information display area A2 as will be described below on the basis of an input received from the manager in the category area A1.

Referring to FIG. 41, when "project" is selected in the category area A1, information about a project in progress using the medication adherence monitoring system 100 may be displayed in the information display area A2. For example, in the information display area A2, "project name," "start period," "end period," "code," "purpose," "description," "target disease," "disease description,"

"medication name," "number of participants," "qualifying conditions," "non-qualifying conditions," "cautions," etc. may be displayed.

Meanwhile, a first pop-up button B1 for additionally displaying information related to medication adherence performed in the project may be included in the vicinity of "medication name" displayed in the information display area A2. For example, referring to FIGS. 41 and 42, when the pop-up button B1 displayed in the information display area A2 is selected, a first pop-up window PU1 for registering information about the medication which is adhered to by the monitoring target or a second pop-up window PU2 for displaying the information about the medication which is adhered to by the monitoring target may be output. Specifically, in the case in which the server control unit 3400 receives a manager input for the first pop-up button B1, when information about the medication is not stored in the server memory 3200, the first pop-up window PU1 may be displayed on the server display to induce the manager to input the information about the medication, and when the information about the medication is stored in the server memory 3200, the second pop-up window PU2 may be output on the server display on the basis of the stored information about the medication.

In the first pop-up window PUT, "product name," "product code," "product ingredients (in English)," "product ingredients (in native language)," "dosage," "how to take," "administration time," "product descriptions," etc. may be displayed, and pieces of information corresponding thereto may be input by the manager.

In the second pop-up window PU2, the information about the medication adherence performed by the monitoring target may be displayed. In this case, the information about the medication displayed in the second pop-up window PU2 may be displayed based on the pieces of information input by the manager through the first pop-up window PUT. For example, in the second pop-up window PU2, "medication name," "dosage," "medication picture," "medication adherence time," "medication description," etc. may be displayed.

Referring to FIG. 43, when "participating member" is selected in the category area A1, information about users participating in the project in progress using the medication adherence monitoring system 100 may be displayed in the information display area A2. For example, in the information display area A2, "management number," "gender," "age," "degree of medication process," "emotional level," "number of side effects," "pain score," "participation time," "status," and "view" corresponding to each of the users included in the monitoring target may be displayed. Further, in the information display area A2, a second pop-up button B2 for viewing the status of each user of the monitoring target may be displayed.

Figure 44:
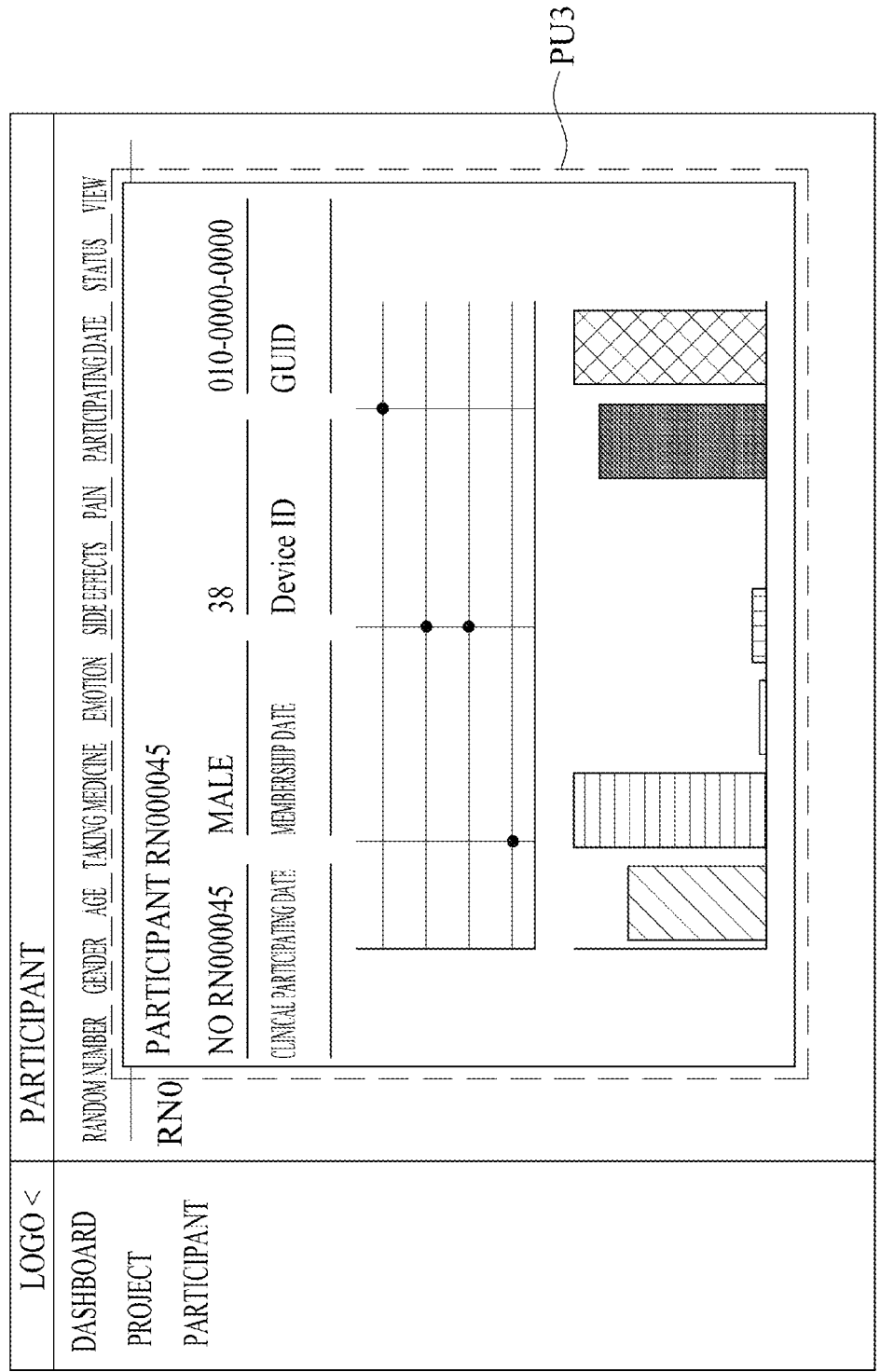

Referring to FIG. 44, when the second pop-up button B2 is selected in the information display area A2, a third pop-up window PU3 on which specific information corresponding to each user of the monitoring target may be output. In this case, in the third pop-up window PU3, "management number," "gender," "age," "contact number," "project participation date," "membership date," "device ID," "GUID," "medication adherence time graph by date," "emotional level graph by day of week," etc. corresponding to each of the users of the monitoring target may be displayed. In this case, the "device ID" may correspond to device identification information of the wearable device 2000 worn by each user, and the "GUID" may correspond to a universal unique identifier of the wireless communication device 1000 provided to each user.

Figure 45:
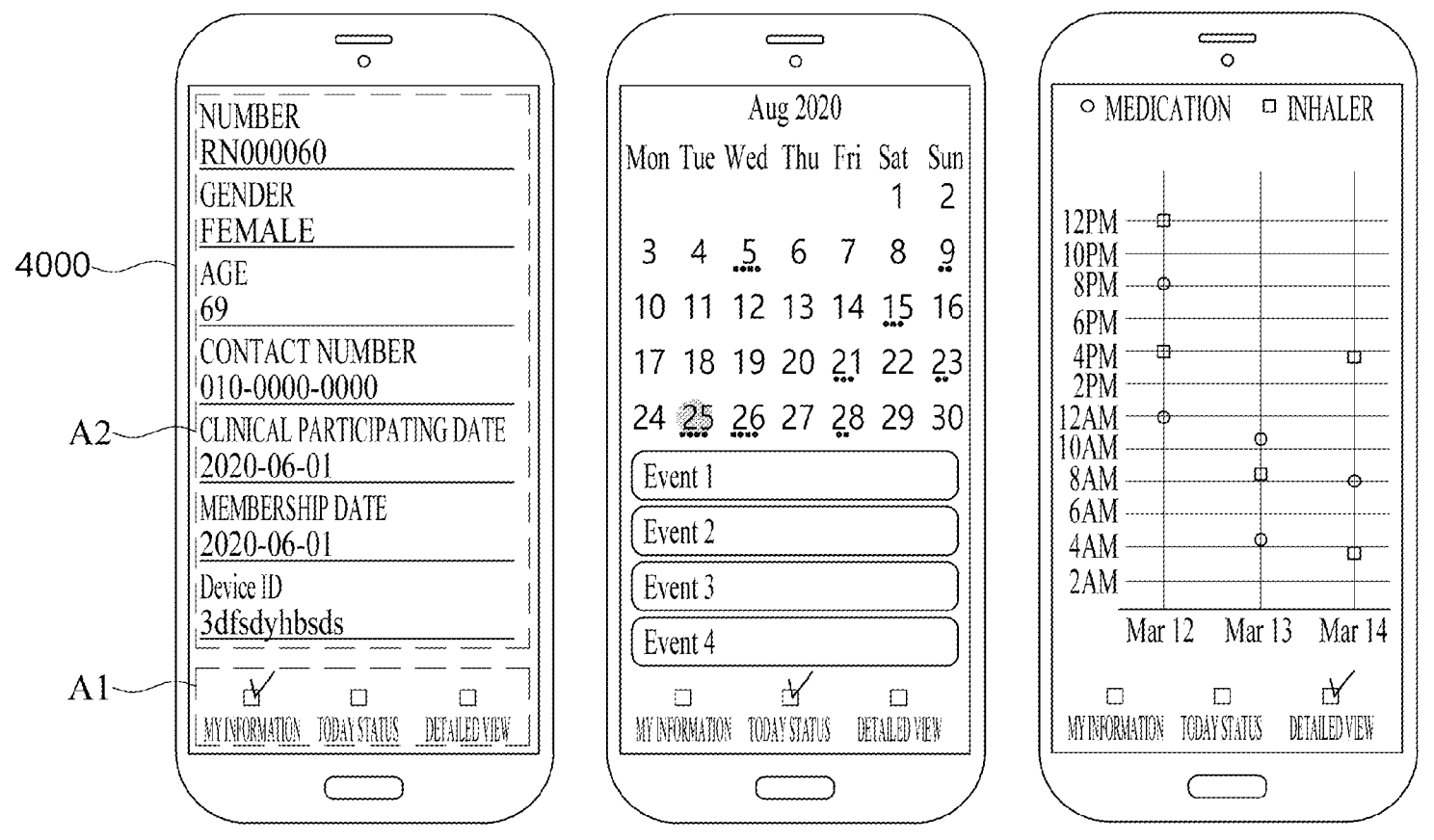

FIG. 45 is a diagram illustrating a management service provided to a user according to an embodiment of the present invention. Hereinafter, the case in which the management service includes a private interface provided to the user through the terminal device 4000 will be mainly described.

The terminal device 4000 may include a display to provide the management service, and may include an input unit to receive the user input. For example, the terminal device 4000 may display pieces of information to be described below on the display, and may change or add the information displayed on the display on the basis of the user input obtained from the input unit.

Referring to FIG. 45, contents output to the terminal device 4000 may be divided into a category area A1 and an information display area A2. The category area A1 may be understood as an area for selecting a type of information to be viewed. For example, in the category area A1, "my information," "today's status," and "detailed view" may be displayed. The information display area A2 may be understood as an area for outputting information about the type selected in the category area A1. Hereinafter, contents, which are displayed in the information display area A2 according to the type of information selected in the category area A1, will be described in detail.

When "my information" is selected in the category area A1, information about the user may be displayed in the information display area A2. For example, referring to FIG. 45, in the information display area A2, "management number," "gender," "age," "contact number," "clinical participation date," "membership date," and "device ID" corresponding to the user may be displayed. In this case, the "device ID" may correspond to device identification information of the wearable device 2000 worn by the user.

When "today's status," is selected in the category area A1, information about events occurring to the user by date may be displayed in the information display area A2. For example, referring to FIG. 45, in the information display area A2, a calendar, on which the number of events occurring by date is displayed, and information about the events occurring by date may be displayed. In this case, when a date is selected by the user on the calendar, information about events corresponding to the selected date may be displayed.

Here, the events may refer to events that may occur as the user performs the medication adherence. For example, the events may include project and/or clinical initiation, issuing a medication prescription, performing medication adherence, not performing medication adherence, checking user status, occurring side effects due to medication adherence, stopping medication adherence, changing medication adherence, consultation with experts related to medication adherence, termination of medication adherence, and the like.

In this case, the event displayed in the information display area A2 may be displayed on the basis of the information obtained by the terminal device 4000 through the user input or the information obtained from the wireless communication device 1000, the wearable device 2000, and/or the server 3000. As an example, as described above, the wearable device 2000 may transmit, to the terminal device 4000, the information about the presence or absence of side effects obtained by determining the presence or absence of side effects using the user's biometric information or the user input, and the terminal device 4000 may display the event related to the side effects in the information display area A2 on the basis of the received information about the presence or absence of the side effects. As another example, the server 3000 may determine whether the user performs the medication adherence using the video data obtained from the wearable device 2000 and transmit information on whether the medication adherence is performed to the terminal device 4000, and the terminal device 4000 may display an event of performing the medication adherence or an event of not performing the medication adherence in the information display area A2 on the basis of the received information on whether the medication adherence is performed.

When "detailed view" is selected in the category area A1, specific information related to the medication adherence of the user may be displayed in the information display area A2. For example, referring to FIG. 45, in the information display area A2, a status of the medication adherence of the user by date and time may be displayed. Specifically, the terminal device 4000 may display in the form of a graph or a table in the information display area A2 on the basis of the information related to the medication adherence of the user obtained from the server 3000.

Here, the information related to the medication adherence of the user may include information on whether the user performs the medication adherence, information about the medication that the user intends to adhere to, information about a time point at which the user performs the medication, and the like. In this case, the information about the time point at which the user performs the medication may include information indicating a time point at which the wearable device 2000 obtains the activation data from the wireless communication device 1000, a time point at which the camera module 2100 of the wearable device 2000 is activated, a time point at which the camera module 2100 is deactivated, a time point selected in a time interval between the above-described time points, or the like.

Meanwhile, the terminal device 4000 may display the status of the medication adherence of the user in the information display area A2 by using the plurality of pieces of information related to the medication adherence. For example, when the user receives a prescription for a first medication and a second medication and performs medication adherence, the terminal device 4000 may obtain information related to first medication adherence for the first medication and information related to second medication adherence for the second medication from the server 3000, and display a status of the first medication adherence and a status of the second medication adherence of the user by time and by date in the information display area A2 on the basis of the obtained information. In this case, the information related to the first medication adherence and the information related to the second medication adherence may be visually distinguished in different shapes or colors and displayed. Here, the information related to the medication adherence is not necessarily the information related to the medication, and may be the information about the health management action described with reference to with reference to FIG. 30, such as an action of using an inhaler or an action of measuring blood glucose.

In the above, the case in which the management service is displayed with the private interface through the terminal device 4000 and provided to the user has been mainly described, but the technological concept of the present invention is not limited thereto, and the management service may be displayed on the wearable device 2000 worn by the user and provided to the user, or may be displayed through the terminal device 4000 and provided to medical personnel, a guardian, a manager or the like.

Features, structures, and effects described in the above-described exemplary embodiments are included in at least one exemplary embodiment of the present invention but are not limited to only one exemplary embodiment. Further, features, structures, and effects exemplified in each exemplary embodiment may be embodied by being combined with another exemplary embodiment or modified by those skilled in the art. It should be interpreted that the combined and modified contents are included in the scope of the present invention.

While the present invention has been particularly described with reference to embodiments, the embodiments are only exemplary embodiments of the present invention and the present invention is not intended to be limited thereto. It will be understood by those skilled in the art that modifications and applications in other forms may be made without departing from the spirit and scope of the present invention. That is, each component specifically shown in the embodiments may be modified and embodied. In addition, it should be understood that differences related to these modifications and applications are within the scope of the present invention as defined in the appended claims.

REFERENCE NUMERALS

100: MEDICATION ADHERENCE MONITORING SYSTEM
1000: WIRELESS COMMUNICATION DEVICE
2000: WEARABLE DEVICE
3000: SERVER
4000: TERMINAL DEVICE

What is claimed is:

1. A wearable device for capturing a video of a health care of a user comprising:
　a camera;
　a communication circuitry; and
　at least one processor, wherein the at least one processor is configured to:
　establish a communication connection with an external device attached to an exterior of an object for the health care through the communication circuitry,
　receive an activation data causing an activation of the camera from the external device through the communication circuitry, wherein the activation data is generated based on ambient light values and motion values obtained by the external device,
　activate the camera based on the activation data to obtain the video related to the health care of the user,
　receive, from the external device, an identification data related to a type of the object for determining a time period for activating the camera, through the communication circuitry,
　when the identification data corresponds to a first identification data related to a first type of the object, obtain the video by activating the camera for a first time period based on the first identification data, and
　when the identification data obtained corresponds to a second identification data related to a second type of the object, obtain the video data by activating the camera for a second time period based on the second identification data.

2. The wearable device of claim 1,
　wherein the identification data corresponds to a unique identification data of the external device, and
　wherein the time period corresponds to the unique identification data.

3. The wearable device of claim 1,
　wherein the identification data corresponds to a data indicative of the object, and
　wherein the time period corresponds to the object.

4. The wearable device of claim 1,
wherein the object is at least one of a drug container, a drug delivery device, or a biometric measurement device.

5. The wearable device of claim 1,
wherein the object is at least one of a medicine container, a medicine bottle, a blister pack, an eye drop bottle, a portable medicine cabinet, a medicine box, a medicine bag, a medicine calendar, a dispensing dispenser, an inhaler, a spray, a syringe, a patch, a glucometer, a sphygmomanometer, or an electrocardiography devices.

6. A wearable device for taking images of a health care of a user,
a camera,
a communication circuitry; and
at least one processor,
wherein the at least one processor is configured to:
establish, through the communication circuitry, a communication connection with a first wireless communication device attached to an exterior of a first object and a second wireless communication device attached to an exterior of a second object,
receive, from the first wireless communication device, through the communication circuitry, a first activation data causing an activation of the camera data and a first identification data, wherein the first activation data is generated based on ambient light values and motion values, and the first identification data is related to a first object type for determining a time period of the activation of the camera,
obtain a first video data activating the camera for a first time period based on the first activation data, wherein the first time period is determined based on the first identification data obtained by the first wireless communication device,
receive, from the second wireless communication device, through the communication circuitry, a second activation data causing an activation of the camera data, the second identification data, wherein the second activation data is generated based on ambient light values and motion values and a second identification data is related to a second object type for determining a time period of the activation of the camera,
obtain a second video data activating the camera for a second time period based on the second activation data wherein the second time period is determined based on the second identification data obtained by the second wireless communication device.

7. The wearable device of claim 6,
wherein the at least one processor is further configured to:
activate the camera at a first time point based on the first activation data,
receive the second activation data from the second wireless communication device before the first time period elapses from the first time point, and
activate the camera for a third time period that is longer than the first time period at the first time point.

8. The wearable device of claim 7,
wherein the third time period is established to a time period greater than the sum of the first time period and the second time period.

9. The wearable device of claim 6,
the at least one processor is configured to:
activate the camera at the first time point based on the first activation data,
receive the second activation data from the second wireless communication device at the second time point that is before the first time period elapses, and
activate the camera during the second time period at the second time point.

10. A monitoring system for capturing an image used to determine whether a user is performing a health care including:
a wireless communication device attached to an exterior of an object for the health care of the user including:
an ambient light sensor;
a motion sensor; and
a first communication circuitry;
at least one first processor;
a wearable device including:
a camera;
a second communication circuitry; and
at least one second processor;
wherein the at least one first processor is configured to:
establish a communication connection with the wearable device through the first communication circuitry,
obtain an activation data instructing activation of the camera of the wearable device using an ambient light value corresponding to a brightness of surroundings of the wireless communication device, obtained from the ambient light sensor, and a motion value corresponding to a movement of the wireless communication device, obtained from the motion sensor,
transmit the activation data and an identification data to the wearable device through the first communication circuitry, wherein the identification data is related to a type of the object in order to determine a time period of activation of the camera,
wherein the at least one second processor is configured to:
activate the camera for the time period based on the activation data received from the wireless communication device,
when the identification data corresponds to a first identification data related to a first type of the object, set the time period to a first time period, and
when the identification data corresponds to a second identification data related to a second type of the object, set the time period to a second time period.

11. The monitoring system for capturing the image used to determine whether the user is performing the health care of claim 10,
wherein the identification data corresponds to a unique identification data of the wireless communication device,
wherein the time period corresponds to the unique identification data.

12. The monitoring system for capturing the image used to determine whether the user is performing the health care of claim 10,
wherein the identification data corresponds to a data indicative of an object used for the health care of the user,
wherein the time period corresponds to the object.

13. The monitoring system for capturing the image used to determine whether the user is performing the health care of claim 12,
wherein the object is at least one of a drug container, a drug delivery device, or a biometric measurement device.

14. The monitoring system for capturing the image used to determine whether the user is performing the health care of claim 12, wherein the object is at least one of a medicine cabinet, a medicine bottle, a blister pack, an eye drop bottle, a portable medicine cabinet, a medicine box, a medicine bag, a medicine calendar, a dispenser, an inhaler, a spray, a syringe, a patch, a glucometer, a sphygmomanometer, or an electrocardiogram device.

* * * * *